(12) United States Patent
Swann et al.

(10) Patent No.: US 11,585,278 B1
(45) Date of Patent: Feb. 21, 2023

(54) AVIATION FUEL

(71) Applicant: ROLLS-ROYCE plc, London (GB)

(72) Inventors: Peter Swann, Derby (GB); David M Beaven, Nottingham (GB); Craig W Bemment, Derby (GB); Alastair G Hobday, Derby (GB); Benjamin J Keeler, Derby (GB); Christopher P Madden, Derby (GB); Martin K Yates, East Haddon (GB)

(73) Assignee: ROLLS-ROYCE plc, London (GB)

( * ) Notice: Subject to any disclaimer, the term of this patent is extended or adjusted under 35 U.S.C. 154(b) by 0 days.

(21) Appl. No.: 17/853,144

(22) Filed: Jun. 29, 2022

(30) Foreign Application Priority Data

Dec. 21, 2021 (GB) .................................... 2118647

(51) Int. Cl.
| | |
|---|---|
| *G01N 21/35* | (2014.01) |
| *F02C 9/00* | (2006.01) |
| *B64D 27/10* | (2006.01) |
| *B64D 47/00* | (2006.01) |
| *G01N 33/28* | (2006.01) |
| *G01N 21/64* | (2006.01) |
| *G01N 21/33* | (2006.01) |
| *G01N 21/3577* | (2014.01) |
| *B64D 37/00* | (2006.01) |

(52) U.S. Cl.
CPC ................ *F02C 9/00* (2013.01); *B64D 27/10* (2013.01); *B64D 47/00* (2013.01); *G01N 21/33* (2013.01); *G01N 21/3577* (2013.01); *G01N 21/64* (2013.01); *G01N 33/287* (2013.01); *B64D 37/00* (2013.01); *G01N 2021/3595* (2013.01)

(58) Field of Classification Search
CPC .......... F02C 9/00; B64D 27/10; B64D 47/00; B64D 37/00; G01N 21/33; G01N 21/3577; G01N 21/64; G01N 33/287; G01N 2021/3595
See application file for complete search history.

(56) References Cited

U.S. PATENT DOCUMENTS

| | | | |
|---|---|---|---|
| 6,226,976 B1 | 5/2001 | Scott et al. | |
| 2011/0101166 A1 | 5/2011 | Schwarze et al. | |
| 2013/0044324 A1* | 2/2013 | Rebinsky ............. | G01N 33/287 |
| | | | 356/441 |

FOREIGN PATENT DOCUMENTS

EP        0826956 B1 *   7/2005     ........... G01N 21/255

OTHER PUBLICATIONS

ASTM Standard D7566, "Standard Specification for Aviation Turbine Fuel Containing Synthesized Hydrocarbons," ASTM International, Jul. 1, 2021.

\* cited by examiner

*Primary Examiner* — Kiho Kim
(74) *Attorney, Agent, or Firm* — Oliff PLC

(57) ABSTRACT

A method of determining one or more fuel characteristics of an aviation fuel for powering a gas turbine engine of an aircraft includes: measuring one or more trace substance parameters of the fuel, the one or more trace substance parameters each associated with a respective trace substance in the fuel; and determining one or more fuel characteristics of the fuel based on the one or more trace substance parameters. Further, a fuel characteristic determination system, a method of operating an aircraft, and an aircraft.

20 Claims, 17 Drawing Sheets

AVIATION FUEL

CROSS-REFERENCE TO RELATED APPLICATIONS

This specification is based upon and claims the benefit of priority from UK Patent Application Number 2118647.3 filed on 21 Dec. 2021, the entire contents of which are incorporated herein by reference.

BACKGROUND

Field of the Disclosure

The present disclosure relates to methods of determining one or more fuel characteristics of an aviation fuel for powering a gas turbine engine of an aircraft, and fuel characteristic determination systems for the same. The present disclosure further relates to methods of operating an aircraft, for example according to the determined fuel characteristics, and an aircraft having a fuel characteristic determination system and a control system. The present disclosure further relates to a method of generating a maintenance schedule for an aircraft, a maintenance schedule generation system, and a method of maintaining an aircraft.

Description of the Related Art

There is an expectation in the aviation industry of a trend towards the use of fuels different from the traditional kerosene-based jet fuels generally used at present. These fuels may have differing fuel characteristics, for example having either or both of a lower aromatic content and sulphur content, relative to petroleum-based hydrocarbon fuels.

In order to take advantage of the different properties of these fuels there is a need for methods of determining fuel characteristics, either on board an aircraft during its operation, or as it is being refueled. Based on this determination the aircraft, and more specifically a gas turbine engine used to power it, can be operated or maintained accordingly. This may provide performance benefits and/or environmental benefits by making better use of the characteristics of the fuel present onboard the aircraft.

SUMMARY

According to a first aspect there is provided a method of determining one or more fuel characteristics of an aviation fuel suitable for powering a gas turbine engine of an aircraft, the method comprising:
  exposing the surface of a piezoelectric crystal to the fuel;
  measuring a vibration parameter of the piezoelectric crystal; and
determining one or more fuel characteristics of the fuel based on the vibration parameter.

The inventors have determined that the vibrational properties of a piezoelectric crystal varies according to the characteristics of fuel to which it has been exposed. By measuring a vibrational parameter of the crystal, characteristics of the fuel to which it has been exposed may therefore be determined. For example, deposits may be formed on the crystal surface by exposure to fuel. By measuring a vibration parameter of the crystal (e.g. a resonant frequency) the amount surface deposition on the crystal surface can be determined, and the characteristics of the fuel which caused those deposits determined.

The vibration parameter may be indicative of a surface deposition formed on the surface of the piezoelectric crystal which has been exposed to the fuel.

Measuring the vibration parameter may comprise measuring a change in a vibrational mode of the piezoelectric crystal.

The one or more fuel characteristics determined may include a hydrocarbon distribution of the fuel.

The one or more fuel characteristics determined may include any one or more of: (i) the percentage of sustainable aviation fuel in the fuel; and/or (ii) the aromatic hydrocarbon content of the fuel.

The one or more fuel characteristics may include any one or more of: (i) an oxygen content of the fuel; (ii) a thermal stability of the fuel; and/or (iii) a coking level of the fuel.

The fuel may be exposed to the surface of the piezoelectric crystal during use of the gas turbine engine.

The method may comprise exposing fuel within a fuel system of the gas turbine engine to the surface of the piezoelectric crystal. Preferably the fuel may be exposed to the piezoelectric crystal after the fuel has been heated by a heat exchanger of the gas turbine engine.

Fuel within, sampled from, or being delivered to a fuel tank of the aircraft may be exposed to the surface of the piezoelectric crystal.

Measuring the vibration parameter may comprise exposing the piezoelectric crystal to fuel outside of the aircraft during a fuel loading process in which a fuel tank or tanks of the aircraft are loaded with fuel.

According to a second aspect, the present application provides a fuel characteristic determination system for determining a fuel characteristic of an aviation fuel suitable for powering a gas turbine engine of an aircraft, the system comprising:
  a sensor comprising a piezoelectric crystal, a surface of the piezoelectric crystal adapted to be exposed to the fuel, the sensor being arranged to measure a vibration parameter of the piezoelectric crystal; and
  a fuel characteristic determination module arranged to determine one or more fuel characteristics of the fuel based on the vibration parameter.

The vibration parameter may be indicative of a surface deposition formed on the surface of the piezoelectric crystal (which has been exposed to the fuel).

The sensor may be arranged to measure a change in a vibrational mode of the piezoelectric crystal in order to measure the vibrational parameter.

The one or more fuel characteristics determined may include any one or more of: (i) a hydrocarbon distribution of the fuel; (ii) a percentage of sustainable aviation fuel in the fuel; (iii) an aromatic hydrocarbon content of the fuel; (iv) an oxygen content of the fuel; (v) a thermal stability of the fuel; and/or (vi) a coking level of the fuel.

The fuel may be exposed to the surface of the piezoelectric crystal during use of the gas turbine engine.

The piezoelectric crystal may be adapted for exposure to fuel within a fuel system of the gas turbine engine. Preferably, the piezoelectric crystal may be adapted to be located at a position downstream (in the direction of fuel flow) of a heat exchanger of the gas turbine engine.

The piezoelectric crystal may be adapted for exposure to fuel that is within, sampled from, or being delivered to a fuel tank of the aircraft. The piezoelectric crystal may be adapted for exposure to fuel outside of the aircraft, the fuel being loaded onto the aircraft during a fuel loading process. The piezoelectric crystal may be provided in a fuel loading line or fuel storage vessel of a refueling system.

According to a third aspect, the present application provides a method of operating an aircraft having a gas turbine engine, the method comprising:
  determining one or more fuel characteristics using the method of the first aspect; and
  operating the aircraft according to the one or more fuel characteristics.

Operating the aircraft according to the one or more fuel characteristics may comprise:
  a) modifying a control parameter of the aircraft, preferably a control parameter of the gas turbine engine, in response to the one or more fuel characteristics; and/or
  b) providing a fuel having different fuel characteristics (to those of the fuel for which the fuel characteristics have been determined) during refueling of the aircraft.

According to a fourth aspect, the present application provides an aircraft comprising the fuel characteristic determination system of the second aspect, the aircraft further comprising a control system arranged to control operation of the aircraft according to the one or more fuel characteristics determined by the fuel characteristic determination system.

According to a fifth aspect, the present application provides a method of determining one or more fuel characteristics of an aviation fuel for powering a gas turbine engine of an aircraft, the method comprising:
  exposing the surface of a sensor component formed from a nitrile seal material to the fuel;
  measuring a swell parameter of the seal material; and
  determining one or more fuel characteristics of the fuel based on the swell parameter.

The inventors have determined that a swell parameter of a seal material, such as a nitrile seal, may be used to determine the characteristics of a fuel to which the seal material has been exposed. The inventors have determined that the degree to which the nitrile material swells on exposure to the fuel is dependent on the characteristics of the fuel, and can be used as a sensor to determine such characteristics.

Measuring the swell parameter may comprise measuring the expansion or contraction of the sensor component as a result of exposure to the fuel.

Measuring the expansion or contraction of the sensor component may comprise measuring a change in physical size of the sensor component, or measuring a force applied to a gauge by the sensor component.

The one or more fuel characteristics determined may include a hydrocarbon distribution of the fuel.

The one or more fuel characteristics determined may include any one or more of: (i) a percentage of sustainable aviation fuel in the fuel; (ii) an aromatic hydrocarbon content of the fuel; and/or (iii) a cycloparaffin content of the fuel.

The method may further comprise generating an alert signal if the swell parameter is outside of an alert threshold. The alert signal may be generated if the swell parameter is outside of a safe operating range.

The fuel may be exposed to the surface of the sensor component during use of the gas turbine engine.

The fuel may be exposed to the surface of the sensor component within a fuel system of the gas turbine engine. The fuel may be exposed to the surface of the sensor component in a bleed line of the fuel system of the gas turbine engine.

Fuel within, sampled from, or being delivered to a fuel tank of the aircraft may be exposed to the surface of the sensor component. Measuring the swell parameter may comprise exposing the sensor component to fuel outside of the aircraft during a fuel loading process in which a fuel tank or tanks of the aircraft are loaded with fuel. The sensor component may be provided in a fuel loading line or fuel storage vessel of a refueling system for the aircraft.

According to a sixth aspect, the present application provides a fuel characteristic determination system for determining one or more fuel characteristics of an aviation fuel for powering a gas turbine engine of an aircraft, the system comprising:
  a sensor component formed from a nitrile seal material, a surface of the sensor component adapted to be exposed to the fuel;
  a sensor arranged to measure a swell parameter of the seal material; and
  a fuel characteristic determination module arranged to determine one or more fuel characteristics of the fuel based on the swell parameter.

The sensor component formed from the seal material may be arranged to be fixedly mounted relative to a gauge. The gauge may be arranged to detect movement of the sensor component due to expansion or contraction.

The gauge may be arranged to detect a change in physical size of the sensor component.

The gauge may be arranged to detect a pressure exerted by the sensor component resulting from its expansion or contraction.

The one or more fuel characteristics determined by the fuel characteristic determination module may include a hydrocarbon distribution of the fuel.

The one or more fuel characteristics determined by the fuel characteristic determination module may include any one or more of: (i) a percentage of sustainable aviation fuel in the fuel; (ii) an aromatic hydrocarbon content of the fuel (F); and/or (iii) a cycloparaffin content of the fuel.

The fuel characteristic determination system may be further arranged to generate an alert signal if the swell parameter is beyond an alert threshold.

The sensor component may be adapted to be located on board the aircraft. The sensor component may be arranged so that fuel is exposed to its surface during operation of the gas turbine engine.

The sensor component may be adapted for exposure to fuel within, sampled from, or being delivered to a fuel tank of the aircraft. The sensor component may be adapted for exposure to fuel outside of the aircraft, the fuel being loaded onto the aircraft during a fuel loading process. The sensor component may be provided in a fuel loading line or fuel storage vessel of a refueling system for the aircraft.

According to a seventh aspect, the present application provides a method of operating an aircraft having a gas turbine engine, the method comprising:
  determining one or more fuel characteristics using the method of the fifth aspect; and
  operating the aircraft according to the one or more fuel characteristics.

Operating the gas turbine engine or the aircraft according to the one or more fuel characteristics may comprise:
  a) modifying a control parameter of the aircraft, preferably a control parameter of the gas turbine engine, in response to the one or more fuel characteristics; and/or
  b) providing a fuel having different fuel characteristics during refueling of the aircraft.

Modifying a control parameter of the aircraft may comprise modifying a control parameter which controls a selection of fuel to be supplied to the gas turbine engine from different fuel sources on board the aircraft so as to provide fuel having a different fuel characteristic (from that of the fuel determined).

Providing fuel having a different fuel characteristic may comprise any one or more of: i) providing fuel with a relatively higher aromatic content; ii) providing fuel with a relatively lower SAF content; and/or iii) providing fossil kerosene fuel.

According to an eighth aspect, the present application provides an aircraft, comprising:
 a gas turbine engine;
 a fuel system comprising one or more fuel tanks arranged to contain fuel for supply to the gas turbine engine, the fuel system comprising one or more seals, the seals being exposed at least partly to the fuel;
 a detection device located within the fuel system and comprising a sensor component made of the same material as the one or more seals, the detection device being arranged to measure a swell parameter of the seal material.

By measuring the level of swell of a sensor component made from the same material as one or more seals provided in the aircraft fuel system the behaviour of those seals as a result of exposure to the fuel can be indirectly determined. This may provide an indication that an inadequate (e.g. too little) amount of seal swell has, or is, occurring to provide sufficient sealing performance.

The detection device may be arranged to measure the expansion or contraction of the sensor component as a result of exposure to the fuel.

The detection device may be arranged to measure a change in physical size of the sensor component. The detection device may be arranged to measure a force applied to a gauge by the sensor component.

The aircraft may further comprise a fuel characteristic determination module arranged to determine one or more fuel characteristics of the fuel based on the swell parameter.

The one or more fuel characteristics may include any one or more of: (i) a hydrocarbon distribution of the fuel; (ii) a percentage of sustainable aviation fuel in the fuel; (iii) an aromatic hydrocarbon content of the fuel; and/or (iv) a cycloparaffin content of the fuel.

The detection device may be arranged to generate an alert signal if the swell parameter is beyond an alert threshold.

According to a ninth aspect, the present application provides a method comprising:
 exposing one or more seals of a fuel system of an aircraft to fuel within the fuel system, the aircraft having a gas turbine engine supplied by fuel by the fuel system exposing a sensor component, made from the same material as the one or more seals, to the fuel, the component being located within the fuel system; and
 measuring a swell parameter of the seal material.

The method may further comprise determining one or more fuel characteristics of the fuel based on the swell parameter.

The method may further comprise generating an alert signal if the swell parameter is beyond an alert threshold.

According to a tenth aspect, the present application provides a method of operating an aircraft having one or more gas turbine engines, comprising:
 measuring a swell parameter of a seal material using the method of the ninth aspect; and
 operating the aircraft according to the swell parameter.

Operating the aircraft according to the swell parameter may include providing the one or more gas turbine engines with fuel having a different characteristic compared to the fuel for which the seal swell has been determined. This may be done by either refueling the aircraft or by talking fuel from a different source aboard the aircraft.

Providing fuel having a different characteristic may comprise any one or more of: i) providing fuel with a relatively higher aromatic content; ii) providing fuel with a relatively lower SAF content; and/or iii) providing kerosene.

According to an eleventh aspect, the present application provides an aircraft comprising the fuel determination system of the sixth aspect, the aircraft further comprising a control system arranged to control operation of the aircraft according to the one or more fuel characteristics determined by the fuel determination system.

According to a twelfth aspect, the present application provides an aircraft according to the eight aspect, the aircraft further comprising a control system arranged to control operation of the aircraft according to the swell parameter measured by the detection device.

According to a thirteenth aspect, the present application provides a method of determining one or more fuel characteristics of an aviation fuel for powering a gas turbine engine of an aircraft, the method comprising:
 measuring one or more trace substance parameters of the fuel, the one or more trace substance parameters each associated with a respective trace substance in the fuel; and
 determining one or more fuel characteristics of the fuel based on the one or more trace substance parameters.

The inventors have determined that by measuring trace substance parameters of a fuel, certain characteristics of that fuel may be determined. Such trace substances may be present in only a trace amount and may indicate an associated characteristic of the fuel by their presence, concentration or absence in the fuel.

At least one of the one or more trace substance parameters may indicate the presence or a concentration of the associated trace substance in the fuel.

At least one of the one or more trace substance parameters may indicate the absence of the associated trace substance in the fuel.

The one or more fuel characteristics determined may include:
a) a percentage of sustainable aviation fuel in the fuel; or
b) an indication that the fuel is a fossil fuel, for example fossil kerosene fuel.

The trace substance associated with at least one of the substance parameters may occur inherently in the fuel. For example, it may occur naturally in the fuel as a result of its manufacture.

The trace substance parameters may include:
i) a concentration or amount of sulphur within the fuel; and/or
ii) a concentration or amount of aromatic hydrocarbon within the fuel.

The trace substance associated with at least one of the trace substance parameters may be added to the fuel to act as a tracer for detection. For example, the trace substance may be added to the fuel for the purpose of acting as a tracer to indicate a certain characteristic or characteristics of the fuel.

Measuring the one or more trace substance parameters may comprise performing spectroscopy on the fuel. Preforming spectroscopy on the fuel may comprise performing Fourier Transform Infrared (FT-IR) or Ultraviolet Visual (UV-Vis) spectroscopy.

Measuring the one or more trace substance parameters may comprise performing fluorescence detection.

Measuring the one or more trace substance parameters may comprise performing a measurement on fuel onboard the aircraft.

Measuring the one or more trace substance parameters may comprise performing a measurement on fuel within, sampled from, or being delivered to a fuel tank of the aircraft.

Measuring the one or more trace substance parameters may comprise performing a measurement on fuel during use of the gas turbine engine. This may include performing a measurement on fuel while it is within a fuel system of the gas turbine engine.

Measuring the one or more trace substance parameters may comprise performing a measurement on fuel outside of the aircraft during a fuel loading process in which the fuel tank or tanks of the aircraft are loaded with fuel. A sensor to measure the trace substance parameters may therefore be located in a fuel loading system for the aircraft.

According to a fourteenth aspect, the present application provides a fuel characteristic determination system for determining one or more fuel characteristics of an aviation fuel for powering a gas turbine engine of an aircraft, the system comprising:
  a sensor configured to measure one or more trace substance parameters of the fuel, the one or more trace substance parameters each associated with a respective trace substance in the fuel; and
  and determination module configured to determine one or more fuel characteristics of the fuel based on the one or more trace substance parameters.

At least one of the one or more trace substance parameters may indicate the presence or a concentration of the associated trace substance in the fuel.

At least one of the one or more trace substance parameters may indicate the absence of the associated trace substance in the fuel.

The one or more fuel characteristics determined may include:
a) a percentage of sustainable aviation fuel in the fuel; or
b) an indication that the fuel is a fossil fuel, for example, fossil kerosene fuel.

The trace substance associated with at least one of the trace substance parameters may occur inherently in the fuel.

The trace substance parameter may be:
a) a concentration or amount of sulphur within the fuel (F); and/or
b) a concentration or amount of aromatic hydrocarbon in the fuel (F).

The trace substance associated with at least one of the trace substance parameters may be added to the fuel to act as a tracer for detection.

The sensor may comprise a spectroscopy device. The spectroscopy device may preferably be Fourier Transform Infrared (FT-IR) or Ultraviolet Visual (UV-Vis) spectroscopy device.

The sensor may comprise a fluorescence detection device.

The sensor may be configured to perform a measurement on fuel onboard the aircraft.

The sensor may be arranged to perform a measurement on fuel within, sampled from, or being delivered to a fuel tank of the aircraft.

The sensor may be arranged to perform a measurement on fuel during use of the gas turbine engine. The sensor may be located within a fuel system of the gas turbine engine.

The sensor nay be arranged to perform a measurement on fuel outside of the aircraft that is being loaded onto the aircraft during a fuel loading process. For example, the sensor may be located within re-fueling system of the aircraft.

According to a fifteenth aspect, the present application provides a method of operating an aircraft having a gas turbine engine, the method comprising:
  determining one or more fuel characteristics using the method of the thirteenth aspect; and
  operating the aircraft according to the one or more fuel characteristics.

Operating the aircraft according to the one or more fuel characteristics may comprise:
  a) modifying a control parameter of the aircraft, preferably a control parameter of the gas turbine engine, in response to the one or more fuel characteristics; and/or
  b) providing a fuel having different fuel characteristics during refueling of the aircraft.

According to a sixteenth aspect, the present application provides an aircraft comprising the fuel characteristic determination system of the fourteenth aspect, the aircraft further comprising a control system arranged to control operation of the aircraft according to the one or more fuel characteristics determined by the fuel characteristic determination system.

According to a seventeenth aspect, there is provide a method of determining one or more fuel characteristics of an aviation fuel suitable for powering a gas turbine engine of an aircraft, the method comprising:
  passing UV-visual spectrum light through the fuel;
  measuring a transmittance parameter indicating the transmittance of light through the fuel;
  determining one or more fuel characteristics of the fuel based on the transmittance parameter; and
  communicating the one or more fuel characteristic to a control system of the gas turbine engine or the aircraft.

The inventors have determined that by measuring the UV-Visual spectrum light transmittance properties of an aviation fuel, characteristics of that fuel can be determined and communicated to a control module of the aircraft so that the aircraft can be operated based on them.

The transmittance parameter may indicate the transmittance of the UV-visual spectrum light as a function of wavelength.

The one or more fuel characteristics determined based on the transmittance parameter may include a hydrocarbon distribution of the fuel.

The one or more fuel characteristics may include any one or more of: (i) an aromatic hydrocarbon content of the fuel; ii) a percentage of sustainable aviation fuel in the fuel; and/or iii) an indication as to whether the fuel is fossil fuel, e.g. fossil kerosene.

The UV-visual spectrum light may be passed though the fuel within, sampled from, or being delivered to a fuel tank of the aircraft.

The UV-visual spectrum light may be passed though the fuel during use of the gas turbine engine. The UV-visual spectrum light may be passed through the fuel within a fuel system of the gas turbine engine.

The UV-visual spectrum light may be passed though the fuel outside of the aircraft during a fuel loading process in which the fuel tank or tanks of the aircraft are loaded with fuel. A UV-vis transmittance sensor may therefore be provided within a re-fueling system of the aircraft.

According to an eighteenth aspect, the present application provides a fuel characteristic determination system for determining one or more fuel characteristics of an aviation fuel suitable for powering a gas turbine engine of an aircraft, the system comprising:

a UV-Vis sensor comprising a UV-visual spectrum light source arranged to pass UV-visual spectrum light through the fuel, the UV-Vis sensor further comprising a transmittance detector arranged to measure a transmittance parameter indicative of the transmittance of the UV-visual spectrum light through the fuel; and a determination module arranged to determine one or more fuel characteristics of the fuel based on the transmittance parameter, wherein the determination module is arranged to communicate the one or more fuel characteristics to a control module of the gas turbine engine or aircraft.

The transmittance parameter may indicate the transmittance of the UV-visual spectrum light as a function of wavelength.

The one or more fuel characteristics determined based on the transmittance parameter may include a hydrocarbon distribution of the fuel.

The one or more fuel characteristics may include any one or more of:

(i) an aromatic hydrocarbon content of the fuel (F);
ii) a percentage of sustainable aviation fuel in the fuel (F); and/or
iii) an indication as to whether the fuel is fossil fuel, e.g. fossil kerosene.

The light source may be arranged to pass light though fuel which is within, sampled from, or being delivered to a fuel tank of the aircraft.

The light source may be arranged to pass light though fuel during use of the gas turbine engine. The light source may be arranged to pass light through fuel while it is within a fuel system of the gas turbine engine.

The light source may be arranged to pass light though fuel which is outside of the aircraft during a fuel loading process in which the fuel tank or tanks of the aircraft are loaded with fuel. The light source may therefore be provided in a re-fueling system of the aircraft.

According to a nineteenth aspect, the present application provides a method of operating an aircraft having a gas turbine engine, the method comprising:

determining one or more fuel characteristics using the method of the seventeenth aspect; and operating the aircraft according to the one or more fuel characteristics.

Operating the aircraft according to the one or more fuel characteristics may comprise:

a) modifying a control parameter of the aircraft, preferably a control parameter of the gas turbine engine, in response to the one or more fuel characteristics; and/or b) providing a fuel having different fuel characteristics during refueling of the aircraft.

According to a twentieth aspect, the present application provides an aircraft comprising the fuel determination system of the eighteenth aspect, the aircraft further comprising a control system arranged to control operation of the aircraft according to the one or more fuel characteristics determined by the fuel characteristic determination system.

According to a twenty first aspect, there is provided a method of determining one or more fuel characteristic of an aviation fuel suitable for powering a gas turbine engine of an aircraft, the method comprising:

determining, during use of the gas turbine engine, one or more contrail parameters related to contrail formation by the gas turbine engine, wherein determining the one or more contrail parameters comprises performing a sensor measurement on a region behind the gas turbine engine in which a contrail is or can be formed; and determining one or more fuel characteristics of the fuel based on the one or more contrail parameters.

The inventors have determined that by performing a sensor measurement sensitive to the formation of contrails on the exhaust plume of a gas turbine engine the characteristics of the fuel being burnt by the gas turbine engine can be determined.

The one or more contrail parameters may include a parameter indicative of the degree of contrail formation taking place. The one or more control parameters may include a parameter indicative of the presence or absence of a contrail produced by the gas turbine engine.

Determining the one or more contrail parameters may comprise measuring electromagnetic radiation reflected and/or re-emitted by a contrail.

Determining the one or more contrail parameters may comprise detecting the presence or absence of a contrail, or the degree to which a contrail is formed, in an image of the region behind the gas turbine engine.

The one or more fuel characteristics may be further determined based on one or more ambient atmospheric condition parameters, each indicative of the ambient atmospheric conditions in which the gas turbine engine is currently operating.

The method may further comprise obtaining the one or more ambient atmospheric conditions from a source of meteorological data providing real-time or expected information on the ambient atmospheric conditions.

The method may further comprise obtaining the one or more ambient atmospheric conditions from a sensor arranged to measure the ambient conditions in the vicinity of the aircraft.

The one or more fuel characteristics may be further determined based on one or more engine or aircraft operating parameters.

The one or more fuel characteristics may be determined based on measuring the value of a varying parameter at which contrail formation begins. The varying parameter may be a varying engine operation parameter and/or a varying ambient condition parameter.

The one or more fuel characteristics determined may include any one or more of: (i) a hydrocarbon distribution of the fuel; (ii) a percentage of sustainable aviation fuel in the fuel; (iii) an aromatic hydrocarbon content of the fuel; and/or (iv) an indication that the fuel is a fossil fuel e.g. kerosene.

According to a twenty second aspect, there is provided a fuel characteristic determination system for determining one or more fuel characteristic of an aviation fuel suitable for powering a gas turbine engine of an aircraft, the system comprising:

a contrail sensor arranged to determine one or more contrail parameters related to contrail formation by the gas turbine engine, the contrail sensor being arranged to perform a sensor measurement on a region behind the gas turbine engine in which a contrail is or can be formed; and a fuel characteristic determination module arranged to determine one or more fuel characteristics of the fuel based on the one or more contrail parameters.

The one or more contrail parameters may include a parameter indicative of the degree of contrail formation taking place. The one or more control parameters may preferably indicate a presence or absence of a contrail produced by the gas turbine engine.

The contrail sensor may be arranged to measure electromagnetic radiation reflected and/or re-emitted by a contrail.

The contrail sensor may be arranged to detect the presence or absence of a contrail, or the degree to which a contrail is formed, in an image of the region behind the gas turbine engine.

The fuel characteristic determination module may be further arranged to determine the one or more fuel characteristics based on one or more ambient atmospheric condition parameters, each indicative of the ambient atmospheric conditions in which the gas turbine engine is currently operating.

The fuel characteristics determination module may be further arranged to obtain the one or more ambient atmospheric conditions from a source of meteorological data providing real-time or expected information on the ambient atmospheric conditions.

The fuel characteristics determination module may be further arranged to obtain the one or more ambient atmospheric conditions from a sensor arranged to measure the ambient conditions in the vicinity of the aircraft.

The fuel characteristic module may be further arranged to determine the one or more fuel characteristics based on one or more engine or aircraft operating parameters. The one or more aircraft and engine parameters may include a temperature of fuel entering a combustor of the gas turbine engine.

The one or more fuel characteristics may be determined based on measuring the value of a varying engine or aircraft operating parameter at which contrail formation begins.

The one or more fuel characteristics determined may include any one or more of: (i) a hydrocarbon distribution of the fuel; (ii) a percentage of sustainable aviation fuel in the fuel; (iii) an aromatic hydrocarbon content of the fuel; and/or (iv) an indication that the fuel is a fossil fuel e.g. kerosene.

According to a twenty third aspect, the present application provides a method of operating an aircraft having a gas turbine engine, the method comprising:
determining one or more fuel characteristics using the method of the twenty first aspect; and
operating the gas turbine engine or aircraft according to the one or more fuel characteristics.

Operating the aircraft according to the one or more fuel characteristics may comprise any one or more of:
i) changing an operating parameter of a heat management system of the gas turbine engine;
ii) changing a fuel temperature of the fuel within the gas turbine engine; and/or
iii) changing a flight characteristic of the aircraft, preferably an altitude of the aircraft, further preferably a cruise altitude.

According to a twenty fourth aspect, the present application provides a method of operating an aircraft having a gas turbine engine, the method comprising:
determining, during use of the gas turbine engine, one or more contrail parameters related to contrail formation by the gas turbine engine, wherein determining the one or more contrail parameters comprises performing a sensor measurement on a region behind the gas turbine engine in which a contrail is or can be formed, and wherein the one or more control parameters are determined during a varying operation of the aircraft and correspond to a value of a varying parameter at which a control begins to form; and
controlling the operating parameter of the aircraft or gas turbine engine according to the one or more contrail parameters.

The varying operation of the aircraft may be a climb phase of operation of the aircraft According to a twenty fifth aspect, the present application provides an aircraft comprising the fuel determination system of the twenty second aspect, the aircraft further comprising a control system arranged to control operation of the aircraft according to the one or more fuel characteristics determined by the fuel determination system.

According to a twenty sixth aspect, the present application provides a method of determining one or more fuel characteristics of an aviation fuel suitable for powering a gas turbine engine of an aircraft, the method comprising:
determining, during use of the gas turbine engine, one or more exhaust content parameters by performing a sensor measurement on an exhaust of the gas turbine engine; and
determining one or more fuel characteristics of the fuel based on the one or more exhaust parameters.

The inventors have determined that characteristics of a fuel being used by a gas turbine engine can be determined by performing measurement on the exhaust gases produced by the engine while it is in use.

The one or more exhaust content parameters may include a parameter indicative of the nvPM content of the exhaust.

Performing the sensor measurement may comprise performing a laser induced incandescence measurement to determine the volume concentration of nvPM in the exhaust.

Performing the sensor measurement may comprise performing a condensation particle count measurement to determine an nvPM number in the exhaust.

The one or more exhaust content parameters may include a parameter indicative of the $SO_2$, $CO_2$ or CO content of the exhaust.

Performing the sensor measurement may comprise performing a non-dispersive Infrared absorption measurement.

The one or more exhaust content parameters may include a sulphate aerosol content of the exhaust.

Performing the sensor measurement may comprise performing an aerosol mass spectrometer measurement to determine the presence of sulphates within the exhaust.

The one or more fuel characteristics may be further determined based on one or more ambient atmospheric condition parameters, each indicative of the ambient atmospheric conditions in which the gas turbine engine is currently operating.

The one or more fuel characteristics may be further determined based on one or more engine operating parameters. The operating parameters may include an engine power setting.

The one more fuel characteristics may be determined based on an exhaust content parameter measured at a first engine operation condition in which emission of the respective substance being measured is greater than at a second engine operation condition.

The one or more fuel characteristics may be determined based on a comparison of exhaust content parameters determined at different engine operation conditions.

The one or more fuel characteristics may include any one of more of: (i) a hydrogen to carbon ratio of the fuel; (ii) a percentage of sustainable aviation fuel in the fuel; (iii) an aromatic hydrocarbon content of the fuel; (iv) a naphthalene content of the fuel; and/or (v) a sulphur content of the fuel.

According to the twenty seventh aspect, the present application provides a fuel characteristic determination system for determining one or more fuel characteristic of an aviation fuel suitable for powering a gas turbine engine of an aircraft, the system comprising:
an exhaust sensor arranged to determine one or more exhaust content parameters, the exhaust sensor being arranged to perform a measurement on an exhaust of the gas turbine engine; and a fuel characteristic determination module arranged to determine one or more fuel characteristics of the fuel based on the one or more exhaust content parameters.

The exhaust sensor may be arranged to determine one or more exhaust content parameters that include a parameter indicative of the nvPM content of the exhaust.

The exhaust sensor may comprise a laser induced incandescence measurement device arranged to determine the volume concentration of nvPM in the exhaust.

The exhaust sensor may comprise a condensation particle count device arranged to determine an nvPM number in the exhaust.

The exhaust sensor may be arranged to determine one or more exhaust content parameters that include a parameter indicative of the $SO_2$, $CO_2$ or CO content of the exhaust. The exhaust sensor may comprise a non-dispersive Infrared absorption measurement device.

The exhaust sensor may be arranged to determine one or more exhaust content parameters that include a sulphate aerosol content of the exhaust. The exhaust sensor may comprise an aerosol mass spectrometer measurement device arranged to measure a sulphate mass in the exhaust.

The one or more fuel characteristics may be further determined by the fuel characteristic determination module based on:

i) one or more ambient atmospheric condition parameters, each indicative of the ambient atmospheric conditions in which the gas turbine engine is currently operating; and/or ii) one or more engine operating parameters, preferably including an engine power setting.

The one or more fuel characteristics may include any one of more of: (i) a hydrogen to carbon ratio of the fuel; (ii) a percentage of sustainable aviation fuel in the fuel; (iii) an aromatic hydrocarbon content of the fuel; (iv) a naphthalene content of the fuel; and/or (v) a sulphur content of the fuel.

According to a twenty eighth aspect, the present application provides a method of operating an aircraft having a gas turbine engine, the method comprising:

determining one or more fuel characteristics using the method of the twenty sixth aspect; and operating the aircraft according to the one or more fuel characteristics.

According to a twenty ninth aspect, the present application provides an aircraft comprising a gas turbine engine and the fuel characteristics determination system of the twenty seventh aspect, the aircraft further comprising a control system arranged to control operation of the aircraft according to the one or more fuel characteristics determined by the fuel characteristic determination system.

According to a thirtieth aspect, the present application provides a method of determining one or more fuel characteristics of an aviation fuel used for powering a gas turbine engine of an aircraft, the method comprising:

determining one or more performance parameters of the gas turbine engine during a first time period of operation of the gas turbine engine;

determining one or more fuel characteristics of the fuel based on the one or more performance parameters.

The inventors have determined that the characteristics of a fuel being used by a gas turbine engine can be determined during use of that engine based on an observation of performance parameters of the engine. By determining one or more performance parameters of the engine, characteristics of the fuel can be determined based on those performance parameters during a different, later period of the engine operation.

The fuel characteristics may be determined during a second later period of operation.

The first period of operation may be a first flight phase, and the second period of operation may be a second flight phase, different from the first.

The first flight phase may be a take-off and/or climb phase, and the second phase flight phase may be a cruise phase or a descent phase.

The one or more performance parameters may include any one or more of:

a) a rotation speed of a fan of the gas turbine engine;
b) a turbine entry temperature of the gas turbine engine; and/or
c) a combustor fuel to air ratio of the gas turbine engine (this may be defined as the ratio of mass of fuel flow to the combustor compared to the core air flow).

Determining the one or more fuel characteristics may comprise comparing each of the one or more determined performance parameters with a reference performance parameter corresponding to operation of the gas turbine engine with a fuel having a known fuel characteristic.

Determining the one or more performance parameters may comprise determining a plurality of different performance parameters. The one or more fuel characteristics may be determined based on the plurality of performance parameters. The plurality of performance parameters may include at least two different performance parameters, and preferably at least three different performance parameters.

The one or more fuel characteristics determined may include any one or more of: (i) a hydrocarbon distribution of the fuel; (ii) a percentage of sustainable aviation fuel in the fuel; (iii) an aromatic hydrocarbon content of the fuel; and/or (iv) an indication that the fuel is a fossil fuel e.g. kerosene.

According to a thirty first aspect, there is provided a method of operating an aircraft having a gas turbine engine, the method comprising:

determining one or more fuel characteristics using the method of the thirtieth aspect;

operating the aircraft according to the one or more fuel characteristics during a or the later the second period of operation of the gas turbine engine.

The aircraft may comprise a plurality of fuel tanks. The aircraft may be only operated according to the one or more fuel characteristics during the second period of operation if fuel is being used from the same fuel tank, or fuel known to have the same fuel characteristics, as during the first period of operation.

Operating the aircraft according to the one or more fuel characteristics may comprises modifying a control parameter of the aircraft, preferably a control parameter of the gas turbine engine, in response to the one or more fuel characteristics.

Operating the aircraft according to the one or more fuel characteristics may comprise any one or more of: i) changing fuel burn parameter of the gas turbine engine; ii) changing an operating parameter of heat management system of the gas turbine engine; iii) adjusting a fuel temperature of the fuel within the gas turbine engine; iv) adjusting a flight characteristic of the aircraft, preferably an altitude of the aircraft, further preferably a cruise altitude.

According to a thirty second aspect, the present application provides a fuel characteristic determination system for determining one or more fuel characteristics of an aviation fuel for powering a gas turbine engine of an aircraft, the system comprising:
  a performance parameter sensor configured to determine one or more performance parameters of the gas turbine engine during a first time period of operation of the gas turbine engine; and
  a fuel characteristic determination module configured to determine one or more fuel characteristics of the fuel based on the one or more performance parameters.

The fuel characteristic determine module may be configured to determine the one or more fuel characteristics during a second later period of operation.

The first period of operation may be a first flight phase, and the second period of operation may be a second flight phase, different from the first.

The first flight phase may be a take-off and/or climb phase, and the second phase flight phase may be a cruise phase or a descent phase.

The one or more performance parameters may include any one or more of:
  a) a rotation speed of a fan of the gas turbine engine;
  b) a turbine entry temperature of the gas turbine engine; and/or
  c) a combustor fuel to air ratio of the gas turbine engine (this may be defined as the ratio of mass of fuel flow to the combustor compared to the core air flow).

The fuel characteristic determination module may be arranged to determine the one or more fuel characteristics by comparing each of the one or more determined performance parameters with a reference performance parameter corresponding to operation of the gas turbine engine with a fuel having a known fuel characteristic.

The fuel characteristic determination module may be arranged to determine the one or more fuel characteristics by obtaining a plurality of different performance parameters from the sensor or additional sensors. The one or more fuel characteristics may be determined based on the plurality of performance parameters. The plurality of performance parameters may include at least two different performance parameters, and preferably at least three different performance parameters.

The one or more fuel characteristics determined may include any one or more of: (i) a hydrocarbon distribution of the fuel; (ii) a percentage of sustainable aviation fuel in the fuel; (iii) an aromatic hydrocarbon content of the fuel; and/or (iv) an indication that the fuel is a fossil fuel e.g. kerosene.

According to a thirty third aspect, the present application provides an aircraft comprising the fuel characteristic determination system of the thirty second aspect, the aircraft further comprising a control system arranged to control operation of the aircraft according to the one or more fuel characteristics determined by the fuel determination system.

According to a thirty fourth aspect, the present application provides a method of generating a maintenance schedule for an aircraft having one or more gas turbine engines powered by an aviation fuel, comprising:
  determining one or more fuel characteristics of the fuel; and
  generating a maintenance schedule according to the one or more fuel characteristics.

The inventors have determined that the characteristics of the fuel that has been used to power the gas turbine have an effect on the operation of the gas turbine engine and the aircraft in general and so may require a change in a maintenance schedule for that aircraft. A maintenance schedule for the aircraft can therefore be advantageously generated based on the characteristics of the fuel with which it has been operated. This may allow the fuel that has actually been used to power the aircraft to be taken into account when performing maintenance.

Generating the maintenance schedule may comprise modifying an existing maintenance schedule for the aircraft according to the determined one or more fuel characteristics.

Generating the maintenance schedule may comprise comparing the one or more determined fuel characteristics to an expected fuel characteristic.

The existing maintenance schedule may be associated with the expected fuel characteristic. Modifying the existing maintenance schedule may be done in response to determining a deviation from the expected fuel characteristic.

Determining the one or more fuel characteristics may comprise making periodic determinations of a fuel characteristic or characteristics.

The one or more fuel characteristics may include any one or more of: (i) a hydrocarbon distribution of the fuel; (ii) a percentage of sustainable aviation fuel in the fuel; (iii) an aromatic hydrocarbon content of the fuel; and/or (iv) an indication that the fuel is a fossil fuel e.g. kerosene.

Determining the one or more fuel characteristics may comprise measuring a change in the properties of a sensor component exposed to the fuel used to power the one or more gas turbine engines.

The one or more fuel characteristics may indicate a threshold level of fuel coking or surface deposit formation has occurred.

The sensor component may be a piezoelectric crystal. Determining the one or more fuel characteristics may comprise measuring a vibration parameter of the piezoelectric crystal.

The sensor component may comprise a seal material and the one or more fuel characteristics may indicate whether a threshold level of swell of the seal material exposed to the fuel has occurred. The seal material may be the same as at least one seal provided in a fuel system of the one or more gas turbine engines. The seal material may be a nitrile seal material.

According to a thirty fifth aspect, the present application provides a method of maintaining an aircraft, comprising:
  generating a maintenance schedule using the method of the thirty fourth aspect; and
  performing maintenance on the aircraft according to the generated maintenance schedule.

According to a thirty sixth aspect, the present application provides a maintenance schedule generation system for generating a maintenance schedule for an aircraft having one or more gas turbine engines, comprising:
  a fuel characteristic determination module configured to determine one or more fuel characteristics of a fuel provided to the one or more gas turbine engines of the aircraft; and
  a maintenance schedule generation module configured to generate a maintenance schedule according to the one or more fuel characteristics.

The generation module may be configured to modify an existing maintenance schedule for the aircraft according to the determined one or more fuel characteristics.

The maintenance schedule generation module may be configured to compare the one or more determined fuel characteristics to an expected fuel characteristic.

The existing maintenance schedule may be associated with the expected fuel characteristic. The maintenance schedule generation module may be configured to modify the existing maintenance schedule in response to determining a deviation from the expected fuel characteristic.

The fuel characteristic determination module may be configured to perform periodic determinations of the one or more fuel characteristics.

The one or more fuel characteristics may include any one or more of: (i) a hydrocarbon distribution of the fuel; (ii) a percentage of sustainable aviation fuel in the fuel; (iii) an aromatic hydrocarbon content of the fuel; and/or (iv) an indication that the fuel is a fossil fuel e.g. kerosene.

The fuel characteristic determination module may be arranged to receive a sensor parameter indicative of a measured change in the properties of a sensor component exposed to the fuel used to power the one or more gas turbine engines, and base the determination of the one or more fuel characteristics on the received sensor parameter.

The one or more fuel characteristics may indicate a threshold level of fuel coking or surface deposit formation has occurred. The sensor component may be a piezoelectric crystal, and determining the one or more fuel characteristics may comprises measuring a vibration parameter of the piezoelectric crystal.

The sensor component may comprise a seal material. The one or more fuel characteristics may indicate whether a threshold level of swell of the seal material exposed to the fuel has occurred. The seal material may be the same as at least one seal provided in a fuel system of the one or more gas turbine engines. The seal material may be a nitrile seal material.

According to a thirty seventh aspect, the present application provides an aircraft having one or more gas turbine engines, the aircraft comprising the maintenance schedule generation system of the thirty sixth aspect.

As used herein, the term "fuel characteristics" refers to inherent fuel properties such as fuel composition, not variable properties such as volume or temperature. Examples of fuel characteristics of a fuel include:
(i) the percentage of sustainable aviation fuel in the fuel;
(ii) the aromatic hydrocarbon content of the fuel;
(iii) the multi-aromatic hydrocarbon content of the fuel;
(iv) the percentage of nitrogen-containing species in the fuel;
(v) the presence or percentage of a trace species or trace element in the fuel (e.g. a trace substance inherently present in the fuel, or one added deliberately to act as a tracer);
(vi) the hydrogen to carbon ratio of the fuel;
(vii) the hydrocarbon distribution of the fuel;
(viii) the level of non-volatile particulate matter (nvPM) emissions on combustion (e.g. on combustion for a given combustor design, at a given operating condition (FAR, T30, combustor mode etc));
(ix) the naphthalene content of the fuel;
(x) the sulphur content of the fuel;
(xi) the cycloparaffin content of the fuel;
(xii) the oxygen content of the fuel;
(xiii) the thermal stability of the fuel (e.g. thermal breakdown temperature);
(xiv) the level of coking of the fuel;
(xv) an indication that the fuel is a fossil fuel, for example fossil kerosene; and
(xvi) one or more properties such as density, viscosity, calorific value, and/or heat capacity.

In any aspect or statement above involving operating an aircraft according to one or more determined fuel characteristics, operating the aircraft may comprise modifying a control parameter of the aircraft, and specifically a control parameter of the gas turbine engine, in response to the one or more fuel characteristics as described anywhere herein. Operating the aircraft may additionally or alternatively comprise providing fuel having a different fuel characteristics, e.g. during refueling as described elsewhere herein.

As noted elsewhere herein, the present disclosure may relate to a gas turbine engine. Such a gas turbine engine may comprise an engine core comprising a turbine, a combustor, a compressor, and a core shaft connecting the turbine to the compressor. Such a gas turbine engine may comprise a fan (having fan blades) located upstream of the engine core. Alternatively, in some examples, the gas turbine engine may comprise a fan located downstream of the engine core. Thus, the gas turbine engine may be an open rotor or a turboprop engine.

Where the gas turbine engine is an open rotor or a turboprop engine, the gas turbine engine may comprise two contra-rotating propeller stages attached to and driven by a free power turbine via a shaft. The propellers may rotate in opposite senses so that one rotates clockwise and the other anti-clockwise around the engine's rotational axis. Alternatively, the gas turbine engine may comprise a propeller stage and a guide vane stage configured downstream of the propeller stage. The guide vane stage may be of variable pitch. Accordingly, high-pressure, intermediate pressure, and free power turbines respectively may drive high and intermediate pressure compressors and propellers by suitable interconnecting shafts. Thus, the propellers may provide the majority of the propulsive thrust.

Where the gas turbine engine is an open rotor or a turboprop engine, one or more of the propeller stages may be driven by a gearbox of the type described.

Arrangements of the present disclosure may be particularly, although not exclusively, beneficial for fans that are driven via a gearbox. Accordingly, the gas turbine engine may comprise a gearbox that receives an input from the core shaft and outputs drive to the fan so as to drive the fan at a lower rotational speed than the core shaft. The input to the gearbox may be directly from the core shaft, or indirectly from the core shaft, for example via a spur shaft and/or gear. The core shaft may rigidly connect the turbine and the compressor, such that the turbine and compressor rotate at the same speed (with the fan rotating at a lower speed).

The gas turbine engine as described and/or claimed herein may have any suitable general architecture. For example, the gas turbine engine may have any desired number of shafts that connect turbines and compressors, for example one, two or three shafts. Purely by way of example, the turbine connected to the core shaft may be a first turbine, the compressor connected to the core shaft may be a first compressor, and the core shaft may be a first core shaft. The engine core may further comprise a second turbine, a second compressor, and a second core shaft connecting the second turbine to the second compressor. The second turbine, second compressor, and second core shaft may be arranged to rotate at a higher rotational speed than the first core shaft.

In such an arrangement, the second compressor may be positioned axially downstream of the first compressor. The second compressor may be arranged to receive (for example directly receive, for example via a generally annular duct) flow from the first compressor.

The gearbox may be arranged to be driven by the core shaft that is configured to rotate (for example in use) at the lowest rotational speed (for example the first core shaft in the example above). For example, the gearbox may be arranged to be driven only by the core shaft that is configured to rotate (for example in use) at the lowest rotational speed (for example only be the first core shaft, and not the second core shaft, in the example above). Alternatively, the gearbox may be arranged to be driven by any one or more shafts, for example the first and/or second shafts in the example above.

The gearbox may be a reduction gearbox (in that the output to the fan is a lower rotational rate than the input from the core shaft). Any type of gearbox may be used. For example, the gearbox may be a "planetary" or "star" gearbox, as described in more detail elsewhere herein. The gearbox may have any desired reduction ratio (defined as the rotational speed of the input shaft divided by the rotational speed of the output shaft), for example greater than 2.5, for example in the range of from 3 to 4.2, or 3.2 to 3.8, for example on the order of or at least 3, 3.1, 3.2, 3.3, 3.4, 3.5, 3.6, 3.7, 3.8, 3.9, 4, 4.1 or 4.2. The gear ratio may be, for example, between any two of the values in the previous sentence. Purely by way of example, the gearbox may be a "star" gearbox having a ratio in the range of from 3.1 or 3.2 to 3.8. In some arrangements, the gear ratio may be outside these ranges.

In any gas turbine engine as described and/or claimed herein, fuel of a given composition or blend is provided to a combustor, which may be provided axially downstream of the fan and compressor(s). For example, the combustor may be directly downstream of (for example at the exit of) the second compressor, where a second compressor is provided. By way of further example, the flow at the exit to the combustor may be provided to the inlet of the second turbine, where a second turbine is provided. The combustor may be provided upstream of the turbine(s).

The or each compressor (for example the first compressor and second compressor as described above) may comprise any number of stages, for example multiple stages. Each stage may comprise a row of rotor blades and a row of stator vanes, which may be variable stator vanes (in that their angle of incidence may be variable). The row of rotor blades and the row of stator vanes may be axially offset from each other.

The or each turbine (for example the first turbine and second turbine as described above) may comprise any number of stages, for example multiple stages. Each stage may comprise a row of rotor blades and a row of stator vanes. The row of rotor blades and the row of stator vanes may be axially offset from each other.

Each fan blade may be defined as having a radial span extending from a root (or hub) at a radially inner gas-washed location, or 0% span position, to a tip at a 100% span position. The ratio of the radius of the fan blade at the hub to the radius of the fan blade at the tip may be less than (or on the order of) any of: 0.4, 0.39, 0.38, 0.37, 0.36, 0.35, 0.34, 0.33, 0.32, 0.31, 0.3, 0.29, 0.28, 0.27, 0.26, or 0.25. The ratio of the radius of the fan blade at the hub to the radius of the fan blade at the tip may be in an inclusive range bounded by any two of the values in the previous sentence (i.e. the values may form upper or lower bounds), for example in the range of from 0.28 to 0.32. These ratios may commonly be referred to as the hub-to-tip ratio. The radius at the hub and the radius at the tip may both be measured at the leading edge (or axially forwardmost) part of the blade. The hub-to-tip ratio refers, of course, to the gas-washed portion of the fan blade, i.e. the portion radially outside any platform.

The radius of the fan may be measured between the engine centreline and the tip of a fan blade at its leading edge. The fan diameter (which may simply be twice the radius of the fan) may be greater than (or on the order of) any of: 220 cm, 230 cm, 240 cm, 250 cm (around 100 inches), 260 cm, 270 cm (around 105 inches), 280 cm (around 110 inches), 290 cm (around 115 inches), 300 cm (around 120 inches), 310 cm, 320 cm (around 125 inches), 330 cm (around 130 inches), 340 cm (around 135 inches), 350 cm, 360 cm (around 140 inches), 370 cm (around 145 inches), 380 cm (around 150 inches) cm, 390 cm (around 155 inches), 400 cm, 410 cm (around 160 inches) or 420 cm (around 165 inches). The fan diameter may be in an inclusive range bounded by any two of the values in the previous sentence (i.e. the values may form upper or lower bounds), for example in the range of from 240 cm to 280 cm or 330 cm to 380 cm.

The rotational speed of the fan may vary in use. Generally, the rotational speed is lower for fans with a higher diameter. Purely by way of non-limitative example, the rotational speed of the fan at cruise conditions may be less than 2500 rpm, for example less than 2300 rpm. Purely by way of further non-limitative example, the rotational speed of the fan at cruise conditions for an engine having a fan diameter in the range of from 220 cm to 300 cm (for example 240 cm to 280 cm or 250 cm to 270 cm) may be in the range of from 1700 rpm to 2500 rpm, for example in the range of from 1800 rpm to 2300 rpm, for example in the range of from 1900 rpm to 2100 rpm. Purely by way of further non-limitative example, the rotational speed of the fan at cruise conditions for an engine having a fan diameter in the range of from 330 cm to 380 cm may be in the range of from 1200 rpm to 2000 rpm, for example in the range of from 1300 rpm to 1800 rpm, for example in the range of from 1400 rpm to 1800 rpm.

In use of the gas turbine engine, the fan (with associated fan blades) rotates about a rotational axis. This rotation results in the tip of the fan blade moving with a velocity $U_{tip}$. The work done by the fan blades 13 on the flow results in an enthalpy rise dH of the flow. A fan tip loading may be defined as $dH/U_{tip}^2$, where dH is the enthalpy rise (for example the 1-D average enthalpy rise) across the fan and $U_{tip}$ is the (translational) velocity of the fan tip, for example at the leading edge of the tip (which may be defined as fan tip radius at leading edge multiplied by angular speed). The fan tip loading at cruise conditions may be greater than (or on the order of) any of: 0.28, 0.29, 0.30, 0.31, 0.32, 0.33, 0.34, 0.35, 0.36, 0.37, 0.38, 0.39 or 0.4 (all values being dimensionless). The fan tip loading may be in an inclusive range bounded by any two of the values in the previous sentence (i.e. the values may form upper or lower bounds), for example in the range of from 0.28 to 0.31, or 0.29 to 0.3.

Gas turbine engines in accordance with the present disclosure may have any desired bypass ratio, where the bypass ratio is defined as the ratio of the mass flow rate of the flow through the bypass duct to the mass flow rate of the flow through the core at cruise conditions. In some arrangements the bypass ratio may be greater than (or on the order of) any of the following: 10, 10.5, 11, 11.5, 12, 12.5, 13, 13.5, 14, 14.5, 15, 15.5, 16, 16.5, 17, 17.5, 18, 18.5, 19, 19.5 or 20. The bypass ratio may be in an inclusive range bounded by any two of the values in the previous sentence (i.e. the values may form upper or lower bounds), for example in the range of form 12 to 16, 13 to 15, or 13 to 14. The bypass duct may be substantially annular. The bypass duct may be radially outside the core engine. The radially outer surface of the bypass duct may be defined by a nacelle and/or a fan case.

The overall pressure ratio of a gas turbine engine as described and/or claimed herein may be defined as the ratio of the stagnation pressure upstream of the fan to the stagnation pressure at the exit of the highest pressure compressor (before entry into the combustor). By way of non-limitative example, the overall pressure ratio of a gas turbine engine as described and/or claimed herein at cruise may be greater than (or on the order of) any of the following: 35, 40, 45, 50, 55, 60, 65, 70, 75. The overall pressure ratio may be in an inclusive range bounded by any two of the values in the previous sentence (i.e. the values may form upper or lower bounds), for example in the range of from 50 to 70.

Specific thrust of an engine may be defined as the net thrust of the engine divided by the total mass flow through the engine. In some examples, specific thrust may depend, for a given thrust condition, upon the specific composition of fuel provided to the combustor. At cruise conditions, the specific thrust of an engine described and/or claimed herein may be less than (or on the order of) any of the following: 110 $Nkg^{-1}s$, 105 $Nkg^{-1}s$, 100 $Nkg^{-1}s$, 95 $Nkg^{-1}s$, 90 $Nkg^{-1}s$, 85 $Nkg^{-1}s$ or 80 $Nkg^{-1}s$. The specific thrust may be in an inclusive range bounded by any two of the values in the previous sentence (i.e. the values may form upper or lower bounds), for example in the range of from 80 $Nkg^{-1}s$ to 100 $Nkg^{-1}s$, or 85 $Nkg^{-1}s$ to 95 $Nkg^{-1}s$. Such engines may be particularly efficient in comparison with conventional gas turbine engines.

A gas turbine engine as described and/or claimed herein may have any desired maximum thrust. Purely by way of non-limitative example, a gas turbine as described and/or claimed herein may be capable of producing a maximum thrust of at least (or on the order of) any of the following: 160 kN, 170 kN, 180 kN, 190 kN, 200 kN, 250 kN, 300 kN, 350 kN, 400 kN, 450 kN, 500 kN, or 550 kN. The maximum thrust may be in an inclusive range bounded by any two of the values in the previous sentence (i.e. the values may form upper or lower bounds). Purely by way of example, a gas turbine as described and/or claimed herein may be capable of producing a maximum thrust in the range of from 330 kN to 420 kN, for example 350 kN to 400 kN. The thrust referred to above may be the maximum net thrust at standard atmospheric conditions at sea level plus 15 degrees C. (ambient pressure 101.3 kPa, temperature 30 degrees C.), with the engine static.

In use, the temperature of the flow at the entry to the high pressure turbine may be particularly high. This temperature, which may be referred to as TET, may be measured at the exit to the combustor, for example immediately upstream of the first turbine vane, which itself may be referred to as a nozzle guide vane. In some examples, TET may depend, for a given thrust condition, upon the specific composition of fuel provided to the combustor. At cruise, the TET may be at least (or on the order of) any of the following: 1400K, 1450K, 1500K, 1550K, 1600K or 1650K. The TET at cruise may be in an inclusive range bounded by any two of the values in the previous sentence (i.e. the values may form upper or lower bounds). The maximum TET in use of the engine may be, for example, at least (or on the order of) any of the following: 1700K, 1750K, 1800K, 1850K, 1900K, 1950K or 2000K. The maximum TET may be in an inclusive range bounded by any two of the values in the previous sentence (i.e. the values may form upper or lower bounds), for example in the range of from 1800K to 1950K. The maximum TET may occur, for example, at a high thrust condition, for example at a maximum take-off (MTO) condition.

A fan blade and/or aerofoil portion of a fan blade described and/or claimed herein may be manufactured from any suitable material or combination of materials. For example at least a part of the fan blade and/or aerofoil may be manufactured at least in part from a composite, for example a metal matrix composite and/or an organic matrix composite, such as carbon fibre. By way of further example at least a part of the fan blade and/or aerofoil may be manufactured at least in part from a metal, such as a titanium based metal or an aluminium based material (such as an aluminium-lithium alloy) or a steel based material. The fan blade may comprise at least two regions manufactured using different materials. For example, the fan blade may have a protective leading edge, which may be manufactured using a material that is better able to resist impact (for example from birds, ice or other material) than the rest of the blade. Such a leading edge may, for example, be manufactured using titanium or a titanium-based alloy. Thus, purely by way of example, the fan blade may have a carbon-fibre or aluminium based body (such as an aluminium lithium alloy) with a titanium leading edge.

A fan as described and/or claimed herein may comprise a central portion, from which the fan blades may extend, for example in a radial direction. The fan blades may be attached to the central portion in any desired manner. For example, each fan blade may comprise a fixture which may engage a corresponding slot in the hub (or disc). Purely by way of example, such a fixture may be in the form of a dovetail that may slot into and/or engage a corresponding slot in the hub/disc in order to fix the fan blade to the hub/disc. By way of further example, the fan blades maybe formed integrally with a central portion. Such an arrangement may be referred to as a bladed disc or a bladed ring. Any suitable method may be used to manufacture such a bladed disc or bladed ring. For example, at least a part of the fan blades may be machined from a block and/or at least part of the fan blades may be attached to the hub/disc by welding, such as linear friction welding.

The gas turbine engines described and/or claimed herein may or may not be provided with a variable area nozzle (VAN). Such a variable area nozzle may allow the exit area of the bypass duct to be varied in use. The general principles of the present disclosure may apply to engines with or without a VAN.

The fan of a gas turbine as described and/or claimed herein may have any desired number of fan blades, for example 14, 16, 18, 20, 22, 24 or 26 fan blades.

As used herein, the terms idle, taxi, take-off, climb, cruise, descent, approach, and landing have the conventional meaning and would be readily understood by the skilled person. Thus, for a given gas turbine engine for an aircraft, the skilled person would immediately recognise each term to refer to an operating phase of the engine within a given mission of an aircraft to which the gas turbine engine is designed to be attached.

In this regard, ground idle may refer to an operating phase of the engine where the aircraft is stationary and in contact with the ground, but where there is a requirement for the engine to be running. During idle, the engine may be producing between 3% and 9% of the available thrust of the engine. In further examples, the engine may be producing between 5% and 8% of available thrust. In yet further examples, the engine may be producing between 6% and 7% of available thrust. Taxi may refer to an operating phase of the engine where the aircraft is being propelled along the ground by the thrust produced by the engine. During taxi, the engine may be producing between 5% and 15% of available thrust. In further examples, the engine may be producing between 6% and 12% of available thrust. In yet further examples, the engine may be producing between 7% and 10% of available thrust. Take-off may refer to an operating phase of the engine where the aircraft is being propelled by the thrust produced by the engine. At an initial stage within the take-off phase, the aircraft may be propelled whilst the aircraft is in contact with the ground. At a later stage within the take-off phase, the aircraft may be propelled whilst the aircraft is not in contact with the ground. During take-off, the engine may be producing between 90% and 100% of available thrust. In further examples, the engine may be producing between 95% and 100% of available thrust. In yet further examples, the engine may be producing 100% of available thrust.

Climb may refer to an operating phase of the engine where the aircraft is being propelled by the thrust produced by the engine. During climb, the engine may be producing between 75% and 100% of available thrust. In further examples, the engine may be producing between 80% and 95% of available thrust. In yet further examples, the engine may be producing between 85% and 90% of available thrust. In this regard, climb may refer to an operating phase within an aircraft flight cycle between take-off and the arrival at cruise conditions. Additionally or alternatively, climb may refer to a nominal point in an aircraft flight cycle between take-off and landing, where a relative increase in altitude is required, which may require an additional thrust demand of the engine.

As used herein, cruise conditions have the conventional meaning and would be readily understood by the skilled person. Thus, for a given gas turbine engine for an aircraft, the skilled person would immediately recognise cruise conditions to mean the operating point of the engine at mid-cruise of a given mission (which may be referred to in the industry as the "economic mission") of an aircraft to which the gas turbine engine is designed to be attached. In this regard, mid-cruise is the point in an aircraft flight cycle at which 50% of the total fuel that is burned between top of climb and start of descent has been burned (which may be approximated by the midpoint—in terms of time and/or distance—between top of climb and start of descent. Cruise conditions thus define an operating point of, the gas turbine engine that provides a thrust that would ensure steady state operation (i.e. maintaining a constant altitude and constant Mach Number) at mid-cruise of an aircraft to which it is designed to be attached, taking into account the number of engines provided to that aircraft. For example where an engine is designed to be attached to an aircraft that has two engines of the same type, at cruise conditions the engine provides half of the total thrust that would be required for steady state operation of that aircraft at mid-cruise.

In other words, for a given gas turbine engine for an aircraft, cruise conditions are defined as the operating point of the engine that provides a specified thrust (required to provide—in combination with any other engines on the aircraft—steady state operation of the aircraft to which it is designed to be attached at a given mid-cruise Mach Number) at the mid-cruise atmospheric conditions (defined by the International Standard Atmosphere according to ISO 2533 at the mid-cruise altitude). For any given gas turbine engine for an aircraft, the mid-cruise thrust, atmospheric conditions and Mach Number are known, and thus the operating point of the engine at cruise conditions is clearly defined.

Purely by way of example, the forward speed at the cruise condition may be any point in the range of from Mach 0.7 to 0.9, for example 0.75 to 0.85, for example 0.76 to 0.84, for example 0.77 to 0.83, for example 0.78 to 0.82, for example 0.79 to 0.81, for example on the order of Mach 0.8, on the order of Mach 0.85 or in the range of from 0.8 to 0.85. Any single speed within these ranges may be part of the cruise condition. For some aircraft, the cruise conditions may be outside these ranges, for example below Mach 0.7 or above Mach 0.9.

Purely by way of example, the cruise conditions may correspond to standard atmospheric conditions (according to the International Standard Atmosphere, ISA) at an altitude that is in the range of from 10000m to 15000m, for example in the range of from 10000m to 12000m, for example in the range of from 10400m to 11600m (around 38000 ft), for example in the range of from 10500m to 11500m, for example in the range of from 10600m to 11400m, for example in the range of from 10700m (around 35000 ft) to 11300m, for example in the range of from 10800m to 11200m, for example in the range of from 10900m to 11100m, for example on the order of 11000m. The cruise conditions may correspond to standard atmospheric conditions at any given altitude in these ranges.

Purely by way of example, the cruise conditions may correspond to an operating point of the engine that provides a known required thrust level (for example a value in the range of from 30 kN to 35 kN) at a forward Mach number of 0.8 and standard atmospheric conditions (according to the International Standard Atmosphere) at an altitude of 38000 ft (11582m). Purely by way of further example, the cruise conditions may correspond to an operating point of the engine that provides a known required thrust level (for example a value in the range of from 50 kN to 65 kN) at a forward Mach number of 0.85 and standard atmospheric conditions (according to the International Standard Atmosphere) at an altitude of 35000 ft (10668m).

In use, a gas turbine engine described and/or claimed herein may operate at the cruise conditions defined elsewhere herein. Such cruise conditions may be determined by the cruise conditions (for example the mid-cruise conditions) of an aircraft to which at least one (for example 2 or 4) gas turbine engine may be mounted in order to provide propulsive thrust.

Furthermore, the skilled person would immediately recognise either or both of descent and approach to refer to an operating phase within an aircraft flight cycle between cruise and landing of the aircraft. During either or both of descent and approach, the engine may be producing between 20% and 50% of available thrust. In further examples, the engine may be producing between 25% and 40% of available thrust. In yet further examples, the engine may be producing between 30% and 35% of available thrust. Additionally or alternatively, descent may refer to a nominal point in an aircraft flight cycle between take-off and landing, where a relative decrease in altitude is required, and which may require a reduced thrust demand of the engine.

According to an aspect, there is provided an aircraft comprising a gas turbine engine as described and/or claimed herein. The aircraft according to this aspect is the aircraft for which the gas turbine engine has been designed to be attached. Accordingly, the cruise conditions according to this aspect correspond to the mid-cruise of the aircraft, as defined elsewhere herein.

According to an aspect, there is provided a method of operating a gas turbine engine as described and/or claimed herein. The operation may be at the cruise conditions as defined elsewhere herein (for example in terms of the thrust, atmospheric conditions and Mach Number).

According to an aspect, there is provided a method of operating an aircraft comprising a gas turbine engine as described and/or claimed herein. The operation according to this aspect may include (or may be) operation at the mid-cruise of the aircraft, as defined elsewhere herein.

The skilled person will appreciate that except where mutually exclusive, a feature or parameter described in relation to any one of the above aspects may be applied to any other aspect. Furthermore, except where mutually exclusive, any feature or parameter described herein may be applied to any aspect and/or combined with any other feature or parameter described herein.

BRIEF DESCRIPTION OF THE DRAWINGS

Embodiments will now be described by way of example only, with reference to the Figures, in which.

DETAILED DESCRIPTION OF THE DISCLOSURE

Figure 1:
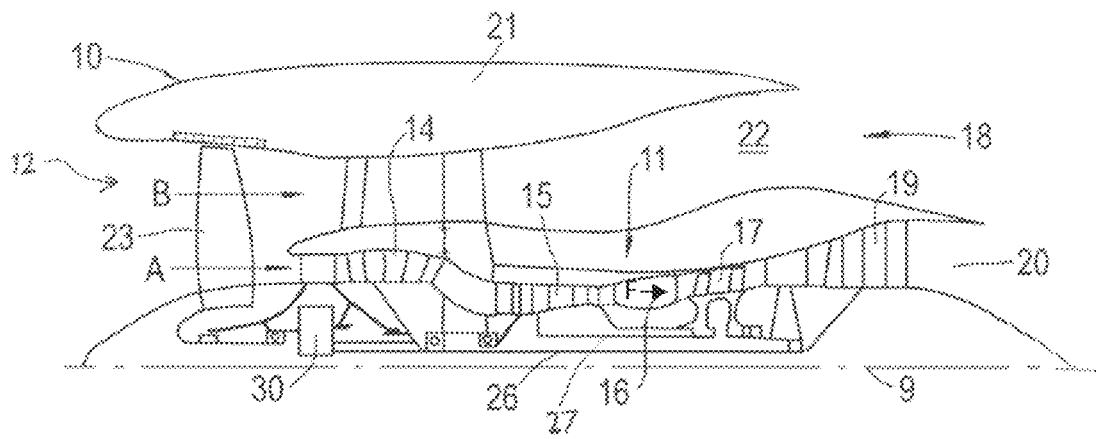
FIG. 1 is a sectional side view of a gas turbine engine.

FIG. 1 illustrates a gas turbine engine 10 having a principal rotational axis 9. The engine 10 comprises an air intake 12 and a propulsive fan 23 that generates two airflows: a core airflow A and a bypass airflow B. The gas turbine engine 10 comprises a core 11 that receives the core airflow A. The engine core 11 comprises, in axial flow series, a low pressure compressor 14, a high-pressure compressor 15, combustion equipment 16, a high-pressure turbine 17, a low pressure turbine 19 and a core exhaust nozzle 20. A nacelle 21 surrounds the gas turbine engine 10 and defines a bypass duct 22 and a bypass exhaust nozzle 18. The bypass airflow B flows through the bypass duct 22.

The fan 23 is attached to and driven by the low pressure turbine 19 via a shaft 26 and an epicyclic gearbox 30.

In use, the core airflow A is accelerated and compressed by the low pressure compressor 14 and directed into the high pressure compressor 15 where further compression takes place. The compressed air exhausted from the high pressure compressor 15 is directed into the combustion equipment 16 where it is mixed with fuel F and the mixture is combusted. The resultant hot combustion products then expand through, and thereby drive, the high pressure and low pressure turbines 17, 19 before being exhausted through the nozzle 20 to provide some propulsive thrust. The high pressure turbine 17 drives the high pressure compressor 15 by a suitable interconnecting shaft 27. The fan 23 generally provides the majority of the propulsive thrust. The epicyclic gearbox 30 is a reduction gearbox.

Figure 2:
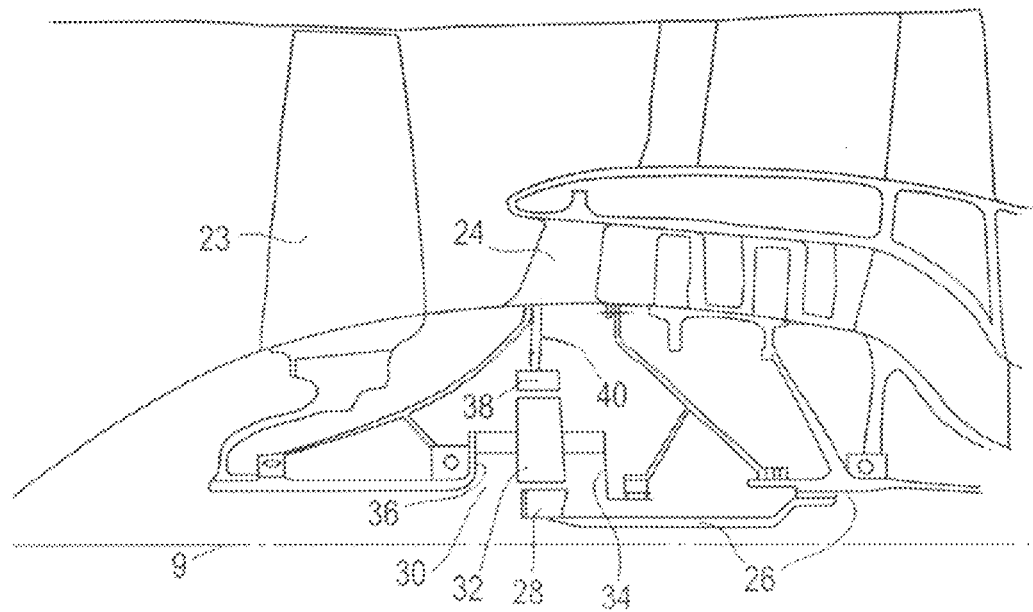
FIG. 2 is a close up sectional side view of an upstream portion of a gas turbine engine.

An exemplary arrangement for a geared fan gas turbine engine 10 is shown in FIG. 2. The low pressure turbine 19 (see FIG. 1) drives the shaft 26, which is coupled to a sun wheel, or sun gear, 28 of the epicyclic gear arrangement 30. Radially outwardly of the sun gear 28 and intermeshing therewith is a plurality of planet gears 32 that are coupled together by a planet carrier 34. The planet carrier 34 constrains the planet gears 32 to precess around the sun gear 28 in synchronicity whilst enabling each planet gear 32 to rotate about its own axis. The planet carrier 34 is coupled via linkages 36 to the fan 23 in order to drive its rotation about the engine axis 9. Radially outwardly of the planet gears 32 and intermeshing therewith is an annulus or ring gear 38 that is coupled, via linkages 40, to a stationary supporting structure 24.

Note that the terms "low pressure turbine" and "low pressure compressor" as used herein may be taken to mean the lowest pressure turbine stages and lowest pressure compressor stages (i.e. not including the fan 23) respectively and/or the turbine and compressor stages that are connected together by the interconnecting shaft 26 with the lowest rotational speed in the engine (i.e. not including the gearbox output shaft that drives the fan 23). In some literature, the "low pressure turbine" and "low pressure compressor" referred to herein may alternatively be known as the "intermediate pressure turbine" and "intermediate pressure compressor". Where such alternative nomenclature is used, the fan 23 may be referred to as a first, or lowest pressure, compression stage.

Figure 3:
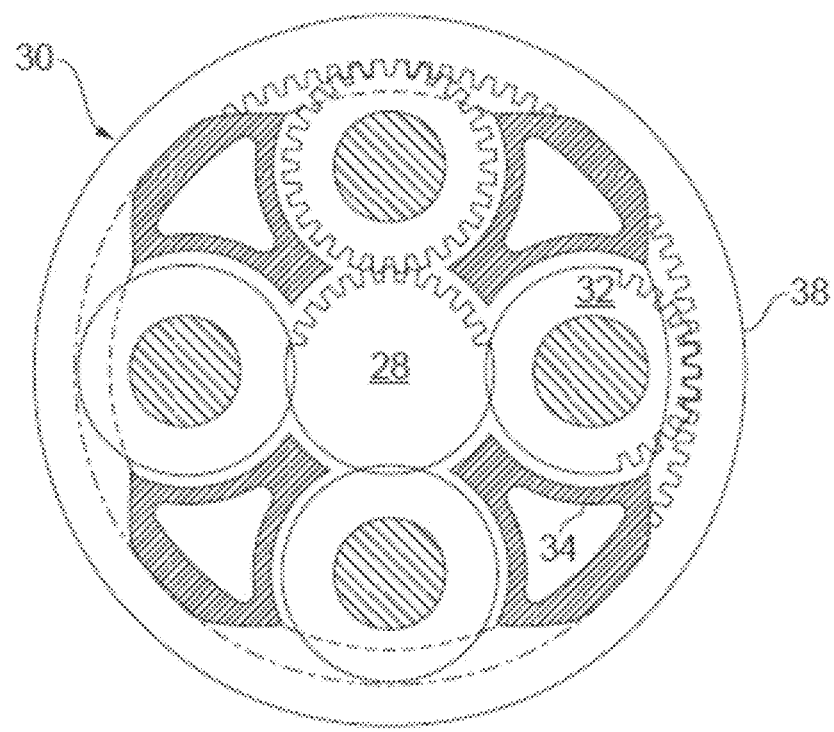
FIG. 3 is a partially cut-away view of a gearbox for a gas turbine engine.

The epicyclic gearbox 30 is shown by way of example in greater detail in FIG. 3. Each of the sun gear 28, planet gears 32 and ring gear 38 comprise teeth about their periphery to intermesh with the other gears. However, for clarity only exemplary portions of the teeth are illustrated in FIG. 3. There are four planet gears 32 illustrated, although it will be apparent to the skilled reader that more or fewer planet gears 32 may be provided within the scope of the claimed invention. Practical applications of a planetary epicyclic gearbox 30 generally comprise at least three planet gears 32.

The epicyclic gearbox 30 illustrated by way of example in FIGS. 2 and 3 is of the planetary type, in that the planet carrier 34 is coupled to an output shaft via linkages 36, with the ring gear 38 fixed. However, any other suitable type of epicyclic gearbox 30 may be used. By way of further example, the epicyclic gearbox 30 may be a star arrangement, in which the planet carrier 34 is held fixed, with the ring (or annulus) gear 38 allowed to rotate. In such an arrangement the fan 23 is driven by the ring gear 38. By way of further alternative example, the gearbox 30 may be a differential gearbox in which the ring gear 38 and the planet carrier 34 are both allowed to rotate.

It will be appreciated that the arrangement shown in FIGS. 2 and 3 is by way of example only, and various alternatives are within the scope of the present disclosure. Purely by way of example, any suitable arrangement may be used for locating the gearbox 30 in the engine 10 and/or for connecting the gearbox 30 to the engine 10. By way of further example, the connections (such as the linkages 36, 40 in the FIG. 2 example) between the gearbox 30 and other parts of the engine 10 (such as the input shaft 26, the output shaft and the fixed structure 24) may have any desired degree of stiffness or flexibility. By way of further example, any suitable arrangement of the bearings between rotating and stationary parts of the engine (for example between the input and output shafts from the gearbox and the fixed structures, such as the gearbox casing) may be used, and the disclosure is not limited to the exemplary arrangement of FIG. 2. For example, where the gearbox 30 has a star arrangement (described above), the skilled person would readily understand that the arrangement of output and support linkages and bearing locations would typically be different to that shown by way of example in FIG. 2.

Accordingly, the present disclosure extends to a gas turbine engine having any arrangement of gearbox styles (for example star or planetary), support structures, input and output shaft arrangement, and bearing locations.

Optionally, the gearbox may drive additional and/or alternative components (e.g. the intermediate pressure compressor and/or a booster compressor).

Other gas turbine engines to which the present disclosure may be applied may have alternative configurations. For example, such engines may have an alternative number of compressors and/or turbines and/or an alternative number of interconnecting shafts. By way of further example, the gas turbine engine shown in FIG. 1 has a split flow nozzle 18, 20 meaning that the flow through the bypass duct 22 has its own nozzle 18 that is separate to and radially outside the core engine nozzle 20. However, this is not limiting, and any aspect of the present disclosure may also apply to engines in which the flow through the bypass duct 22 and the flow through the core 11 are mixed, or combined, before (or upstream of) a single nozzle, which may be referred to as a mixed flow nozzle. One or both nozzles (whether mixed or split flow) may have a fixed or variable area.

Whilst the described example relates to a turbofan engine, the disclosure may apply, for example, to any type of gas turbine engine, such as an open rotor (in which the fan stage is not surrounded by a nacelle) or turboprop engine, for example. In some arrangements, the gas turbine engine 10 may not comprise a gearbox 30.

The geometry of the gas turbine engine 10, and components thereof, is defined by a conventional axis system, comprising an axial direction (which is aligned with the rotational axis 9), a radial direction (in the bottom-to-top direction in FIG. 1), and a circumferential direction (perpendicular to the page in the FIG. 1 view). The axial, radial and circumferential directions are mutually perpendicular.

The fuel F provided to the combustion equipment 16 may comprise a fossil-based hydrocarbon fuel, such as Kerosene. Thus, the fuel F may comprise molecules from one or more of the chemical families of n-alkanes, iso-alkanes, cycloalkanes, and aromatics. Additionally or alternatively, the fuel F may comprise renewable hydrocarbons produced from biological or non-biological resources, otherwise known as sustainable aviation fuel (SAF). In each of the provided examples, the fuel F may comprise one or more trace elements including, for example, sulphur, nitrogen, oxygen, inorganics, and metals.

Functional performance of a given composition, or blend of fuel for use in a given mission, may be defined, at least in part, by the ability of the fuel to service the Brayton cycle of the gas turbine engine 10. Parameters defining functional performance may include, for example, specific energy; energy density; thermal stability; and, emissions including particulate matter. A relatively higher specific energy (i.e. energy per unit mass), expressed as MJ/kg, may at least partially reduce take-off weight, thus potentially providing a relative improvement in fuel efficiency. A relatively higher energy density (i.e. energy per unit volume), expressed as MJ/L, may at least partially reduce take-off fuel volume, which may be particularly important for volume-limited missions or military operations involving refueling. A relatively higher thermal stability (i.e. inhibition of fuel to degrade or coke under thermal stress) may permit the fuel to sustain elevated temperatures in the engine and fuel injectors, thus potentially providing relative improvements in combustion efficiency. Reduced emissions, including particulate matter, may permit reduced contrail formation, whilst reducing the environmental impact of a given mission. Other properties of the fuel may also be key to functional performance. For example, a relatively lower freeze point (° C.) may allow long-range missions to optimise flight profiles; minimum aromatic concentrations (%) may ensure sufficient swelling of certain materials used in the construction of o-rings and seals that have been previously exposed to fuels with high aromatic contents; and, a maximum surface tension (mN/m) may ensure sufficient spray break-up and atomisation of the fuel.

The ratio of the number of hydrogen atoms to the number of carbon atoms in a molecule may influence the specific energy of a given composition, or blend of fuel. Fuels with higher ratios of hydrogen atoms to carbon atoms may have higher specific energies in the absence of bond strain. For example, fossil-based hydrocarbon fuels may comprise molecules with approximately 7 to 18 carbons, with a significant portion of a given composition stemming from molecules with 9 to 15 carbons, with an average of 12 carbons.

ASTM International (ASTM) D7566, Standard Specification for Aviation Turbine Fuels Containing Synthesized Hydrocarbons (ASTM 2019c) approves a number of sustainable aviation fuel blends comprising between 10% and 50% sustainable aviation fuel (the remainder comprising one or more fossil-based hydrocarbon fuels, such as Kerosene), with further compositions awaiting approval. However, there is an anticipation in the aviation industry that sustainable aviation fuel blends comprising up to (and including) 100% sustainable aviation fuel (SAF) will be eventually approved for use.

Sustainable aviation fuels may comprise one or more of n-alkanes, iso-alkanes, cyclo-alkanes, and aromatics, and may be produced, for example, from one or more of synthesis gas (syngas); lipids (e.g. fats, oils, and greases); sugars; and alcohols. Thus, sustainable aviation fuels may comprise either or both of a lower aromatic and sulphur content, relative to fossil-based hydrocarbon fuels. Additionally or alternatively, sustainable aviation fuels may comprise either or both of a higher iso-alkane and cyclo-alkane content, relative to fossil-based hydrocarbon fuels. Thus, in some examples, sustainable aviation fuels may comprise either or both of a density of between 90% and 98% that of kerosene and a calorific value of between 101% and 105% that of kerosene.

Owing at least in part to the molecular structure of sustainable aviation fuels, sustainable aviation fuels may provide benefits including, for example, one or more of a higher energy density; higher specific energy; higher specific heat capacity; higher thermal stability; higher lubricity; lower viscosity; lower surface tension; lower freeze point; lower soot emissions; and, lower $CO_2$ emissions, relative to fossil-based hydrocarbon fuels (e.g. when combusted in the combustion equipment 16). Accordingly, relative to fossil-based hydrocarbon fuels, such as Kerosene, sustainable aviation fuels may lead to either or both of a relative decrease in specific fuel consumption, and a relative decrease in maintenance costs.

Figure 4:
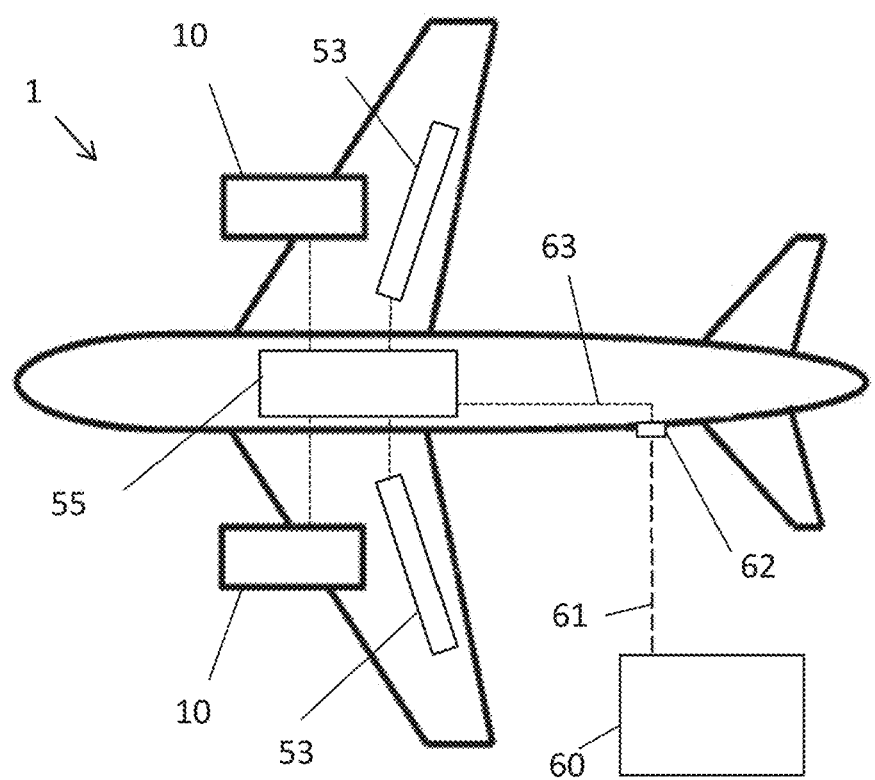
FIG. 4 is a schematic view of an aircraft including a fuel supply system.

An aircraft 1 comprising two gas turbine engines 10 according to any of the examples described herein is illustrated in FIG. 4. In this example, the aircraft 1 comprises two gas turbine engines 10, but in other examples it may comprise one or more gas turbine engines. The aircraft 1 further comprises an aircraft fuel supply system located on board the aircraft which is suitable for suppling fuel F to each of the gas turbine engines 10 to be burnt in the engine combustion equipment 16 as described above. The aircraft fuel supply system is arranged to provide fuel to an engine fuel system provided on each of the gas turbine engines 10. The engine fuel system and aircraft fuel supply system together form the (overall) fuel system of the aircraft 1 in which fuel is stored, delivered to the engine, and combusted. The fuel system of the aircraft includes any component which may store fuel, or through which fuel flows during use or during refueling.

The aircraft fuel supply system comprises an aircraft fuel source arranged to contain a fuel F to be supplied to the gas turbine engines. For the purposes of the present application the term "fuel source" is understood to mean either 1) a single fuel tank or 2) a plurality of fuel tanks which may or may not be fluidly interconnected. In the present example, the fuel source comprises a plurality of wing fuel tanks 53, where at least one wing fuel tank is located in the port wing and at least one wing fuel tank is located in the starboard wing, and a centre fuel tank 55 located primarily in the fuselage of the aircraft 1. Each of the centre fuel tank 55 and the wing fuel tanks 53 may comprise a plurality of fluidly interconnected fuel tanks not shown in the Figures.

For balancing purposes, one or more fuel tanks 53 in the port wing may be fluidly connected to one or more fuel tanks 53 in the starboard wing as shown by the dotted lines in FIG. 4. This may be done either via the centre fuel tank 55, or bypassing the centre fuel tank(s), or both (for maximum flexibility and safety). In yet other examples, the fuel source may comprise a separate trim fuel tank in order to balance the aircraft during flight (not shown in the figures).

FIG. 4 illustrates fuel being loaded onto the aircraft 1 from a fuel storage vessel 60. The fuel storage vessel 60 may be carried by a fuel supply vehicle (e.g. fuel tanker) or may be a fixed storage vessel from which the aircraft 1 can be refueled. The aircraft fuel system comprises a fuel line connection port 62 which is coupled to a fuel loading line 61 during refueling. The fuel loading line 61 may comprise a fuel pipe of known design. The fuel line connection port 62 is fluidly coupled with the fuel tanks 53, 55 of the aircraft 1 by a fuel transmission line or lines 63 on board the aircraft so that fuel received via the fuel loading line 61 is transferred and stored within the fuel tanks 53, 55. The fuel loading line 61 and fuel transmission line 63 may together form a fuel supply line used to supply fuel to the fuel tanks 53, 55 on board the aircraft 1 from the fuel storage vessel 60. In some examples, the fuel transmission line(s) 63 may not be present, with the fuel instead delivered directly from a fuel line connection port for each fuel tank (or set of interconnected fuel tanks). The fuel loading line 61 and the storage vessel (and any associated control or pump components) may form a refueling system for the aircraft.

Fuel Characteristics

As used herein, the term "fuel characteristics" refers to inherent fuel properties such as fuel composition, not variable properties such as volume or temperature. Examples of fuel characteristics of a fuel include:

(i) the percentage of sustainable aviation fuel in the fuel;
(ii) the aromatic hydrocarbon content of the fuel;
(iii) the multi-aromatic hydrocarbon content of the fuel;
(iv) the percentage of nitrogen-containing species in the fuel;
(v) the presence or percentage of a trace species or trace element in the fuel (e.g. a trace substance inherently present in the fuel, or one added deliberately to act as a tracer);
(vi) the hydrogen to carbon ratio of the fuel;
(vii) the hydrocarbon distribution of the fuel;
(viii) the level of non-volatile particulate matter (nvPM) emissions on combustion (e.g. on combustion for a given combustor design, at a given operating condition (FAR, T30, combustor mode etc));
(ix) the naphthalene content of the fuel;
(x) the sulphur content of the fuel;

(xi) the cycloparaffin content of the fuel;
(xii) the oxygen content of the fuel;
(xiii) the thermal stability of the fuel (e.g. thermal breakdown temperature);
(xiv) the level of coking of the fuel;
(xv) an indication that the fuel is a fossil fuel, for example fossil kerosene; and
(xvi) one or more properties such as density, viscosity, calorific value, and/or heat capacity.

As used herein, T30, T40 and T41, and any other numbered pressures and temperatures, are defined using the station numbering listed in standard SAE AS755, in particular:

T30=High Pressure Compressor (HPC) Outlet Total Temperature;
T40=Combustion Exit Total Temperature;
T41=High Pressure Turbine (HPT) Rotor Entry Total Temperature.

Figure 5:
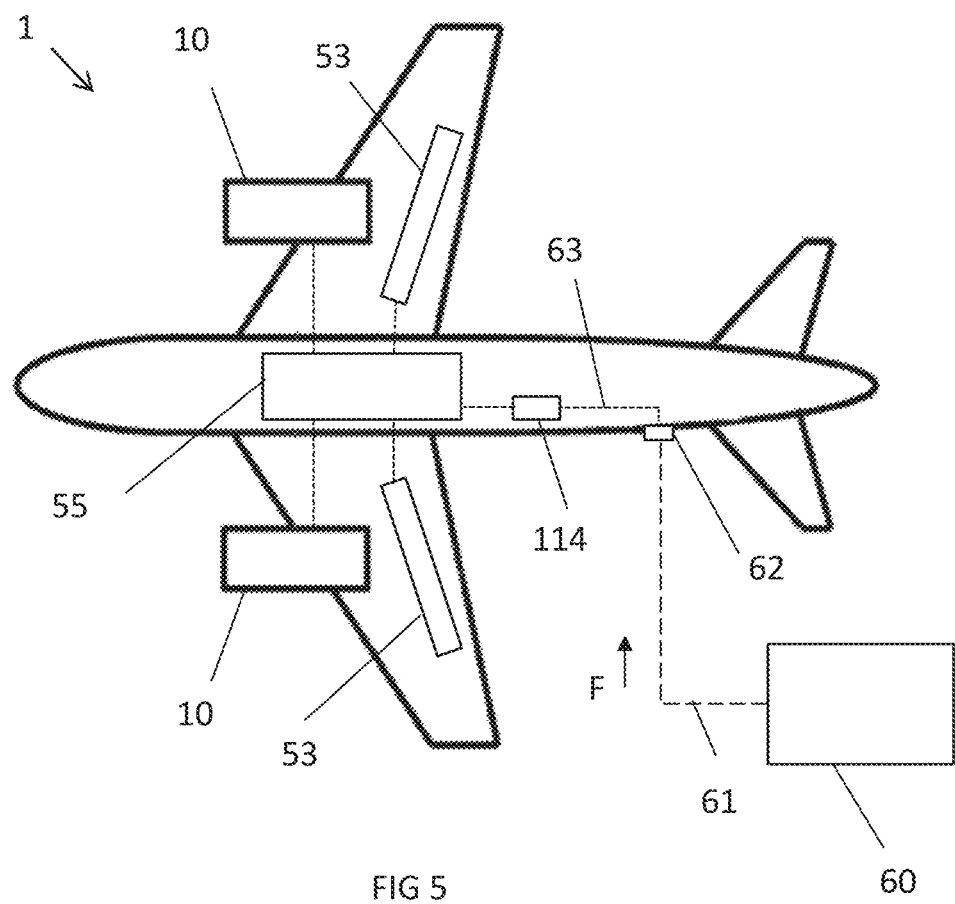
FIG. 5 is a schematic view of an aircraft including a fuel characteristic determination system.

Piezoelectric Sensor
Fuel Characteristic Determination During Refueling Using Piezoelectric Sensor:

Referring to FIG. 5, an example of a fuel characteristic determination system 114 is illustrated, located on board the aircraft 1. The fuel characteristic determination system 114 in this example is arranged to determine one or more fuel characteristics of fuel F being loaded onto the aircraft 1, those characteristics being any of those described or claimed herein.

Figure 6:
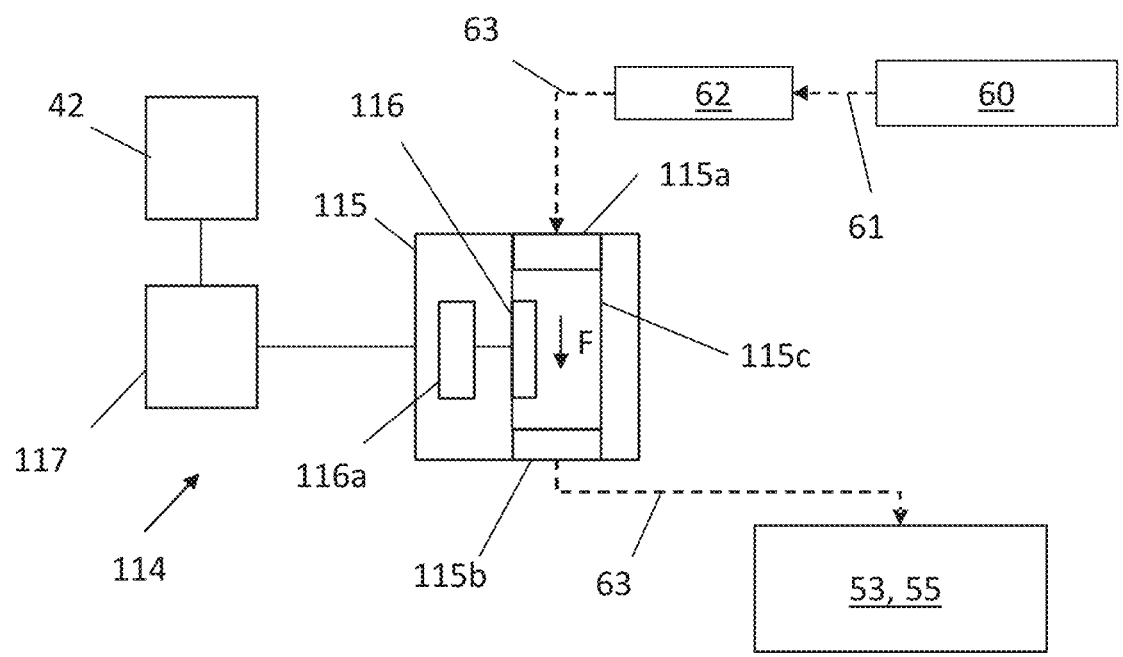
FIG. 6 is a close-up schematic view of the fuel characteristic determination system of FIG. 5.

Further details of the fuel characteristic determination system 114 are illustrated in FIG. 6. The fuel characteristic determination system 114 generally comprises a sensor 115 which comprises a piezoelectric crystal 116. The piezoelectric crystal 116 is arranged so that it is exposed to fuel F which is flowing through the sensor 115. In the present example, fuel being loaded onto the aircraft 1 is passed through the sensor 115 so that the piezoelectric crystal 116 is exposed to the fuel. The sensor 115 comprises a fuel inlet 115a and a fuel outlet 115b, and a fuel conduit 115c arranged in fluid communication between them. In the present example, the sensor 115 is located on board the aircraft 1 and is arranged to receive fuel F flowing through the fuel transmission line 63 i.e. fuel flowing from the fuel line connection port 62 to the fuel tanks 53, 55. In the present example, the sensor 115 is arranged such that all of the fuel flowing through the transmission line 63 is input to the sensor inlet 115a, flows through the fuel conduit 115c, and is output via the fuel outlet 115b to continue to the fuel tanks (i.e. the sensor is connected in series between the fuel line connection port 62 and the fuel tanks). In other examples, the sensor 115 may be connected in parallel such that only some of the fuel is redirected from the transmission line 63, flows through the sensor, and then is returned to the fuel transmission line 63 or to the fuel tanks.

The sensor 115 is arranged to measure a vibration parameter of the piezoelectric crystal 116. The vibration parameter may be a vibrational mode of the piezoelectric crystal such as a resonant frequency at which the crystal oscillates. In the present example, the sensor comprises a resonant frequency measurement module 116a arranged to measure a resonant frequency of the crystal by applying voltage to an electrode near or on the crystal 116. This causes the crystal 116 to distort in an electric field created by the voltage. Once the field is removed, the piezoelectric crystal 116 generates an electric field as it returns to its previous shape, generating a voltage. This results in the crystal behaving like an RLC circuit, composed of an inductor, capacitor and resistor with a corresponding resonant frequency as would be known in the art.

The inventors have determined that the resonant frequency of the crystal 116 varies according to deposits formed on its surface by the fuel to which it is exposed. By measuring the resonant frequency or other vibration parameter (or change thereof over time) the amount of surface deposition on the crystal surface can be determined. In the present example, the fuel characteristic determination system 114 further comprises a fuel characteristic determination module 117 arranged to determine one or more fuel characteristics of the fuel based on the vibration parameter. The fuel characteristic determination module 117 receives the vibration parameter from the sensor 115 such that the one or more fuel characteristics can be calculated.

In some examples, the surface deposits may be cleared between different uses of the fuel characteristic determination system, e.g. by the crystal being exposed to a different type of fuel that clears any deposits from the surface of the crystal. In other examples, the sensor may include means for cleaning the surface of the piezoelectric crystal, or means to allow replacement of the crystal, between uses (e.g. between flights of the aircraft). The may allow the characteristics of the fuel for each use of the aircraft to be determined. In yet other examples, the surface deposits may not be removed between uses, in which case the sensor 115 is arranged to determine a maximum change in the vibrational parameter since the piezoelectric crystal was last cleaned, reset or replaced. This may allow a build-up of surface deposits over multiple uses of the aircraft (e.g. multiple flights) to be determined.

For example, a fuel characteristic determined based on the vibrational parameter may include an oxygen content of the fuel, a thermal stability of the fuel and/or a coking level of the fuel. The amount of surface deposit formed and detected on the piezoelectric crystal will have a dependence on these characteristics/properties of the fuel allowing them to be determined based on measurement of the vibrational parameter. In other examples, other fuel characteristics may be determined or inferred based on the measured vibrational parameters or other fuel characteristics determined from the vibrational parameters. For example, the hydrocarbon distribution of the fuel, the percentage of SAF within the fuel or the aromatic hydrocarbon content in the fuel (e.g. percentage by mass or volume) may be determined.

The fuel characteristic determination module 117 is arranged to transmit the determined one or more fuel characteristics to the electronic engine controller EEC 42 (or other control system of the aircraft). In some examples, the determination module 117 may be part of the EEC 42 of any one or more of the gas turbine engines of the aircraft. Once received at the EEC the fuel characteristics can be used to provide information on the fuel that is being provided from the fuel tanks to the engine such that operation of the gas turbine engine(s) can be adapted accordingly. In yet other examples, the determination module 117 may be part of the sensor unit 115, which is in communication with the EEC.

In order to determine the one or more fuel characteristics, the determination module 117 may be arranged to compare a measured vibrational parameter to a look-up table of expected vibrational parameter values of fuels with known fuel characteristics to determine the corresponding characteristics of the fuel to which the crystal has been exposed. This may allow a range of fuel characteristics to be determined based on a measurement of the surface deposit formed on the piezoelectric crystal. In yet other examples, the determination module may determine a level of surface deposition formed on the crystal using the measured resonant frequency of the crystal, and then compare the determined surface deposition level to values in a look-up table. The skilled person will understand that this is equivalent to comparing the resonant frequency.

In some examples, an absolute value of the vibration parameters may be measured and used by the determination module 117 to determine the one or more fuel characteristics. In other examples, a change in the vibrational parameter may be used. For example, a deviation from an expected value if no surface deposit is present may be measured, or a change of the vibration parameter over time measured. This may allow a slow build-up of surface deposits on the crystal to be measured and used to infer the one or more fuel characteristics. Using this method the characteristics of the fuel being used by the aircraft over an extended period of time may be determined.

The determination module 117 may further base the fuel characteristic determination on one or more performance parameters of the engine or the aircraft. This may include a temperature of the fuel to which the surface of the piezoelectric crystal has been exposed. This may allow the expected vibrational parameters formed by fuels of known characteristics at known temperatures to be compared to the measured data in order to determine the fuel characteristics. In other examples, other operating parameters may be used by the determination module 117 so that a relevant fuel characteristics can be reliably determined.

In the examples described above the fuel characteristic determination system 114 is located on board the aircraft 1 so that fuel within the fuel transmission line 63 flows through it before reaching the fuel tanks 53, 55. In other examples, the fuel characteristic determination system 114 may be arranged to use fuel within, or sampled from, one of the fuel tanks 53, 55. In such an example, the sensor 115 may located within the fuel tank so that fuel may be exposed to piezoelectric crystal 116. The sensor may therefore comprise a piezoelectric crystal mounted to an interior wall of the fuel tank such that it is exposed to fuel within the tank. In other examples, fuel may be sampled from a fuel tank aboard the aircraft and passed through the sensor 115.

In other examples, the fuel characteristic determination system 114, or at least part of it, may be located separately from the aircraft 1. For example, it may be included in the fuel loading line 61 so that it may detect properties of the fuel before it reaches the aircraft. In some examples, the sensor 115 may be located within the fuel loading line, or elsewhere separately from the aircraft 1, and arranged to transmit a vibrational parameter to a determination module 117 located on board the aircraft 1, where it can be communicated to a control module of the engine (e.g. the EEC) or aircraft. In yet other examples, the fuel characteristic determination system 114 may be located entirely outside of the aircraft. In such an example, the fuel characteristic determination module 117 may determine a fuel characteristic which is then communicated to the aircraft 1 (e.g. to a control module of the engines or engines 10). In this example, a data transfer link may be provided (e.g. a wireless or wired data connection) and may be used to communicate the fuel characteristics to the aircraft from the fuel characteristic determination system 114. In some examples, the data transfer may be done manually by a user, e.g. a technician or other operator of the system may obtain the fuel characteristics from the determination system 114 and manually provide them to a control module on board the aircraft.

Fuel Characteristic Determination within Engine Using Piezoelectric Sensor

Figure 7:
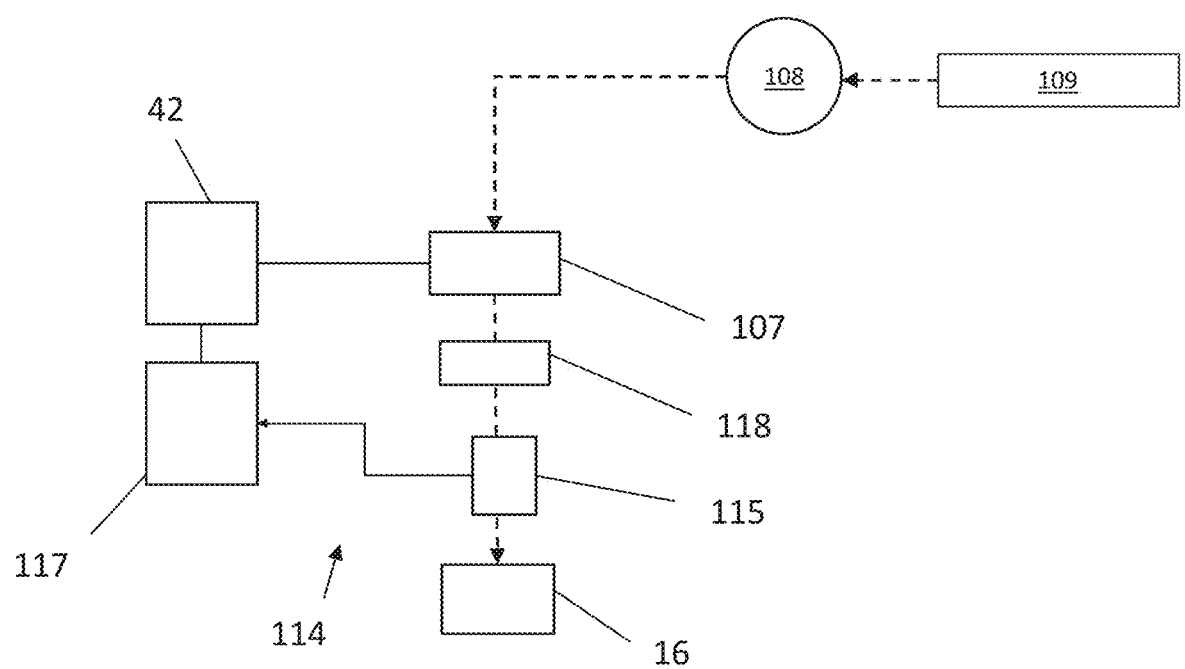
FIG. 7 is schematic view of a fuel characteristic determination system provided within a fuel system of a gas turbine engine.

FIG. 7 illustrates another example of the fuel characteristic determination system 114 described above. The fuel characteristic determination system of FIG. 7 similarly comprises a sensor 115 and fuel characteristics determination module 117 arranged to measure one or more fuel characteristics based on a vibrational parameter (e.g. resonant frequency) of a piezoelectric crystal exposed to fuel within the sensor. In this example, the fuel characteristic determination system 114 is arranged to measure the effects of the piezoelectric crystal 116 being exposed to fuel during operation of the gas turbine engine 10.

FIG. 7 shows a schematic view part of the fuel system of the aircraft and the combustion equipment 16 of the gas turbine engine 10. The combustion equipment 16 comprises a plurality of fuel nozzles (not shown in FIG. 7) arranged to inject fuel into a combustion can. Fuel is provided to the combustion equipment 16 by a fuel delivery regulator 107 under the control of the EEC 42. Fuel is delivered to the fuel delivery regulator 107 by a fuel pump 108 from a fuel source 109 on board the aircraft 1 (e.g. one or more fuel tanks 53, 55 as described above). The fuel delivery regulator 107 and combustion equipment 16 may be of known design, and may be arranged for staged (lean-burn) combustion or rich-burn combustion.

In this example, a vibrational parameter is measured for fuel as it is being used by the engine. The sensor 115 in this example is arranged to measure the effect of fuel exposed to the piezoelectric crystal 116 at any point within the fuel system on board the aircraft that is upstream of the combustion equipment 16 (e.g. upstream of the fuel nozzles of the combustion equipment 16) and downstream of the fuel source 109 from which the fuel is supplied (e.g. downstream of the one or more fuel tanks 53, 55 forming the fuel source). In some examples, the sensor 115 is located at a point within the engine fuel system such as in a fuel conduit within or forming part of the gas turbine engine 10 (rather than being on the aircraft 1 to which the gas turbine engine 10 is mounted). In some examples, it is located at a point immediately before the fuel enters the combustor 16. In yet other examples, the sensor 115 is located at a point within the aircraft fuel supply system e.g. before it enters part of the gas turbine engine 10.

In the presently described example, the engine fuel system further comprises a heat management system having a heat exchanger 118. The heat exchanger is arranged to transfer heat between the fuel and an oil system of the engine, e.g. transfer heat from the oil-system into the fuel so as to cool the oil and warm the fuel. As illustrated in FIG. 7, the sensor 115 is located within the engine fuel system at a point at which fuel has been heated by the heat exchanger 118 during operation of the gas turbine engine 10. The inventors have observed that during operation of the engine 10 heating of the fuel can result in thermal breakdown of the fuel that causes deposits to be formed on the surface of the piezoelectric crystal 116. For example, coking of the fuel can occur when the fuel is heated by the heat exchanger of the engine to provide cooling. The inventors have determined that the amount of deposit formed, and hence the vibrational parameters of the crystal, are dependent on the susceptibility of the fuel to thermal breakdown. As susceptibility of the fuel to thermal breakdown varies between different fuels, a measurement sensitive to the thermal breakdown can be used to determine the characteristics of the fuel being used by the engine. For example, the SAF content of the fuel may be determined, as a SAF rich fuel may be associated with a lower degree of thermal breakdown. In the present example, the fuel characteristic determination system is therefore arranged to determine characteristics of the fuel based on the measured level of thermal breakdown of the fuel.

In the example of FIG. 7 the fuel characteristic determination module 117 is arranged to compare the measured vibrational parameter (e.g. resonant frequency) or level of surface deposition to a look-up table of values corresponding to those expected for fuels of known characteristics. The fuel characteristic determination module 117 may further base the comparison with the look-up table on a temperature of the fuel to which the piezoelectric crystal is exposed with temperature values in the look-up table at which the changes in vibration parameters are expected for known fuel characteristics. Thus the measured surface deposit occurring at a certain temperature can be referenced in the look-up table to that of a known fuel at the same or similar temperature.

In the presently described examples, the fuel characteristic determination module 117 is arranged to determine the one or more fuel characteristics based only on the determined vibration parameter of the piezoelectric crystal 116. In other examples, the determination module 117 may be arranged to combine the vibration parameter information with inputs from other sensors or other methods of determining fuel characteristics disclosed herein. This may allow a greater range of types of fuel characteristic to be inferred, or improve the accuracy of the fuel characteristic determination.

Figure 8:
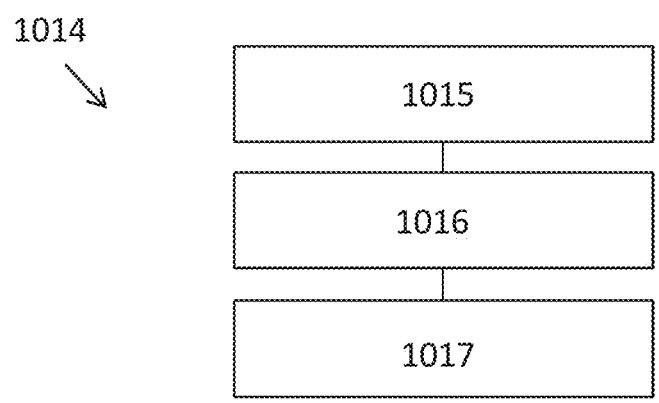
FIG. 8 is a schematic representation of a method of determining fuel characteristics of an aviation fuel.

FIG. 8 illustrates a method 1014 of determining one or more fuel characteristic of an aviation fuel suitable for powering a gas turbine engine of an aircraft that can be performed by the fuel characteristic determination systems 114 shown in FIGS. 5, 6 and 7. The method 1014 comprises exposing 1015 the surface of a piezoelectric crystal to the fuel; measuring 1016 a vibration parameter of the piezoelectric crystal; and determining 1017 one or more fuel characteristics of the fuel based on the vibration parameter. Any of the features described above in connection with FIGS. 5, 6 and 7 can be incorporated in the method of FIG. 8, and so will not be repeated here.

Figure 9:
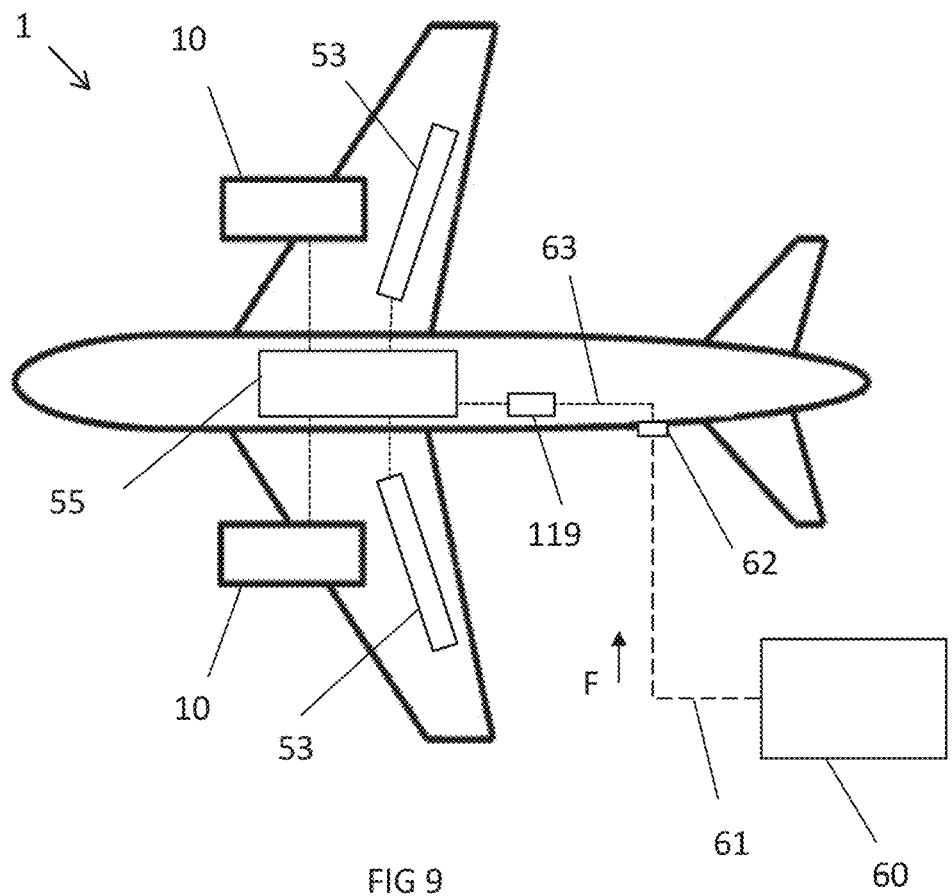
FIG. 9 is a schematic view of an aircraft including another example of a fuel characteristic determination system.

Seal Swell Sensor
Fuel Characteristic Determination During Refueling Using Swell Sensor Referring to FIG. 9, another example of a fuel characteristic determination system 119 is illustrated, located on board the aircraft 1. The fuel characteristic determination system 119 in this example is arranged to determine one or more fuel characteristics of fuel F being loaded onto the aircraft 1, those characteristics being any of those described or claimed herein.

Figure 10:
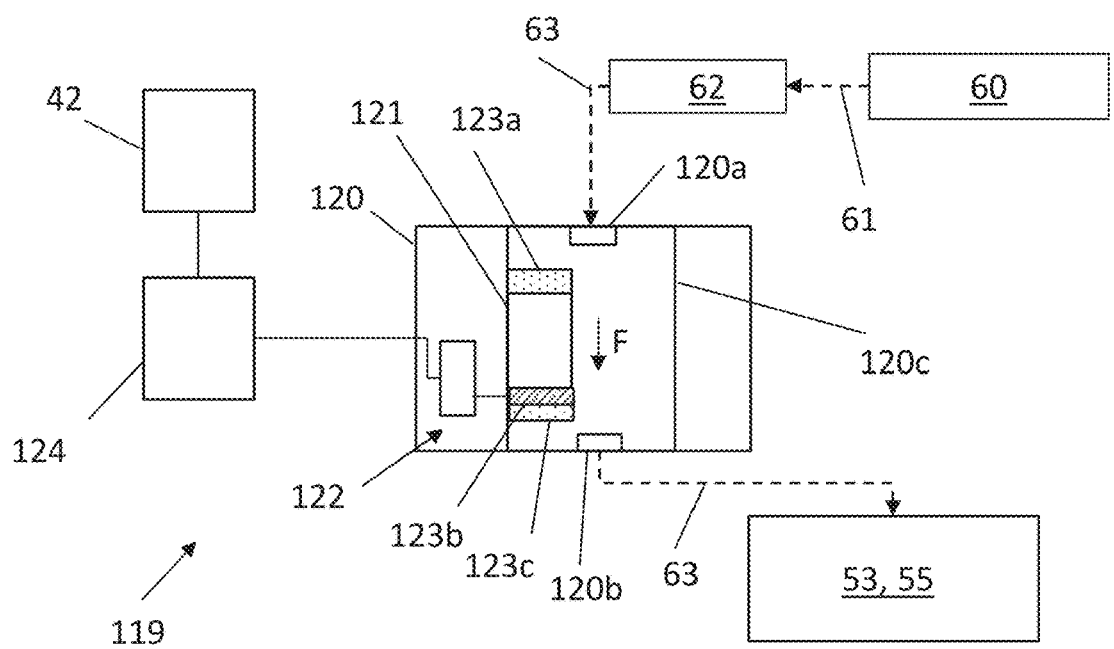
FIG. 10 is a close-up schematic view of the fuel characteristic determination system of FIG. 9.

Further details of the fuel characteristic determination system 119 are illustrated in FIG. 10. The fuel characteristic determination system 119 generally comprises a detection device 120 that is located within the fuel system of the aircraft. The detection device 120 comprises a sensor component 121 formed from a seal material. In some examples as described later, the seal material is formed from the same material as one or more seals provided in the fuel supply system. The one or more seals are exposed to the fuel during use of the fuel system of the aircraft, and are configured to swell upon contact with the fuel. In other examples, the seal material may be different from those used elsewhere in the fuel system of the aircraft or engine. The seal material may be nitrile seal material (e.g. nitrile rubber or Buna-N). The seals may be any seals that are exposed to fuel within the fuel system of the aircraft.

In the present example, fuel being loaded onto the aircraft is passed through the detection device 120 and is exposed to the sensor component 121. The detection device 120 comprises a fuel inlet 120a and a fuel outlet 120b, and a fuel conduit 120c arranged in fluid communication between them. In the present example, detection device 120 is located on board the aircraft and is arranged to receive fuel flowing through the fuel transmission line 63 i.e. fuel flowing from the fuel line connection port 62 to the fuel tanks 53, 55. The sensor is arranged such that all of the fuel flowing through the transmission line 63 is input to the inlet 120a, flows through the fuel conduit 120c, and is output via the fuel outlet 120b to continue to the fuel tanks (i.e. the detection device is connected in series between the fuel line connection port 62 and the fuel tanks). In other examples, the detection device 120 may be connected in parallel such that only some of the fuel is redirected from the transmission line 63, flows through the detection device 120, and then is returned to the fuel transmission line 63 or to the fuel tanks.

The fuel characteristic determination system further comprises a sensor 122 arranged to measure a swell parameter of the seal material from which the sensor component 121 is made. The swell parameter indicates the degree to which the seal material has changed in shape and/or size in response to the exposure of fuel F to its surface. The inventors have determined that the degree of swell of the sensor component 121 varies according the properties of the fuel F to which it is exposed. For example, the seal material from which the sensor component 121 is made may expand or contract according to the characteristics of the fuel. By measuring expansion or contraction of the seal material (or change thereof over time) various properties of the fuel F may be determined based on the corresponding swell parameter.

Referring again to FIG. 10, the sensor component 121 of the present example is fixedly mounted within the detection device 120 via a fixing structure 123a. As can be seen schematically in FIG. 10, part of the sensor component 121 is fixedly coupled to the detection device 120 so that it is free to expand or contract in response to exposure to the fuel. The sensor 122 further comprises a gauge 123b relative to which the seal material is fixedly mounted. In the present example, the gauge 123b is fixedly mounted within the detection device 120 via a gauge fixing structure 123c. The gauge 123b is arranged to detect movement of part of the sensor component 121 resulting from its expansion or contraction. The gauge 123b may be a pressure sensing device arranged to detect a pressure exerted on it by the sensor component 121. As can be seen in FIG. 10 the sensor component is constrained between the fixing structure 123a and the gauge 123b such that any change in its size will result in a change in the pressure applied to the gauge 123b.

In other examples, other methods of detecting the expansion or contraction of the sensor component 121 can be used. For example, the gauge may be arranged to detect a change in physical shape of the sensor component. The gauge may, for example, be arranged to detect a change in the physical position of an unconstrained surface of the sensor component to determine the level of expansion or contraction.

The fuel characteristic determination system 119 of the present example further comprises a fuel characteristic determination module 124 arranged to determine one or more fuel characteristics of the fuel F based on the swell parameter. The fuel characteristic determination module 124 receives the swell parameter from the sensor 122 such that the one or more fuel characteristics can be calculated.

The fuel characteristic determination system 119 of the present example may be arranged to determine any one or more of the fuel characteristics defined or claimed herein based on the swell parameter. For example, the fuel characteristic determination system 119 may be arranged to determine a hydrocarbon distribution of the fuel, for example a property related to the aromatic hydrocarbon content of the fuel. The one or more fuel characteristics determined may therefore include the percentage by mass or volume of aromatic hydrocarbon compounds in the fuel. The inventors have determined that the aromatic content of the fuel is related to the swell of the seal material, with different levels of aromatic compounds resulting in different levels of swell. Measurement of the swell parameter may therefore be used to determine the aromatic content of the fuel. Other fuel characteristics may however be determined based on the swell parameter. For example, other fuel characteristics such as the percentage of sustainable aviation fuel present within the fuel may be determined (e.g. by being inferred from the level of aromatic content, or because of the resulting change in size of the seal material compared to a fuel of known characteristics). In other examples, the fuel characteristic may be the cycloparaffin content of the fuel.

The fuel characteristic determination module 124 is arranged transmit the determined one or more fuel characteristics to the electronic engine controller EEC 42 (or other control module of the aircraft). In some examples, the determination module 124 may be part of the EEC 42 of any one or more of the gas turbine engines of the aircraft. Once received at the EEC the fuel characteristics can be used to provide information on the fuel that is being provided from the fuel tanks to the engine such that operation of the gas turbine engine(s) can be adapted accordingly. In yet other examples, the determination module 124 may be part of the detection device 120, which is in communication with the EEC.

In order to determine the one or more fuel characteristics, the determination module 124 may be arranged to compare a swell parameter to a look-up table of expected swell parameter values of fuels with known fuel characteristics to determine the corresponding characteristics of the fuel to which the sensor component has been exposed. This may allow a variety of fuel characteristics to be determined.

In some examples, an absolute value of the swell parameters may be measured and used by the determination module 124 to determine the one or more fuel characteristics. In other examples, a change in the swell parameter may be used. For example, a deviation from an expected value may be measured, or a change of the swell parameter over time measured. This may allow a slow change in the expansion or contraction of the seal material to be measured and used to determine the one or more fuel characteristics. Using this method, the characteristics of the fuel being used by the aircraft over an extended period of time may be determined.

In the examples described above the fuel characteristic determination system 119 is located on board the aircraft 1 so that fuel within the fuel transmission line 63 flow through it before reaching the fuel tanks 53, 55. In other examples, the fuel characteristic determination system 119 may be arranged to use fuel with, or sampled from, one of the fuel tanks 53, 55. In such an example, the detection device 120 may be located within the fuel tank so that fuel may be exposed to the sensor component 121. The detection device may therefore comprise the sensor component mounted to an interior wall of the fuel tank such that it is exposed to fuel within the tank. In such an example, the inlet 120*a*, outlet 120*b* and conduit 120*c* structure may not be required. The fixing structure 123*a*, gauge fixing structure 123*c* and gauge 123*b* however may still be provided. The In other examples, fuel may be sampled from the tank and passed through the detection device 120.

In other examples, the fuel characteristic determination system 119, or at least part of it, may be located separately from the aircraft 1. For example, it may be included in the fuel loading line 61 so that it may detect properties of the fuel before it reaches the aircraft. In some examples, the detection device 120 may be located within the fuel loading line, or elsewhere separately from the aircraft 1, and arranged to transmit a swell parameter to a fuel characteristic determination module 124 located on board the aircraft 1, where it can be communicated to a control module of the engine (e.g. the EEC) or the aircraft. In yet other examples, the fuel characteristic determination system 119 may be located entirely outside of the aircraft. In such an example, the fuel characteristic determination module 124 may determine a fuel characteristic which is then communicated to the aircraft 1 (e.g. to a control module of the engines or engines 10). In this example, a data transfer link may be provided (e.g. a wireless or wired data connection) and may be used to communicate the fuel characteristics to the aircraft from the fuel characteristic determination system 119. In some examples, the data transfer may be done manually by a user, e.g. a technician or other operator of the system may obtain the fuel characteristics from the fuel characteristic determination system 119 and manually provide them to a control module on board the aircraft.

Fuel Characteristic Determination During Engine Operation Using Swell Sensor

Figure 11:
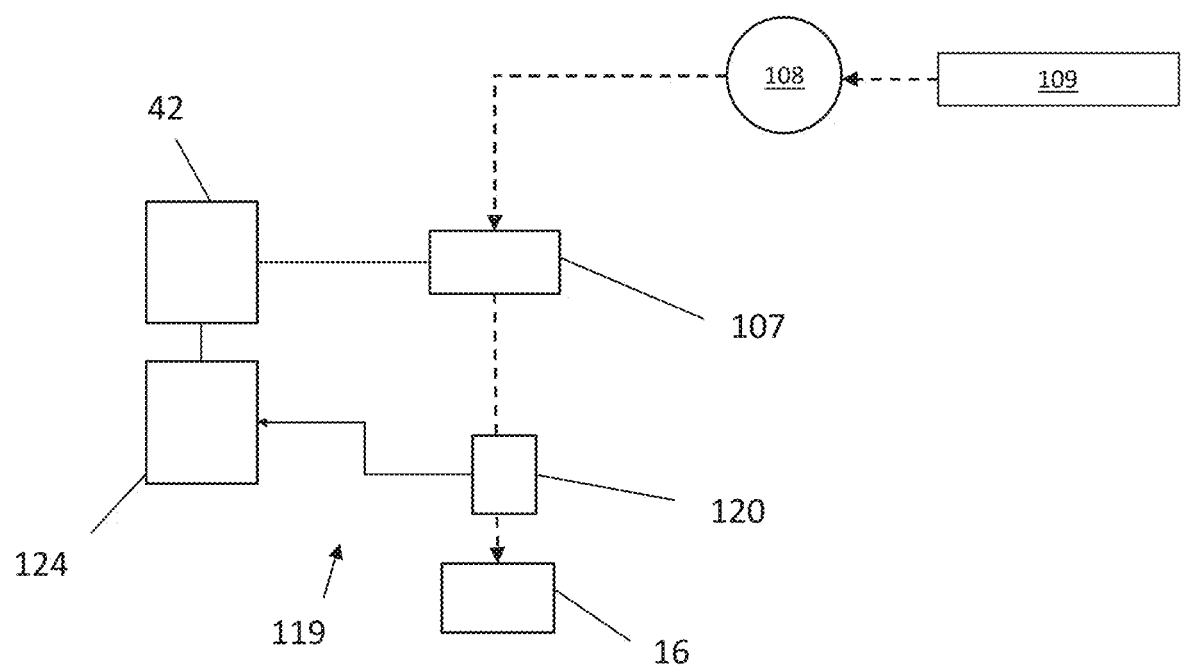
FIG. 11 is schematic view of a fuel characteristic determination system provided within a fuel system of a gas turbine engine.

FIG. 11 illustrates another example of the fuel characteristic determination system 119 described above. The fuel characteristic determination system of FIG. 11 similarly comprises a detection device 120 and determination module 124 arranged to measure one or more fuel characteristics based on a swell parameter. The swell parameter is determined by measuring the expansion or contraction of a sensor component exposed to fuel within the detection device 120. In this example, the fuel characteristic determination system 119 is arranged to measure the effects of fuel being exposed to the sensor component 121 during operation of the gas turbine engine 10.

FIG. 11 shows a schematic view of part of the fuel system of the aircraft and the combustion equipment 16 of the gas turbine engine 10. The combustion equipment 16 comprises a plurality of fuel nozzles (not shown in FIG. 11) arranged to inject fuel into a combustion can. Fuel is provided to the combustion equipment 16 by a fuel delivery regulator 107 under the control of the EEC 42. Fuel is delivered to the fuel delivery regulator 107 by a fuel pump 108 from a fuel source 109 on board the aircraft 1 (e.g. one or more fuel tanks as described above). The fuel delivery regulator 107 and combustion equipment 16 may be of known design, and may be arranged for staged (lean-burn) combustion or rich-burn combustion.

In this example, a swell parameter is measured for fuel as it is being used by the engine. The detection device 120 in this example is arranged to measure the effect of fuel exposed to the sensor component 121 at any point within the fuel system of the aircraft that is upstream of the combustion equipment 16 (e.g. upstream of the fuel nozzles of the combustion equipment 16) and downstream of the fuel source 109 from which the fuel is supplied (e.g. downstream of the one or more fuel tanks 53, 55 forming the fuel source). In some examples, the detection device 120 is located at a point within the engine fuel system such as in a fuel conduit within or forming part of the gas turbine engine 10 (rather than being on the aircraft 1 to which the gas turbine engine 10 is mounted). In some examples, it is located at a point immediately before the fuel is combusted (e.g. immediately before entering the combustor). In yet other examples, the detector device 120 is located at a point within the aircraft fuel supply system e.g. before it enters part of the gas turbine engine 10.

In the example shown in FIG. 11, the detector device 120 is arranged such that all of the fuel flowing to the combustor passes through it (e.g. it is arranged in series). In other examples, only some of the fuel may pass through the detector device 120. For example, the detector device may be located in bleed line of the fuel system at which fuel is sampled from fuel supply to the combustor (e.g. before or after fuel mixing).

In the presently described examples (e.g. as shown in FIGS. 9, 10 and 11), the fuel characteristic determination module 124 is arranged determine the one or more fuel characteristics based only on the determined swell parameter of the seal material component 121. In other examples, the determination module 124 may be arranged to combine the swell parameter information with inputs from other sensors or other methods of determining fuel characteristics disclosed herein. This may allow a greater range or types of fuel characteristic to be inferred, or improve the accuracy of the fuel characteristic determination.

In any of the examples described above, the fuel characteristic determination system is arranged to generate an alert signal if the swell parameter is beyond an alert threshold or outside an acceptable range i.e. above a first upper threshold or below a second lower threshold. The alert signal may be generated by the fuel characteristic determination module 124, or may be generated at the sensor 122. The alert signal may be generated based on a comparison to an alert threshold e.g. if the swell parameter exceeds or is below the alert threshold. For example, if the swell parameter indicates that the swell of the material has fallen below a safety threshold, the alert signal may be generated to indicate that seals made from the same or similar material on board the aircraft may have contracted to a degree that would affect their sealing ability. This may be used to provide an indication that there is a risk of insufficient sealing by seals that rely on swelling in size on exposure to fuel during use.

Figure 12:
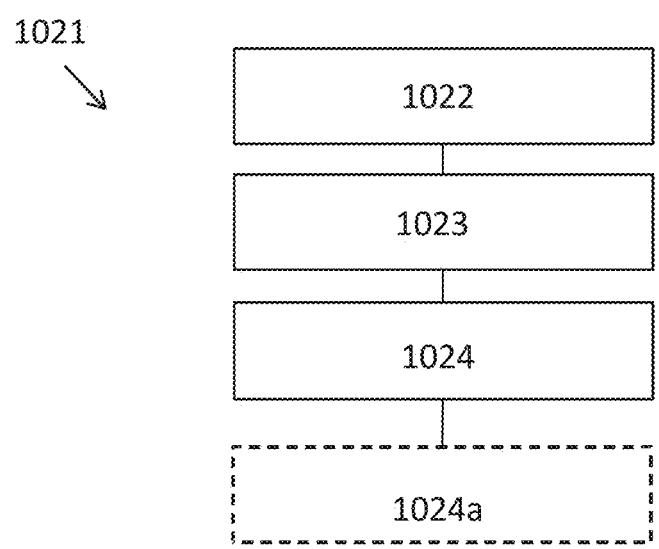
FIG. 12 is a schematic representation of another example of a method of determining fuel characteristics of an aviation fuel.

FIG. 12 illustrates a method 1021 of determining one or more fuel characteristics of an aviation fuel suitable for powering a gas turbine engine of an aircraft. The method 1021 can be performed by the fuel characteristic determination systems 119 shown in FIGS. 9, 10 and 11. The method 1021 comprises exposing 1022 the surface of a component formed from a nitrile seal material (e.g. sensor component 121); measuring 1023 a swell parameter of the seal material; and determining 1024 one or more fuel characteristics of the fuel based on the swell parameter. The method may further comprise generating 1024a an alert signal if the swell parameter is outside of an alert threshold (e.g. above or below the threshold). Any of the features described above in connection with FIGS. 9, 10 and 11 can be used in the method 1021, and so will not be repeated here.

As discussed more generally below, the method 1021 of determining one or more fuel characteristics may be part of a method of operating an aircraft 1065. In such a method, the aircraft, or more specifically a gas turbine engine mounted to the aircraft, is operated according to the one or more fuel characteristics determined using the method 1021. In some examples, operating the aircraft according to the fuel characteristics may include providing a fuel having at least one different characteristic to those measured to the combustor of the gas turbine engine. This may be done by refueling using fuel having different characteristics the next time the aircraft is refueled, or may comprise controlling the supply of fuel from different fuel sources on board the aircraft. For example, fuel from an alternative fuel tank holding fuel of a different characteristic may be used, or a different blend of fuels used from two or more different sources.

The supply of a fuel having a different characteristic may comprise: providing fuel with a relatively higher aromatic content compared to which the fuel characteristics were determined; ii) providing fuel with a lower SAF content compared to which the fuel characteristics were determined; and/or iii) providing fossil kerosene fuel. This may allow a fuel causing a greater expansion of the seal material to be used, which may aid the performance of other seals provided in the fuel system of the aircraft by increasing their swell response to the fuel. In other examples, other operating parameters of the aircraft or gas turbine engine may be modified in response to the determined fuel characteristics.

Fuel Characteristic Determination Using a Sensor Component Made from a Material Matching that of Other Seals on Board the Aircraft:

In the examples described above the seal material of the sensor component 121 is a nitrile seal material. The specific material chosen for use as a sensor may be independent of any other types of seal material used aboard the aircraft. The material may therefore be chosen according to a desired response to certain fuel characteristics to be determined. In other examples, however, the seal material is not limited to being a specific type of material, but is chosen such that it is the same as the material of one or more seals that are used on board the aircraft.

Figure 13:
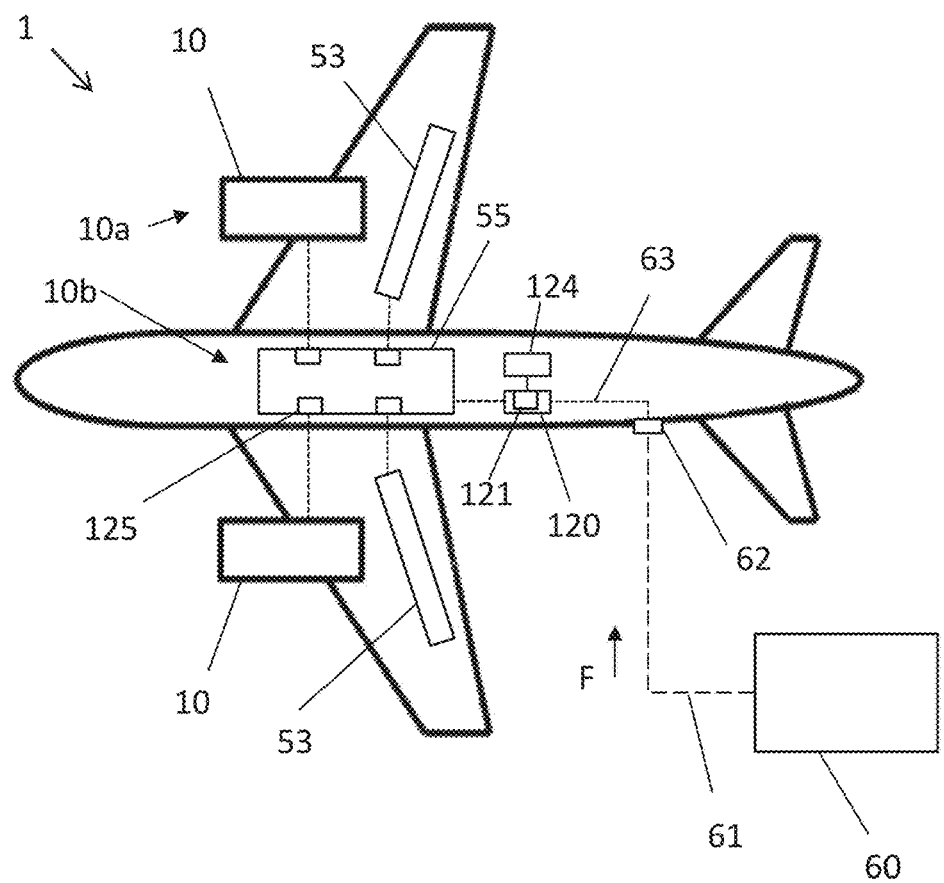
FIG. 13 is a schematic view of a fuel characteristic determination system having a sensor component made from the same material as one or more seals provided in a fuel system of an aircraft.

An example in which the seal material matches that of the aircraft is illustrated in FIG. 13. Features common to FIGS. 9, 10 and 11 are labelled accordingly. A propulsion system 10a for an aircraft is illustrated, having gas turbine engines 10 and a fuel system 10b comprising fuel tanks 53, 55 arranged to contain fuel for supply to the gas turbine engine. In other examples, any number of gas turbine engines and fuel tanks may be provided. The fuel system 10b may correspond to the "fuel system of the aircraft" introduced previously, including the engine fuel system and aircraft fuel supply system.

The fuel system 10b further comprises seals 125 (only one of which is labelled). The seals in the present examples are arranged to seal fuel conduits extending between the centre (fuselage) fuel tank 55 and the wing fuel tanks 53 and the gas turbine engines 10. The seals 125 are exposed to fuel from the fuel tanks 53, 55 during use of the aircraft. In other examples, the seals may be provided for any other use within the fuel system of the aircraft which are exposed to fuel during use. They may, for example, be part of a fuel pump. The seals 125 are of a type arranged to swell in response to exposure to fuel during use in order to providing sealing, and may be formed from a nitrile seal material.

The propulsion system further comprises a detection device 120 located within the fuel system of the aircraft 1. The detection device may include the same components as that described above in connection with FIGS. 10 and 11, and includes a sensor component 121 which is exposed to the fuel within the fuel system. The sensor component is formed from the same material as the seals 125 provided in the fuel system of the aircraft. The detection device 120 is arranged to detect or determine a swell parameter of the seal material component as described above.

The inventors have determined that by detecting the swell of a sensor component made from the same material as the seals otherwise provided in the fuel system of the aircraft the degree of swell of the seals themselves can be determined. This allows indirect monitoring of the degree of swell of the seals, without having to disassemble components for inspection. As the seals 125 are intended to swell in order to provide sufficient sealing, measuring of the swell of the sensor component 121 can provide an indirect measurement of their performance. For example, a reduction in the swell of the sensor component 121 below a threshold may indicate that the other seals within the fuel system of the aircraft would not have a sufficient degree of swell to ensure sealing. The detection device may be arranged to generate an alert signal if the swell parameter falls below an alert threshold to indicate that insufficient swell of the seals 125 may be occurring.

The detection device 120 may be provided such that it received fuel during use of the gas turbine engine. It may, for example, be located as described in connection with FIG. 11.

In the present example, the propulsion system further comprises a fuel characteristic determination module 124 as described above to allow fuel characteristics to be determined based on the swell parameter. This can be achieved in the same way as described above in connection with FIGS. 9, 10 and 11. Any feature described above in connection with those figures may be used in combination with the example shown in FIG. 13.

In other examples, the fuel characteristic determination module 124 may not be provided. In such examples, the fuel swell parameter may be used to indicate swell of the seals 125, rather than allow fuel characteristics to be determined.

Figure 14:
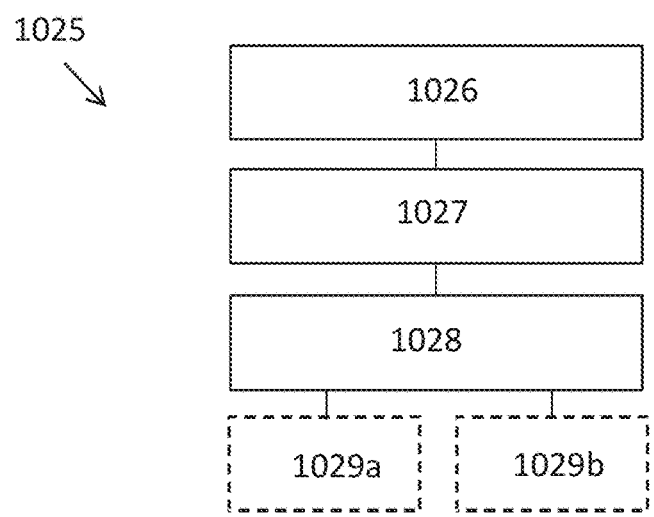
FIG. 14 is a schematic representation of another example of a method of determining fuel characteristics of an aviation fuel.

FIG. 14 illustrates a method 1025 that may be performed using the example of FIG. 13. The method 1025 comprises: exposing 1026 one or more seals of the fuel supply system of the aircraft to fuel within the fuel supply system; exposing 1027 the sensor component 121 made from the same material as the one or more seals to the fuel, the component being located within the fuel system of the aircraft; and measuring 1028 a swell parameter of the seal material. The method 1025 may further comprise determining 1029a one or more fuel characteristics of the fuel based on the swell parameter and/or generating 1029b an alert signal if the swell parameter exceeds an alert threshold. Any of the features described above in connection with FIGS. 9 to 13 may be incorporated into the method of FIG. 14.

Figure 15:
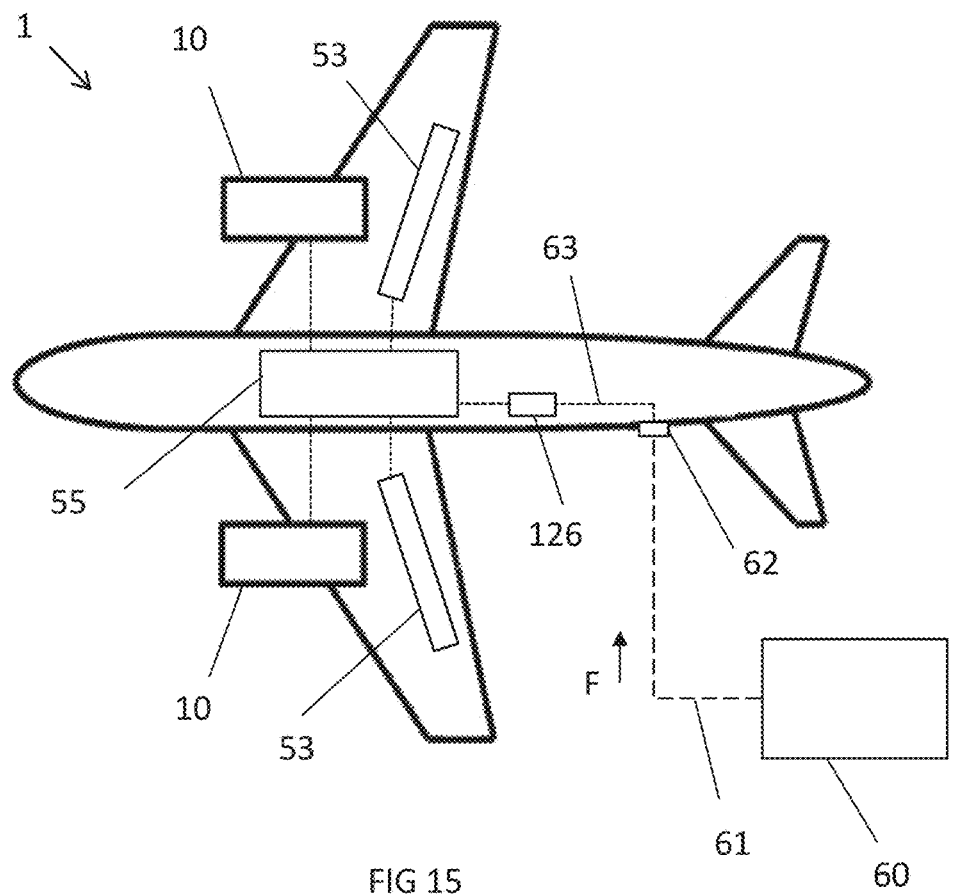
FIG. 15 is a schematic view of an aircraft including another example of a fuel characteristic determination system.

Trace Substance Sensor
Fuel Characteristic Determination During Refueling Using a Trace Substance Sensor:

Referring to FIG. 15, another example of a fuel characteristic determination system 126 is illustrated, located on board the aircraft 1. The fuel characteristic determination system 126 in this example is arranged to determine one or more fuel characteristics of fuel being loaded onto the aircraft 1, those characteristics being any of those described or claimed herein. In this example, the fuel characteristic is determined based on the detection of trace substances in the fuel F.

Figure 16:
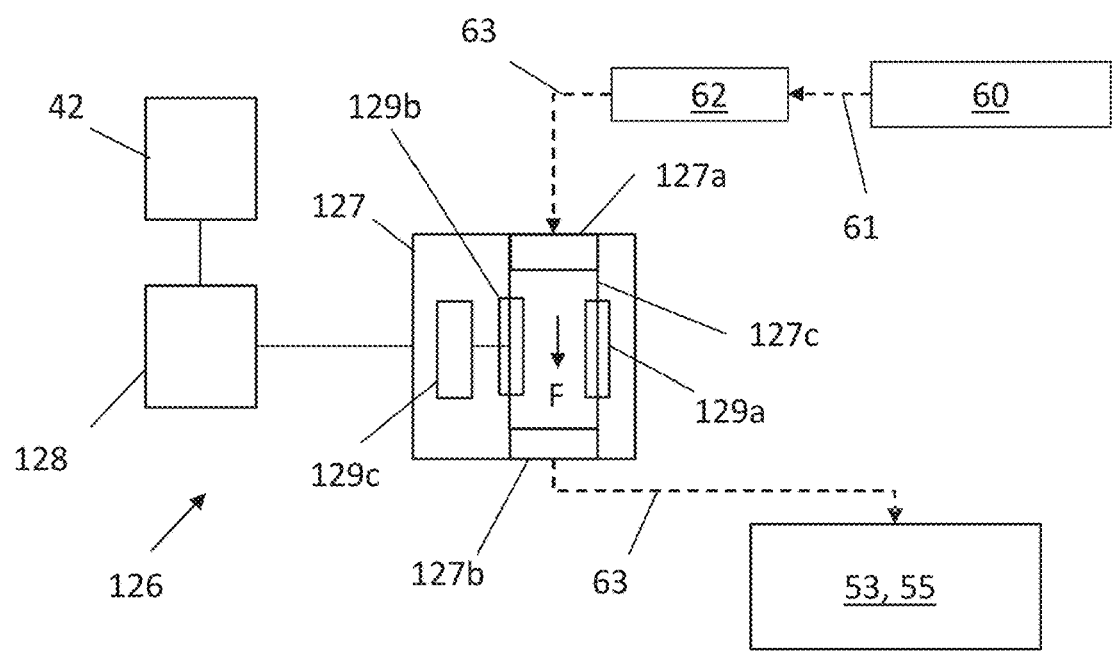
FIG. 16 is a close-up schematic view of the fuel characteristic determination system of FIG. 15.

Further details of the fuel characteristic determination system 126 are illustrated in FIG. 16. The fuel characteristic determination system 126 generally comprises a trace sensor 127 which is arranged to measure one or more trace substance parameters of the fuel being supplied to the aircraft fuel tanks 53, 55.

The trace substance parameters measured by the sensor 127 are each associated with a respective trace substance in the fuel. By trace substance we mean a substance in the fuel whose concentration (or other measure of amount) is very low i.e. it is present in a trace amount. A trace substance may include any type of substance present in trace amounts, for example trace chemical elements, compounds, molecules etc. The trace substance may be a substance which, based on its presence, absence, or amount in the fuel, one or more characteristics of the fuel can be directly determined or inferred. The trace substance parameter(s) may in some examples indicate the presence of a concentration of the associated trace substance in the fuel. They may therefore be a concentration measured as the mass fraction of a trace substance in the fuel (e.g. a concentration in parts-per-million). In other examples, the trace substance parameter(s) may indicate the absence or presence (e.g. within measurement limits) of an associated trace substance in the fuel.

The fuel characteristic determination system 126 further comprises a determination module 128 arranged to determine one or more fuel characteristics of the fuel based on the trace substance parameters. The determination module 128 is arranged to receive the trace substance parameter from the trace sensor 127 such that the one or more fuel characteristics can be calculated.

The inventors have determined that by measurement of trace substances present or absent within a fuel the characteristics of that fuel can be determined either directly or indirectly.

In one example, the trace substance parameter measured by the trace sensor 127 is associated with a sulphur content of the fuel. The trace substance parameter may in this example be a concentration (or other measurement of amount) of sulphur molecules within the fuel. The inventors have observed that for all SAF production pathways the resulting fuel is characterised by having an almost complete absence of sulphur molecules. The inventors have determined that this can be used as an indicator of the amount of SAF content of the fuel by measurement of the concentration of sulphur molecules by the trace sensor 127. The fuel characteristic determination system 126 may in this example compare the measured sulphur content of the fuel to that corresponding to fossil derived fuel. This may allow the system 126 to determine a percentage of SAF in the fuel F being supplied to the aircraft. As a SAF contains almost completely no sulphur molecules, the measured concentration can be compared to a sulphur concentration of typically around 500 ppm (and up to 3000 ppm) of elemental sulphur within a fossil aircraft fuel. By measuring a reduction in the sulphur content the relative amount of SAF present in the fuel as a percentage of the total fuel (e.g. the percentage SAF per unit mass or volume) can therefore be derived (for example using knowledge of the amount of sulphur (e.g. in ppm) within the fossil fuel to infer from a measured amount of sulphur (e.g. in ppm) within a fuel mixture what the percentage of SAF is within that mixture). In some examples, the trace substance parameters may indicate an absence (within a measurable limit) of sulphur molecules within the fuel F, based on which the fuel characteristic determination module 128 may determine that no fossil kerosene (within measurable limits) is present with the fuel.

In the example illustrated in FIG. 16, the sensor 127 comprises a fluorescence detection device arranged to measure the amount of sulphur molecules within the fuel F. As can be seen in FIG. 16, fuel being loaded onto the aircraft is passed through the sensor 127 where a trace substance measurement is performed on the fuel. The sensor 127 comprises a fuel inlet 127a and a fuel outlet 127b, and a fuel conduit 127c arranged in fluid communication between them. In the present example, the sensor 127 is located on board the aircraft and is arranged to receive fuel flowing through the fuel transmission line 63 i.e. fuel flowing from the fuel line connection port 62 to the fuel tanks 53, 55. The fluorescence detection device may provide a reliable method for detecting the concentration of sulphur molecules in the fuel. Other sensors or measurement techniques may however be used.

The fluorescence detection device comprises an excitation source 129a, such as an LED, which is arranged to emit radiation into the fuel F. The fluorescence detection device further comprises a detector 129b arranged to detect emitted fluorescent light. The detector 129b may be in communication with a processor module 129c configured to process a fluorescence signal from the detector 129c and calculate a trace substance parameter accordingly.

In the present example, the sensor 127 is arranged such that all of the fuel flowing through the transmission line 63 is input to the sensor inlet 127a, flows through the fuel conduit 127c, and is output via the fuel outlet 127b to continues to the fuel tanks (i.e. the sensor is connected in series between the fuel line connection port 62 and the fuel tanks). In other examples, the sensor 127 may be connected in parallel such that only some of the fuel is redirected from the transmission line 63, flows through the sensor, and then is returned to the fuel transmission line 63 or to the fuel tanks. In some examples, the sensor may be a microfluidic (lab-on-chip) device through which a small sample of fuel may be passed to perform a measurement of a trace substance parameter.

The fuel characteristic determination module 128 is arranged transmit the determined one or more fuel characteristics to the electronic engine controller EEC 42 or other control module of the aircraft. In some examples, the fuel characteristic determination module 128 may be part of the EEC 42 of any one or more of the gas turbine engines of the aircraft. Once received at the EEC the fuel characteristics can be used to provide information on the fuel that is being provided from the fuel tanks to the engine such that operation of the gas turbine engine(s) can be adapted accordingly. In yet other examples, the determination module 128 may be part of the sensor unit 127, which is in communication with the EEC.

In another example, the trace substance parameter may be associated with an aromatic content of the fuel F. In such an example, the trace substance parameter may be a concentration (or other equivalent measure of amount) of aromatic compounds within the fuel. The inventors have observed that for many SAF production pathways the resulting fuel essentially has no aromatic compounds. The inventors have determined that this can be used as an alternative indicator of the amount of SAF content of the fuel. In such an example, the sensor 127 is arranged to measure an aromatic compound concentration in the fuel F. The fuel characteristic determination system 126 may, in this example, compare the measured aromatic compound concentration to that corresponding to fossil derived fuel in order to determine a percentage of SAF in the fuel F being supplied to the aircraft. By measuring a reduction in the aromatic content compared to fossil kerosene, the relative amount of SAF present in the fuel as a percentage of the total fuel (e.g. the percentage SAF per unit mass or volume) can therefore be derived. In some examples, the trace substance parameters may indicate a measurable absence of aromatic compounds within the fuel F, based on which the fuel characteristic determination module may determine that no fossil kerosene is present within the fuel F.

In order to measure an aromatic concentration in the fuel F, the sensor 127 may comprise a spectroscopy device (in place of the fluorescence device shown in the example of FIG. 16). The spectroscopy device may comprise a Fourier Transform Infra red (FT-IR) spectroscopy device or an Ultraviolet Visual (UV-Vis) spectroscopy device. Such spectroscopy techniques may provide a reliable differentiation of aromatics from paraffins and other types of hydrocarbons in an aviation fuel. Other spectroscopy devices and techniques may however be used. The spectroscopy device may be similar in structure to the fluorescence device shown in FIG. 16.

In other examples, other trace substance parameters may be used, which are associated with different trace substances in order to determine fuel characteristics. Appropriate sensor devices may be used according to the relevant trace substance to be measured. In order to determine the one or more fuel characteristics, the determination module 128 may be arranged to compare a measured trace substance parameter to a look-up table of expected trace substance parameter values of fuels with known fuel characteristics to determine the corresponding characteristics of the fuel F. This may allow a variety of different fuel characteristics to be determined.

For example, the trace substance parameters may be associated with the presence/absence/amount of a non-hydrocarbon species in the fuel, including any one or more of the following:
 i) Nitrogen
 ii) Water
 iii) Sulphur
 iv) Metals (including any one or more of: Al, Ca, Co, Cr, Cu, Fe, K, Mg, Mn, Mo, Na, Ni, P, Pb, Pt, Sn, Sr, Ti, V, and/or Zn); and/or
 v) Halogens The inventors have determined that generally SAF is a much purer hydrocarbon fuel with very little in the way of trace species, when compared to conventional jet fuel processed from a crude source. As the SAF is effectively a controlled chemical process, any heteroatomic species seen in conventional jet fuel (sulphur, nitrogen, oxygen) or trace metals are at very low levels (often less than the limit of detection by analytical techniques). Detection of the presence/absence/concentration of one or more of these species may therefore provide a determination of whether a fuel is SAF, or is conventional jet fuel from a fossil source.

In the examples given above the trace substances occur inherently in the fuel F. By that we mean that they are trace substances which are not artificially added to the fuel, but are present (or absent) as a consequence of how the fuel is produced or the source that it is derived from. In other examples, the trace substance(s) may be added to the fuel for the purpose of providing an indicator for a particular fuel or fuel characteristic (e.g. they are a "tracer" substance). Such tracer substances may be added deliberately for later detection by the present methods. These may provide a binary distinction between the fuel being SAF or non-SAF fuel by the tracer being present or not, or the amount of trace substance could be added in proportion to a characteristic of the fuel, for example in proportion to the SAF content or aromatic content. In such an example, the amount of tracer present may then indicate the amount of content of another component of the fuel. For example, a phosphorescent or chemiluminescent species may be used as a tracer species, such as phosphorous or potassium. Such tracer species may be detected using a light or refraction sensor.

In the examples described above the fuel characteristic determination system 126 is located on board the aircraft 1 so that fuel within the fuel transmission line 63 flows through it before reaching the fuel tanks 53, 55. In other examples, the fuel characteristic determination system 126 may be arranged to use fuel within, or sampled from, one of the fuel tanks 53, 55. In such an example, the sensor 127 may be located within the fuel tank so that a fluorescence or spectroscopy measurement may be performed (or other suitable measurement depending on the trace substance detected). The sensor 127 may therefore be built into an interior wall of the fuel tank such that it is exposed to fuel within the tank. In other examples, fuel may be sampled from the tank and passed through the sensor 127.

In other examples, the fuel characteristic determination system 126, or at least part of it, may be located separately from the aircraft 1. For example, it may be included in the fuel loading line 61 so that it may detect properties of the fuel before it reaches the aircraft. In some examples, the sensor 127 may be located within the fuel loading line, or elsewhere separately from the aircraft 1, and arranged to transmit a trace substance parameter to the determination module 128 located on board the aircraft 1, where it can be communicated to a control module of the engine (e.g. the EEC). In yet other examples, the fuel characteristic determination system 126 may be located entirely outside of the aircraft. In such an example, the fuel characteristic determination module 128 may determine a fuel characteristic which is then communicated to the aircraft 1 (e.g. to a control module of the engines or engines 10). In this example, a data transfer link may be provided (e.g. a wireless or wired data connection) and may be used to communicate the fuel characteristics to the aircraft from the fuel characteristic determination system 126. In some examples, the data transfer may be done manually by a user, e.g. a technician or other operator of the system may obtain the fuel characteristics from the determination system 126 and manually provide them to a control module on board the aircraft.

Figure 17:
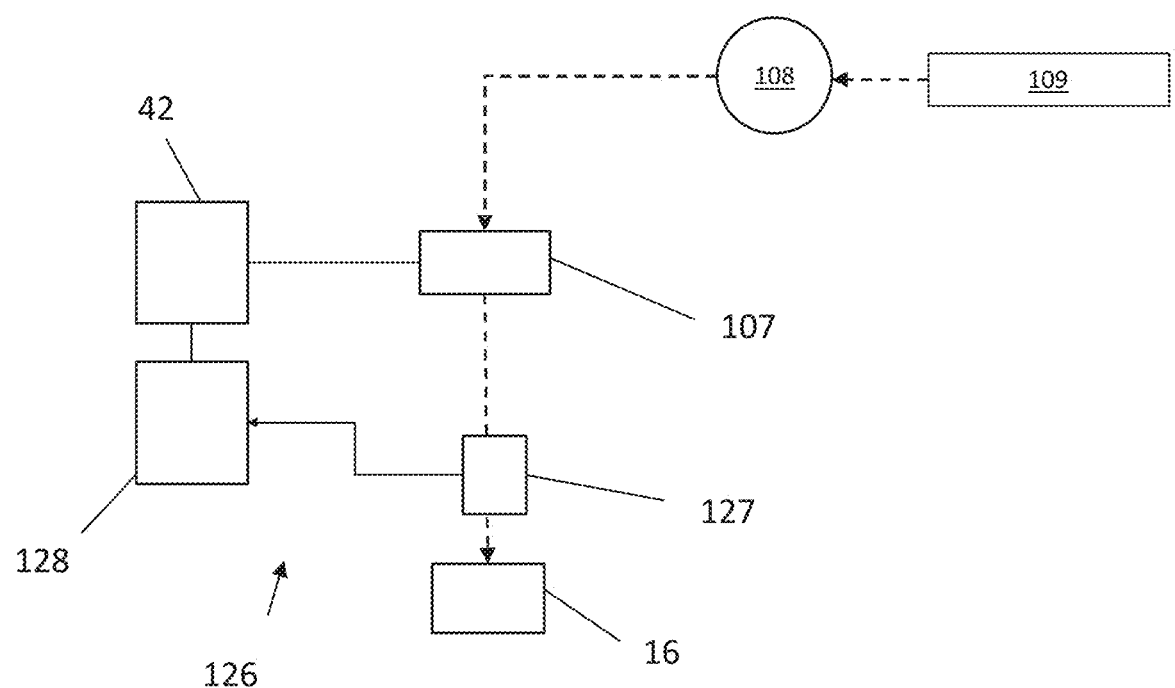
FIG. 17 is schematic view of another example of a fuel characteristic determination system provided within a fuel system of a gas turbine engine.

Fuel Characteristic Determination within Engine Using Trace Substance Sensor:

FIG. 17 illustrates another example of the fuel characteristic determination system 126 described above. The fuel characteristic determination system 126 of FIG. 17 similarly comprises a sensor 127 and determination module 128 arranged to measure one or more fuel characteristics based on a trace substance parameter.

FIG. 17 shows a schematic view of part of the fuel system of the aircraft and the combustion equipment 16 of the gas turbine engine 10. The combustion equipment 16 comprises a plurality of fuel nozzles (not shown in FIG. 17) arranged to inject fuel into a combustion can. Fuel is provided to the combustion equipment 16 by a fuel delivery regulator 107 under the control of the EEC 42. Fuel is delivered to the fuel delivery regulator 107 by a fuel pump 108 from a fuel source 109 on board the aircraft 1 (e.g. one or more fuel tanks as described above). The fuel delivery regulator 107 and combustion equipment 16 may be of known design, and may be arranged for staged (lean-burn) combustion or rich-burn combustion.

In this example, a trace substance parameter is measured for fuel as it is being used by the engine. The sensor 127 in this example is arranged to measure a trace substance parameter at any point within the fuel system of the aircraft that is upstream of the combustion equipment 16 (e.g. upstream of the fuel nozzles of the combustion equipment 16) and downstream of the fuel source 109 from which the fuel is supplied (e.g. downstream of the one or more fuel tanks 53, 55 forming the fuel source). In some examples, the sensor 127 is located at a point within the engine fuel system such as in a fuel conduit within or forming part of the gas turbine engine 10 (rather than being on the aircraft 1 to which the gas turbine engine 10 is mounted). In some examples, it is located at a point immediately before the fuel is combusted (e.g. before entering the combustor). In yet other examples, the sensor 127 is located at a point within the aircraft fuel supply system e.g. before it enters part of the gas turbine engine 10. Any of the features described above in connection with the example of FIG. 16 may also apply to the example shown in FIG. 17.

In the example shown in FIG. 17, the trace sensor 127 is arranged such that all of the fuel flowing to the combustor 16 passes through it (e.g. it is arranged in series). In other examples, only some of the fuel may pass through the trace sensor 127. For example, the trace sensor may be located in bleed line of the fuel system at which fuel is sampled from the fuel supply to the combustor (e.g. before or after fuel mixing).

Figure 18:
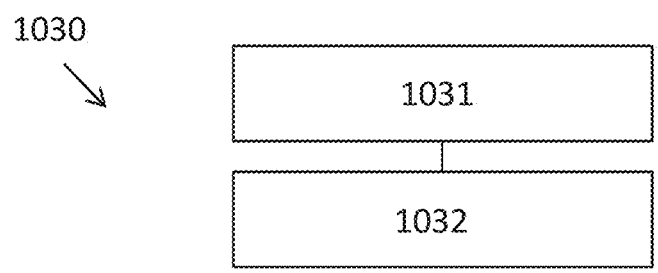
FIG. 18 is a schematic representation of another example of a method of determining fuel characteristics of an aviation fuel.

FIG. 18 illustrates a method 1030 of determining one or more fuel characteristics of an aviation fuel suitable for powering a gas turbine engine of an aircraft that can be performed by the fuel characteristic determination systems 126 shown in FIGS. 15, 16 and 17. The method 1030 comprises: measuring 1031 one or more trace substance parameters of the fuel, the one or more trace substance parameters each associated with a respective trace substance in the fuel; and determining 1032 one or more fuel characteristics of the fuel based on the one or more trace substance parameters. Any of the features described above in connection with FIGS. 15, 16 and 17 can be incorporated in the method of FIG. 18.

UV-Vis Spectroscopy Sensor

Figure 19:
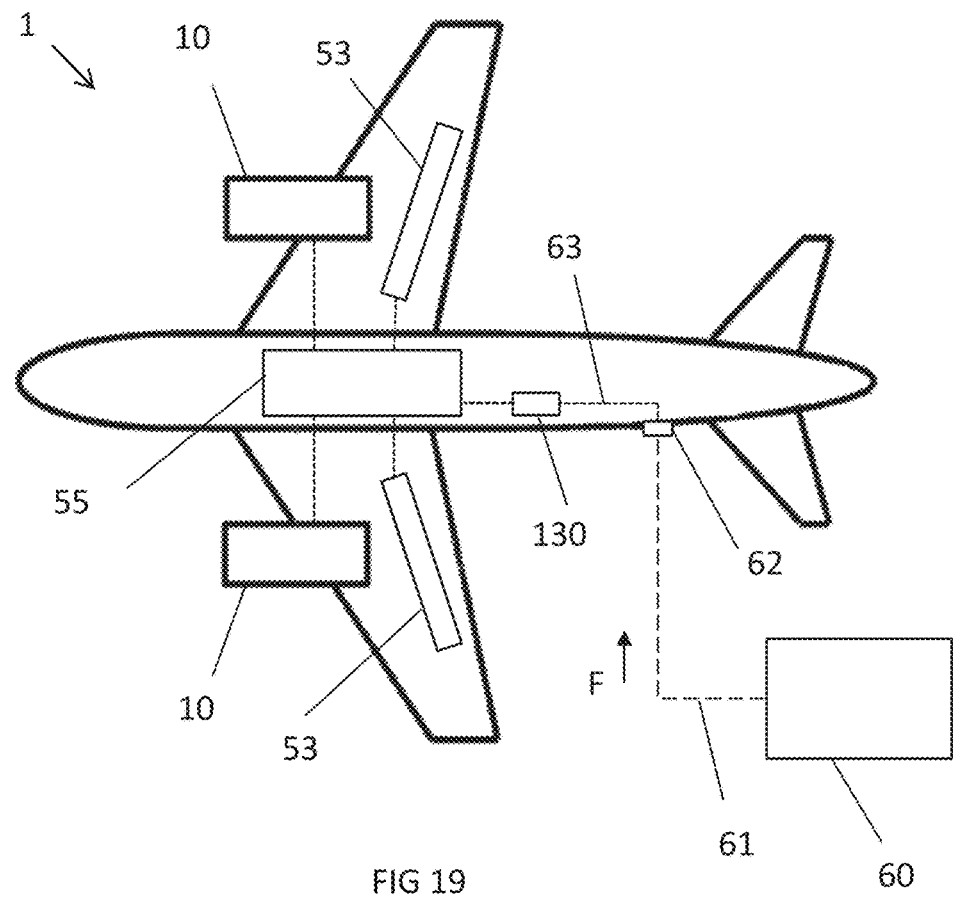
FIG. 19 is a schematic view of an aircraft including another example of a fuel characteristic determination system.

Fuel Characteristic Determination During Refueling Using a UV-Vis Sensor:

Referring to FIG. 19, another example of a fuel characteristic determination system 130 is illustrated, located on board the aircraft 1. The fuel characteristic determination system 130 in this example is arranged to determine one or more fuel characteristics of fuel being loaded onto the aircraft 1, those characteristics being any of those described or claimed herein. In this example, the one or more fuel characteristics are determined based on a measurement of the transmittance of UV and visual spectrum (UV-Vis) light through the fuel.

Figure 20:
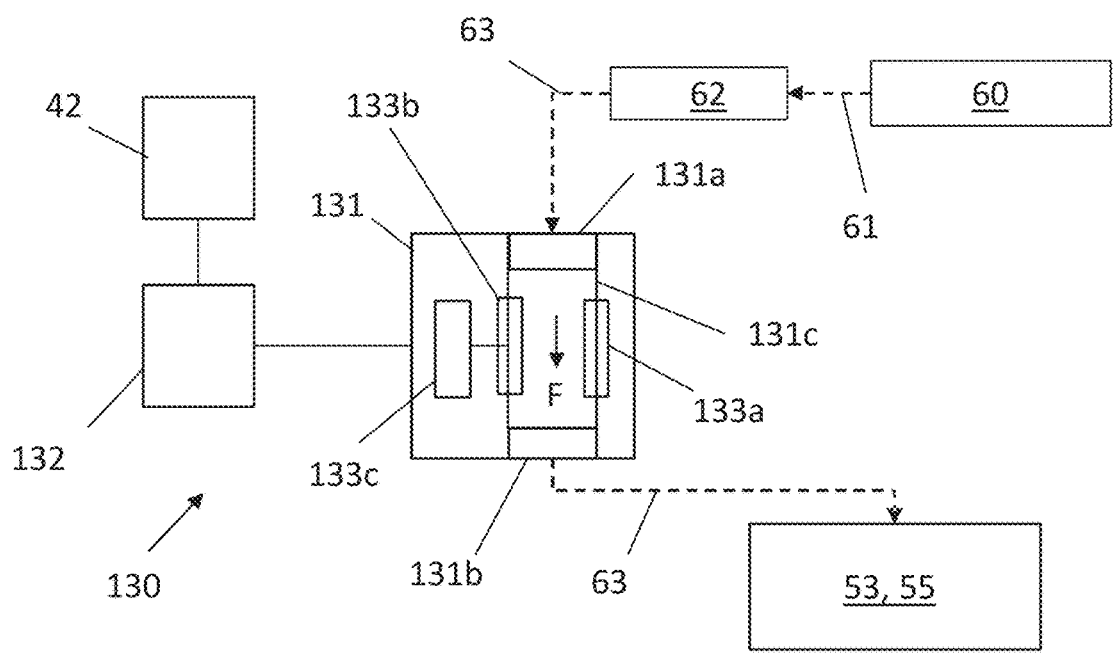
FIG. 20 is a close-up schematic view of the fuel characteristic determination system of FIG. 19.

Further details of the fuel characteristic determination system 130 are illustrated in FIG. 20. The fuel characteristic determination system 130 generally comprises a UV-Vis sensor 131 which is arranged to measure one or more UV transmittance parameters of the fuel being supplied to the aircraft fuel tanks 53, 55.

The fuel characteristic determination system 130 further comprises a fuel characteristic determination module 132 arranged to determine one or more fuel characteristics of the fuel based on the transmittance parameters. The fuel characteristic determination module 132 is arranged to receive the transmittance parameters from the UV-Vis spectrum sensor 131 such that the one or more fuel characteristics can be calculated.

In the example illustrated in FIG. 20, the sensor 131 comprises a UV-Vis spectroscopy device arranged to measure the transmittance of light in the UV and visual spectrum by the fuel. As can be seen in FIG. 20, fuel being loaded onto the aircraft is passed through the sensor 131 where the fuel is irradiated with UV-Vis light. The sensor 131 comprises a fuel inlet 131a and a fuel outlet 131b, and a fuel conduit 131c arranged in fluid communication between them. In the present example, the sensor 131 is located on board the aircraft and is arranged to receive fuel flowing through the fuel transmission line 63 i.e. fuel flowing from the fuel line connection port 62 to the fuel tanks 53, 55.

The UV-Vis spectroscopy device comprises a light source 133a, such as an LED, arc-lamp etc, which is arranged to emit radiation into the fuel F. In some examples, the light source 133a may comprise two or more different individual light sources arranged to provide light over different wavelengths which, when combined, provide the desired UV-Visual spectral range. The UV-Vis spectroscopy device further comprises a detector 133b arranged to detect light transmitted through the fuel from the light source 133a. The detector 133b may comprise a photodiode or similar sensor arranged to detect light emitted by the light source 133a. The detector 133b is in communication with a processor module 133c configured to process a signal from the detector 133c and calculate a transmittance parameter accordingly.

The transmittance parameter defines the amount of absorbance of light at specific wavelengths of light emitted by the light source 133a. The inventors have determined that by measuring a UV-Vis absorption spectrum of the fuel the fuel characteristic determination module can calculate various characteristics of the fuel.

In one example, the one or more fuel characteristics determined by the fuel characteristic determination module 132 may include a hydrocarbon distribution of the fuel. More specifically, they may include the amount of aromatic hydrocarbon content of the fuel. In some examples, other fuel characteristics may be directly determined from the transmittance parameter or inferred or determined therefrom indirectly. For example, the one or more determined fuel characteristics may include the percentage of sustainable aviation fuel in the fuel on which the measurement is performed. As described elsewhere herein, SAF is typically associated with an essentially zero amount of aromatic content. The fuel characteristic determination system 130 may, in this example, compare the measured aromatic compound concentration to that corresponding to fossil derived fuel in order to determine a percentage of SAF in the fuel F being supplied to the aircraft. By measuring a reduction in the aromatic content compared to fossil kerosene, the relative amount of SAF present in the fuel as a percentage of the total fuel (e.g. the percentage SAF per unit mass or volume) can therefore be derived. In some examples, the transmittance parameters may indicate a measurable absence of aromatic compounds within the fuel F, based on which the fuel characteristic determination module 132 may determine that no fossil kerosene is present within the fuel F. In other examples, an indication that the fuel is fossil kerosene may be determined.

In order to determine the one or more fuel characteristics, the determination module 132 may be arranged to compare a measured transmittance parameter to a look-up table of expected parameter values of fuels with known fuel characteristics to determine the corresponding characteristics of the fuel to which the transmittance is measured. This may allow a range of fuel characteristics to be determined based on the transmittance signature as a function of wavelength being compared to those of known fuel types.

In the present example, the UV-Vis sensor 131 is arranged such that all of the fuel flowing through the transmission line 63 is input to the sensor inlet 131a, flows through the fuel conduit 131c, and is output via the fuel outlet 131b to continue to the fuel tanks (i.e. the sensor is connected in series between the fuel line connection port 62 and the fuel tanks). In other examples, the sensor 131 may be connected in parallel such that only some of the fuel is redirected from the transmission line 63, flows through the sensor, and then is returned to the fuel transmission line 63 or to the fuel tanks. In some examples, the sensor 131 may be a microfluidic (lab-on-chip) device through which a small sample of fuel may be passed to perform a UV-vis spectroscopy measurement.

The determination module 132 is arranged to communicate the determined one or more fuel characteristics to a control module of the gas turbine engine or the aircraft. In the presently described example, the one or more fuel characteristics are transmitted to the electronic engine controller EEC 42. In some examples, the determination module 132 may be part of the EEC 42 of any one or more of the gas turbine engines of the aircraft, with the control module being a sub-module of the EEC. Once received at the EEC the fuel characteristics can be used to provide information on the fuel that is being provided from the fuel tanks to the engine such that operation of the gas turbine engine(s) can be adapted accordingly. In yet other examples, the determination module 132 may be part of the sensor unit 131, which is in communication with the EEC.

In the examples described above the fuel characteristic determination system 130 is located on board the aircraft 1 so that fuel within the fuel transmission line 63 flow through it before reaching the fuel tanks 53, 55. In other examples, the fuel characteristic determination system 130 may be arranged to use fuel within, or sampled from, one of the fuel tanks 53, 55. In such an example, the UV-Vis sensor 131 may be located within a fuel tank so that a fluorescence or spectroscopy measurement may be performed (or other suitable measurement depending on the trace substance detected). The UV-Vis sensor 131 may therefore be built into an interior wall of the fuel tank such that it is exposed to fuel within the tank. In other examples, fuel may be sampled from the tank and passed through the sensor 131.

In other examples, the fuel characteristic determination system 130, or at least part of it, may be located separately from the aircraft 1. For example, it may be included in the fuel loading line 61 so that it may detect properties of the fuel before it reaches the aircraft. In some examples, the UV-Vis sensor 131 may be located within the fuel loading line, or elsewhere separately from the aircraft 1, and arranged to transmit a transmittance parameter to a determination module 132 located on board the aircraft 1, where it can be communicated to a control module of the engine (e.g. the EEC). In yet other examples, the fuel characteristic determination system 130 may be located entirely outside of the aircraft. In such an example, the fuel characteristic determination module may determine a fuel characteristic which is then communicated to the aircraft 1 (e.g. to a control module of the engines or engines 10). In this example, a data transfer link may be provided (e.g. a wireless or wired data connection) and may be used to communicate the fuel characteristics to the aircraft from the fuel characteristic determination system 130. In some examples, the data transfer may be done manually by a user, e.g. a technician or other operator of the system may obtain the fuel characteristics from the determination system 130 and manually provide them to a control module on board the aircraft.

Figure 21:
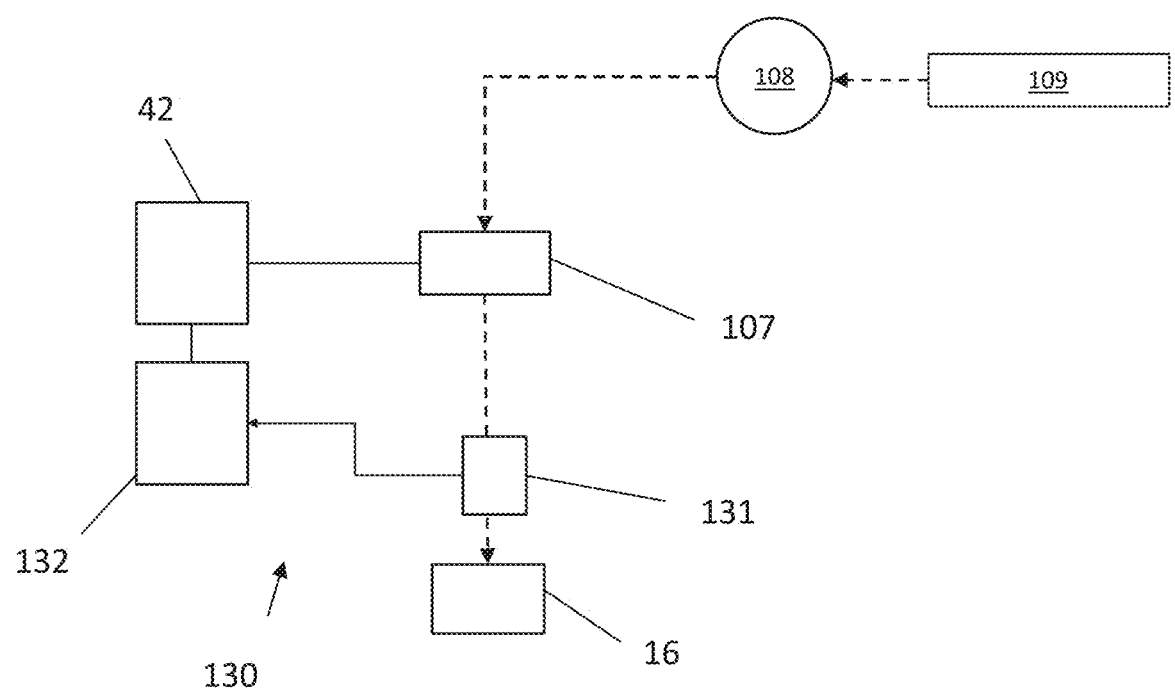
FIG. 21 is schematic view of another example of a fuel characteristic determination system provided within a fuel system of a gas turbine engine.

Fuel Characteristic Determination within the Engine Using UV-Vis Sensor:

FIG. 21 illustrates another example of the fuel characteristic determination system 130 described above. The fuel characteristic determination system 130 of FIG. 21 similarly comprises a UV-Vis sensor 131 and determination module 132 arranged to measure one or more fuel characteristics based on a transmittance parameter.

FIG. 21 shows a schematic view part of the fuel system of the aircraft and the combustion equipment 16 of the gas turbine engine 10. The combustion equipment 16 comprises a plurality of fuel nozzles (not shown in FIG. 21) arranged to inject fuel into a combustion can. Fuel is provided to the combustion equipment 16 by a fuel delivery regulator 107 under the control of the EEC 42. Fuel is delivered to the fuel delivery regulator 107 by a fuel pump 108 from a fuel source 109 on board the aircraft 1 (e.g. one or more fuel tanks as described above). The fuel delivery regulator 107 and combustion equipment 16 may be of known design, and may be arranged for staged (lean-burn) combustion or rich-burn combustion.

In this example, a transmittance parameter is measured for fuel as it is being used by the engine. The UV-Vis sensor 131 in this example is arranged to measure a transmittance parameter at any point within the fuel system of the aircraft that is upstream of the combustion equipment 16 (e.g. upstream of the fuel nozzles of the combustion equipment 16) and downstream of the fuel source 109 from which the fuel is supplied (e.g. downstream of the one or more fuel tanks 53, 55 forming the fuel source). In some examples, the UV-Vis sensor 131 is located at a point within the engine fuel system such as in a fuel conduit within or forming part of the gas turbine engine 10 (rather than being on the aircraft 1 to which the gas turbine engine 10 is mounted). In some examples, it is located at a point immediately before the fuel is combusted (e.g. before it enters the combustor). It may, for example, be included in a bleed line of the engine fuel system (e.g. before or after fuel mixing). In yet other examples, the UV-Vis sensor 131 is located at a point within the aircraft fuel supply system e.g. before it enters part of the gas turbine engine 10. Any of the features described above in connection with the example of FIG. 20 may also apply to the example shown in FIG. 21.

Figure 22:
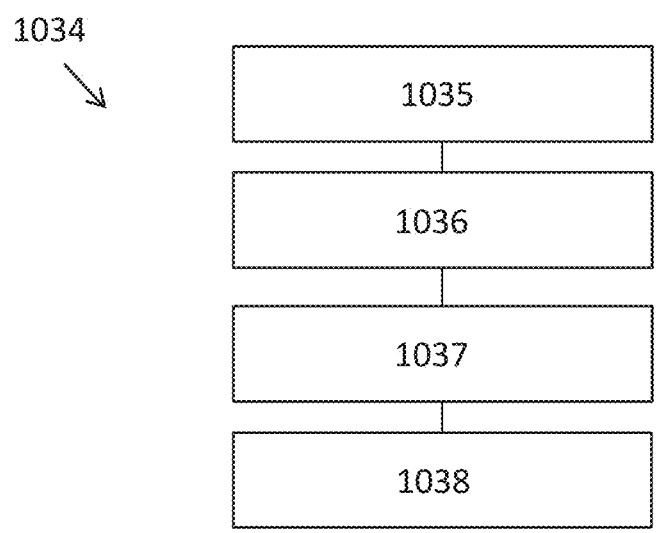
FIG. 22 is a schematic representation of another example of a method of determining fuel characteristics of an aviation fuel.

FIG. 22 illustrates a method 1034 of determining one or more fuel characteristics of an aviation fuel suitable for powering a gas turbine engine of an aircraft. The method 1034 can be performed by the fuel characteristic determination systems 130 shown in FIGS. 19, 20 and 21. The method 1030 comprises passing 1035 UV-visual spectrum light through the fuel and measuring 1036 a transmittance parameter indicating the transmittance of light through the fuel. The method further comprises determining 1037 one or more fuel characteristics of the fuel based on the transmittance parameter. Once the fuel characteristic is determined, the method 1034 comprises communicating 1038 the one or more fuel characteristic to a control module of the gas turbine engine. Any of the features described above in connection with FIGS. 19, 20 and 21 can be incorporated in the method of FIG. 22.

Fuel Characteristic Determination Using Contrail Measurement

Figure 23:
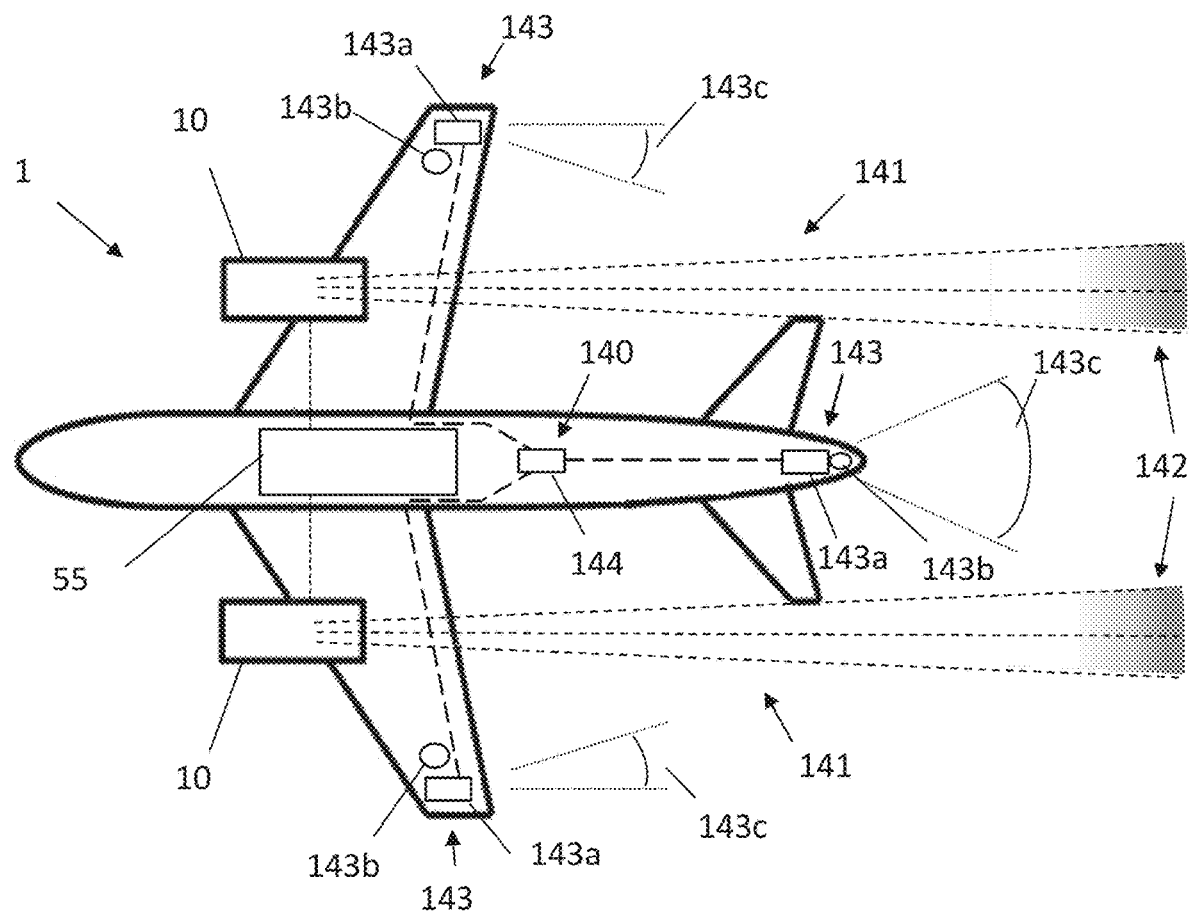
FIG. 23 is a schematic view of an aircraft including another example of a fuel characteristic determination system.

FIG. 23 illustrates another example of a fuel characteristic determination system 140, located on board the aircraft 1. The fuel characteristic determination system 140 in this example is arranged to determine one or more fuel characteristics of fuel based on observations of contrail formation. FIG. 23 shows the aircraft 1 in flight with each gas turbine engine 10 producing an exhaust plume 141. A contrail 142 is also formed in the exhaust plume 141 of each engine 10. The wing fuel tanks of the aircraft 1 are not shown in FIG. 23 to aid clarity, but it is to be understood that these may still be present.

The fuel characteristic determination system 140 comprises a contrail sensor 143 and a fuel characteristic determination module 144. In the present example, the fuel characteristic determination system 140 comprises three contrail sensors 143, one located on each wing of the aircraft 1 and one on the aircraft empennage or tail assembly. In other examples, only one or another number of contrail sensors may be provided as described later. The contrail sensors are each arranged to determine one or more contrail parameters related to contrail formation by the gas turbine engine 1. The contrail sensors 143 are arranged to perform a sensor measurement on a region behind each gas turbine engine 10 of the aircraft 1 in which a contrail 142 is or can be formed, e.g. the exhaust plumes 141 of each engine 10.

The contrail parameters measured by the control sensors 143 include a measured value corresponding to the degree of contrail formation taking place within the exhaust plume 141. In some examples, this may be an indication of the presence or the absence of a contrail 142 in the respective exhaust plume 141 of each engine 10. In other examples, the contrail parameters may be a variable indicating the relative amount of contrail that is being formed ranging between no contrail and a maximum degree of contrail formation.

The contrail sensors 143 are in communication with the fuel characteristic determination module 144, which is arranged to receive the contrail parameter(s) from each sensor 143. The fuel characteristic determination module is arranged to determine one or more characteristics of the fuel based on the contrail parameters received.

The inventors have observed that the presence of a contrail, or the degree to which a contrail is formed, is dependent (at least in part) on the characteristics of the fuel being burnt by the combustor of the engines 10. The inventors have determined that the characteristics of the fuel can be determined based on an active measurement of the contrail formation in the exhaust plume of a respective gas turbine engine 10.

In one example, the one or more fuel characteristics determined based on the measured control parameter(s) include a hydrocarbon distribution of the fuel. More specifically, they may include an aromatic content of the fuel. The inventors have determined that the formation of a contrail is dependent on the presence of aromatic molecules in the fuel being used. The inventors have determined that a reduction of aromatic content of the fuel results in an increase in the susceptibility of an engine to the formation of contrails since the lower aromatic content of the fuel means that the ratio of water-vapour-to-heat added by the engine to the exhaust plume is increased. This enables the formation of contrails over a wider range of atmospheric conditions compared to fuels with a higher aromatic content such as fossil kerosene. Furthermore, less aromatic content may mean fewer emitted soot particles, which should (in most situations) lead to fewer (and hence individually larger) ice particles in the young contrail.

In some examples, the one or more contrail parameters may include measurements made by the control sensors 143 over a prolonged duration of time (rather than an instantaneous observation of a contrail). In some examples, the one or more control parameters may include a prolonged observation straddling the boundary between contrail-forming conditions and non-contrail forming conditions (or vice versa).

In some examples, other fuel characteristics as defined or claimed elsewhere herein may be determined based on the contrail parameters. In some examples, the SAF content of the fuel may be determined based on the contrail parameters. As the aromatic content of a SAF is typically lower compared to fossil kerosene fuel, the resulting contrail formation will therefore be different, and allow a determination of the SAF content of the fuel to be determined. In other examples, the one or more fuel characteristics determined may include an indication that the fuel is fossil kerosene. This may be determined as a result of the measured contrail parameters corresponding to that which would be expected if fossil kerosene were being combusted by the gas turbine engine. In other examples, the hydrocarbon distribution of the fuel may be determined or inferred based on the contrail parameters, for example by reference of the contrail parameters to those expected for a fuel with a known hydrocarbon distribution. The fuel characteristics may be determined using similar comparison of parameters to those of known fuel types.

In the example illustrated in FIG. 23, each of the contrail sensors 143 comprise a contrail detector 143a arranged to detect electromagnetic radiation reflected and/or re-emitted by a contrail 142. Each contrail sensor further comprises a source of illumination 143b arranged to emit radiation that is incident upon the contrail 142 where it is reflected and/or re-emitted and detected by the detector 143a. In other examples, any of the detectors 143a may be arranged to respond to electromagnetic radiation reflected and/or re-emitted by a contrail 142 in response to ambient illumination (e.g. sunlight), or alternatively in response to infra-red (or other) illumination emitted by the hot exhaust of the engine. In such examples, the sources of illumination 143b may be absent. The radiation detected by the detectors 143a may be infra-red wavelength radiation emitted or reflected by a contrail. In other examples, other wavelengths of radiation may be detected.

The sensors 143 each have a field of view 143c in which a signal from a contrail may be received. The sensors may be provided at any suitable location on the aircraft such so that the contrail forming region is in the sensor field of view. In the present example, sensors 143 are located on the aircraft wings and empennage. Other sensor locations may however be provided to observe each exhaust plume separately or together.

In yet other examples, other forms of sensor may be used to measure a contrail parameter indicative of the presence or absence of a contrail, or degree to which a contrail is formed. In some examples, the contrail sensors 143 may be arranged to detect sound returned from particles in a contrail. For example, the sources of illumination may be replaced with sources of sound (or ultrasonic) waves, which could comprise the sound generated by the engine in use. The detectors 143a would then be arranged to detect the sound returned from the ice particles in a contrail.

In yet other examples, the sensors 143 may be image sensors. In this example, the sensors may comprise an imaging device arranged to obtain in an image of the exhaust plume (e.g. at a location where a contrail may form behind the gas turbine engines), and determine from the image whether or not a contrail is formed, or the degree to which a contrail has formed. This may be done using image processing techniques or an AI (artificial intelligence) algorithm configured to measure the size and shape of any contrail formed, or if a contrail is absent in the images obtained.

The fuel characteristic determination module 144 is arranged transmit the determined one or more fuel characteristics to the electronic engine controller EEC 42 (not shown in FIG. 23). In some examples, the determination module 144 may be part of the EEC 42 of any one or more of the gas turbine engines of the aircraft. Once received at the EEC the fuel characteristics can be used to provide information on the fuel that is being provided from the fuel tanks to the engine such that operation of the gas turbine engine(s) can be adapted accordingly. In yet other examples, the fuel characteristic determination module 144 may be part of one of the sensors 143, which is in communication with the EEC.

In order to determine the one or more fuel characteristics, the determination module 144 may be arranged to compare a measured contrail parameter to a look-up table of expected contrail parameter values of fuels with known fuel characteristics to determine the corresponding characteristics of the fuel being used by the gas turbine engines.

In some examples, the one or more fuel characteristics are further determined by the fuel characteristic determination module 144 based on one or more an ambient atmospheric condition parameters. Each of these atmospheric condition parameters is indicative of the ambient atmospheric conditions in which the gas turbine engines 10 are currently operating. The inventors have determined that the formation of a contrail is at least partly dependent on the atmospheric conditions in which the respective engine is operating, in additional to the characteristics of the fuel being combusted. The atmospheric condition parameters may include the ambient pressure, temperature and/or vapour pressure (humidity) in which the gas turbine engine is operating. By further taking the ambient conditions into account the determination of the fuel characteristics may be improved.

In some examples, the ambient atmospheric condition parameters may be obtained from a sensor or sensors located on board the aircraft, which are arranged to measure the conditions in the vicinity of the aircraft. This may provide a direct measurement of the current conditions in which the engine is operating. In other examples, the ambient condition parameters may be obtained from a source of meteorological data providing real-time or expected information on the ambient conditions in which the engine is operating.

In some examples, the one or more fuel characteristics are further determined based on one or more engine or aircraft operating parameters. Various operating parameters of the aircraft or engine may have a bearing on whether a contrail is formed and may therefore be taken into account.

In some examples, the fuel characteristic may be calculated by determining the value of a varying parameter (e.g. engine operating parameter and/or ambient condition parameter) at which a contrail is first formed.

In one example, the one or more fuel characteristics may be determined based on a contrail parameter measured during a climb phase of engine operation. For example, the contrail parameter may indicate when a contrail first starts to form during a climb phase, and along with the ambient conditions and engine operating parameter at which the contrail begins to form, one or more characteristics of the fuel can be determined. This may be used to infer fuel properties, particularly the amount of water vapour released by combustion per unit of fuel energy, which in turn is related to fuel characteristics such as the hydrogen mass fraction of the fuel.

Figure 24:
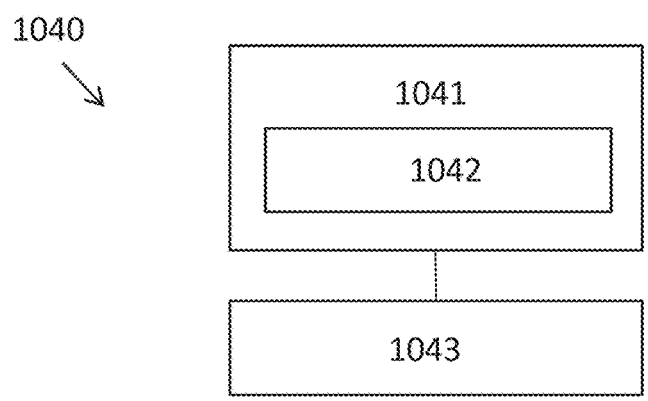
FIG. 24 is a schematic representation of another example of a method of determining fuel characteristics of an aviation fuel.

FIG. 24 illustrates a method 1040 of determining a fuel characteristic of an aviation fuel suitable for powering a gas turbine engine of an aircraft that can be performed by the fuel characteristic determination system 140 shown in FIG. 23 and described above. The method 1040 comprises determining 1041, during use of the gas turbine engine 10, one or more contrail parameters. The contrail parameters are related to contrail formation by the gas turbine engine 10 as described above. For example, the contrail parameters may include a parameter indicative of the degree of contrail formation taking place, or whether a contrail is present or absent. Determining 1041 the one or more contrail parameters comprises performing 1042 a sensor measurement on a region (e.g. exhaust plume 141) behind the gas turbine engine in which a contrail 142 is or can be formed. The method further comprises determining 1043 one or more fuel characteristics of the fuel based on the one or more contrail parameters as described above. Any of the features described above in connection with FIG. 23 may be incorporated into the method of FIG. 24.

Fuel Characteristic Determination Using Exhaust Measurement

Figure 25:
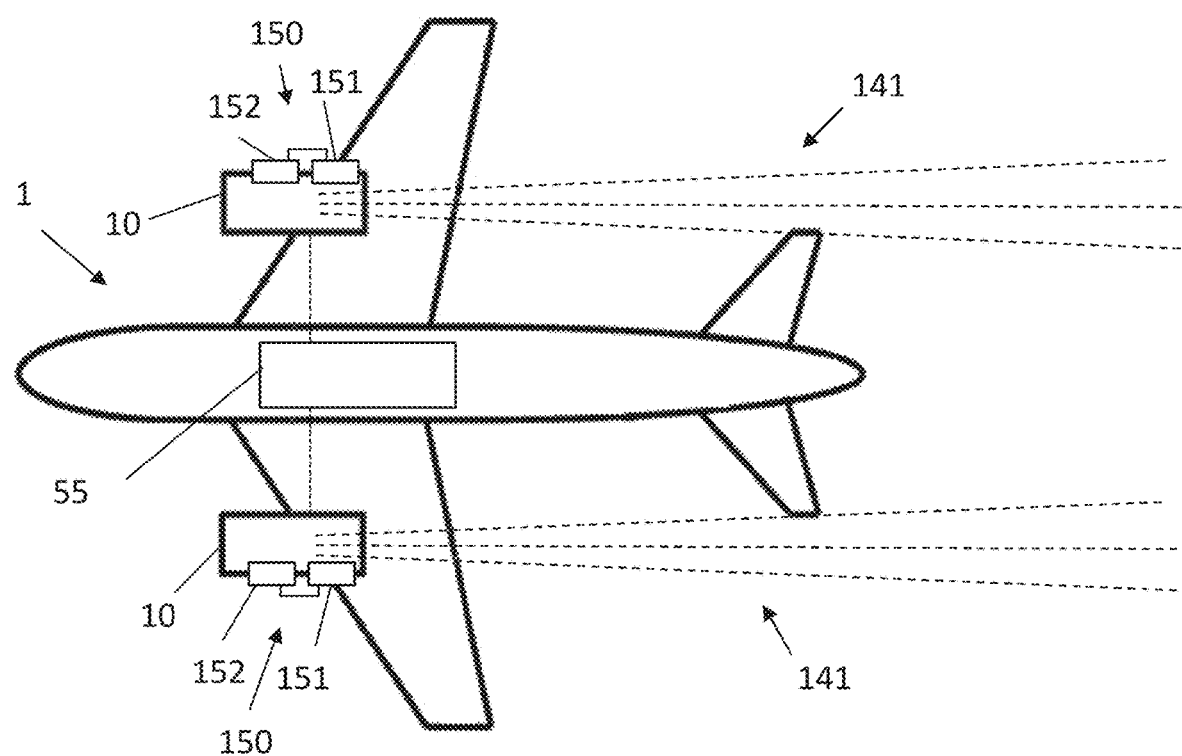
FIG. 25 is a schematic view of an aircraft including another example of a fuel characteristic determination system.

FIG. 25 illustrates another example of a fuel characteristic determination system 150, located on board the aircraft 1. The fuel characteristic determination system 150 in this example is arranged to determine one or more fuel characteristics of the fuel being supplied to a gas turbine engine based on measurements of an exhaust of that engine 10. FIG. 25 shows the aircraft 1 in flight with each gas turbine engine 10 producing an exhaust plume 141. The wing fuel tanks of the aircraft 1 are not shown in FIG. 25 to aid clarity, but it is to be understood that these may still be present.

The determination system 150 comprises an exhaust sensor 151 and a fuel characteristic determination module 152. In the example shown in FIG. 25, a fuel characteristic determination system 150 is provided for each engine, but in other examples a single fuel characteristic determination system 150 could be shared between them, with exhaust sensor(s) 151 for each engine 10 providing information to the single determination module 152.

The exhaust sensor 151 is arranged to determine one or more exhaust content parameters of the exhaust produced by the respective gas turbine engine 10. The exhaust sensor is arranged to perform a measurement of exhaust being produced by the engine during use. This may include at engine operating conditions corresponding to any flight phase (e.g. during cruise), or corresponding to operation while the aircraft is on the ground (e.g. during start-up or taxi). The exhaust content parameters may be indicative of the chemical content of the exhaust being produced by the engine, and may indicate the concentration, presence or absence of respective substances or species in the exhaust. In some examples, the exhaust sensor(s) 151 may be located within the respective gas turbine engine 10 so that it is arranged to perform a measurement on exhaust gas before it is emitted by the engine. In some examples, the exhaust sensor may perform a measurement on exhaust gases as they flow through the engine core, or alternatively which are sampled from the core flow. In other examples, the exhaust sensor 151 may be arranged to perform a measurement on exhaust gases once they have exited the engine e.g. via the core exhaust nozzle 20 (as shown in FIG. 1).

The exhaust sensor 151 is in communication with the fuel characteristic determination module 152, which is arranged to receive the exhaust content parameter(s) therefrom. The fuel characteristic determination module 152 is then arranged to determine one or more characteristics of the fuel based on the exhaust content parameters received.

The inventors have determined that characteristics of the fuel being provided to the gas turbine engine and combusted by its combustor can be determined during operation of the engine by active measurement of the properties of the exhaust being produced. In this example, the exhaust content parameters include properties of the exhaust other than the presence of a contrail.

In one example, the one or more exhaust content parameters include a parameter indicative of the nvPM content of the exhaust. The inventors have determined that by actively measuring the nvPM content of the exhaust various characteristics of the fuel F can be determined. By measuring the nvPM content, for example, a hydrogen to carbon ratio of the fuel F being combusted can be determined. The inventors have observed that a lower hydrogen to carbon ratio (e.g. compared to fossil kerosene) is associated with a higher level of nvPM production, and the dependence between them can be used to determine the characteristic of the fuel.

In another example, a naphthalene content can be determined based on the measured nvPM content. In this example, a high naphthalene content (e.g. in comparison to fossil kerosene fuel) is associated with a higher level of nvPM production. This dependence between nvPM production and naphthalene content can be used to determine the naphthalene content of the fuel F.

In yet another example, an aromatic content (e.g. aromatic mass fraction) of the fuel F can be determined based on the measured nvPM content. In this example, a high aromatic content (e.g. in comparison to fossil kerosene fuel) is associated with a higher level of nvPM production. This dependence between nvPM production and aromatic content can be used to determine the aromatic content of the fuel F.

In order to measure the nvPM content of the exhaust, the exhaust sensor 151 may in one example comprise a laser induced incandescence (LII) measurement device arranged to determine the volume concentration of nvPM in the exhaust. The LII measurement device may be arranged to fire a very short, high energy pulse of a 1064 nm laser at particles within the exhaust. This results in the nvPM particles heating up and glowing in the visible spectrum. The peak glow is directly related to volume concentration of nvPM. The material density can then also be used to convert to nvPM mass concentration.

In other examples, the exhaust sensor 151 may comprise a condensation particle count (CPC) measurement device arranged to determine an nvPM number in the exhaust. The CPC device is arranged to count particles using laser scattering after the particles have been increased in size by passing them through a cloud of butanol vapour. This condenses to make the particles large enough to count using a laser scattering measurement. In this example, a volatile particle remover may be required upstream of the CPC measurement device to remove any volatile particles from the exhaust.

In addition, or alternatively to the nvPM content, the one or more exhaust content parameters may include a parameter indicative of $SO_2$, $CO_2$ or CO gas within the exhaust. Based on a measurement of the $SO_2$ content of the exhaust, the elemental sulphur content of the fuel can be determined by the fuel characteristics determination module. For example, because the $SO_2$ content of the exhaust will stem from oxidation of the fuel's sulphur content. Similarly, based on a measurement of $CO_2$ or CO in the exhaust, the fuel characteristic determination module may determine the carbon content within the hydrocarbon content of the fuel. The carbon content can be determined based on the oxidation of the fuel's carbon content. In other examples, the exhaust content parameters be indicative of the sulphate aerosol content of the exhaust. These exhaust content parameters may be used to determine a sulphur content fuel characteristic of the fuel F.

In order to measure the $SO_2$, $CO_2$ or CO gas content of the exhaust, the exhaust sensor 151 may comprise a non-dispersive infra-red absorption (NDIR) measurement device. In order to measure the sulphate aerosol mass content of the exhaust, the sensor 151 may comprise an aerosol mass spectrometer (AMS) device. The AMS device may be arranged to direct aerosols onto a hot plate (e.g. at 600° C.) and measure a resulting molecular mass spectrum. The AMS device may be arranged to sum all of the spectrum peaks associated with sulphates. This method misses the sulphur nucleation peak if one exists in the cooled plume. Particle size (electrical mobility) distributions may be measured either by Scanning Mobility Particle Sizer (SMPS) type measurement or Differential Mobility Particle Sizer (DMS) type measurement can determine a sulphur nucleation peak ~10 nm. The AMS measurement may be done using a cooled sample of exhaust gas from the engine exhaust.

The types of exhaust sensors given above are intended to be examples only, and other types of sensor can used to determine nvPM and sulphur content of the exhaust. In yet other examples, other exhaust content properties may be determined, using appropriate sensors, in order for various other fuel characteristics to be determined (e.g. any of those defined elsewhere herein).

In some examples, other fuel characteristics as defined or claimed elsewhere herein may be determined based on the exhaust parameters. In some examples, the SAF content of the fuel may be determined based on the exhaust parameters. As, for example, the aromatic content of a SAF is typically lower compared to fossil kerosene fuel the resulting exhaust properties (e.g. nvPM content) will therefore be different, and allow a determination of the SAF content of the fuel to be made. In other examples, the one or more fuel characteristics determined may include an indication that the fuel is fossil kerosene. This may be determined as a result of the measured exhaust content parameters corresponding that that which would be expected if fossil kerosene were being combusted by the gas turbine engine.

In order to determine the one or more fuel characteristics, the determination module 152 may be arranged to compare a measured exhaust parameter or parameters to a look-up table of expected exhaust parameter values of fuels with known fuel characteristics to determine the corresponding characteristics of the fuel being used by the gas turbine engines. For example, the measured exhaust parameters may be compared to a base-line that would be expected for a fuel of known characteristics, such as kerosene or Jet A-1 standard fuel.

In some examples, the one or more fuel characteristics are further determined by the determination module 152 based on one or more ambient atmospheric condition parameters. Each of the atmospheric condition parameters is indicative of the ambient atmospheric conditions in which the gas turbine engine is currently operating. The inventors have determined that the exhaust properties are at least partly dependent on the atmospheric conditions in which the engine is operating, in addition to the characteristics of the fuel being combusted. The atmospheric condition parameters may include the ambient pressure, temperature and/or vapour pressure (humidity) in which the gas turbine engine is operating. By further taking the ambient conditions into account the determination of the fuel characteristics may be improved.

In some examples, the ambient atmospheric condition parameters may be obtained from a sensor or sensors on board the aircraft which are arranged to measure the conditions in the vicinity of the aircraft. This may provide a direct measurement of the current conditions in which the engine is operating. In other examples, the ambient condition parameters may be obtained from a source of meteorological data providing real-time or expected information on the ambient conditions in which the engine is operating.

In some examples, the one or more fuel characteristics are further determined based on one or more engine or aircraft operating parameters. The engine operating parameters may, for example, include the power setting of the engine.

The exhaust content parameters may be measured at any time during operation of the aircraft. In some examples, exhaust content parameters may be measured during an operating stage before take-off of the aircraft so that a fuel parameter can be determined for later use during operation of the gas turbine for that specific flight. In some examples, the exhaust content parameters may be measured during a start-up or taxi phase of operation of the engine.

In yet other examples, the exhaust content parameters may be measured at a first engine operation condition which is associated with high levels of emission of the relevant substance in the exhaust being produced, compared to an engine operation condition where they would be expected to be lower. For example, if the exhaust content parameters relate to the nvPM content of the exhaust, they may be measured during a phase of operation of the engine in which the nvPM production is expected to be inherently high relative to other low-nvPM emission phases. The first engine operation condition may, for example, be a low engine power, compared to a second operating condition which may be a relatively higher engine power operating condition.

In some examples, the fuel characteristic determination module 152 may base the fuel characteristic determination on a comparison of exhaust content parameters measured at different operating conditions of the engine. For example, the fuel characteristic determination may be based on a comparison of exhaust content parameters measured at different engine power levels.

Figure 26:
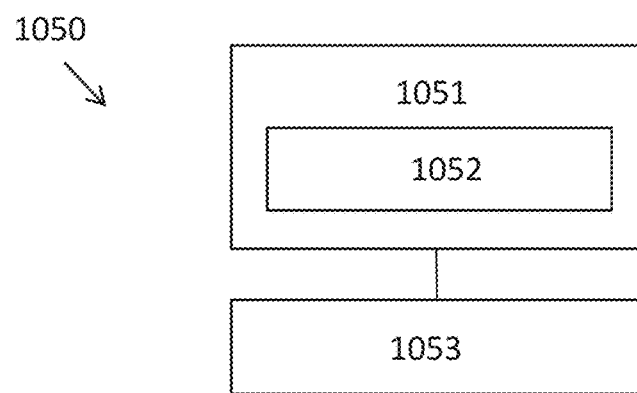
FIG. 26 is a schematic representation of another example of a method of determining fuel characteristics of an aviation fuel.

FIG. 26 illustrates a method 1050 of determining a fuel characteristic of an aviation fuel suitable for powering a gas turbine engine of an aircraft that can be performed by the fuel characteristic determination system 150 shown in FIG. 25 and described above. The method 1050 comprises determining 1051, during use of the gas turbine engine 10, one or more exhaust content parameters. The one or more exhaust parameters are determined by performing 1052 a sensor measurement on an exhaust of the gas turbine engine 10 as described above. The method 1050 further comprises determining 1053 one or more fuel characteristics of the fuel based on the one or more exhaust parameters.

The method 1050 may comprise measuring the exhaust content parameters at a first engine operation condition in which emission of the respective substance being measured is greater than in at a second engine operation condition. The first engine operation condition may correspond to a lower engine power compared to the second. In yet other examples, the one or more fuel characteristics may be determined based on a comparison of exhaust content parameters determined at different engine operating conditions (e.g. the first and second engine operating conditions).

Fuel Characteristic Determination Using Engine Performance Measurements

Figure 27:
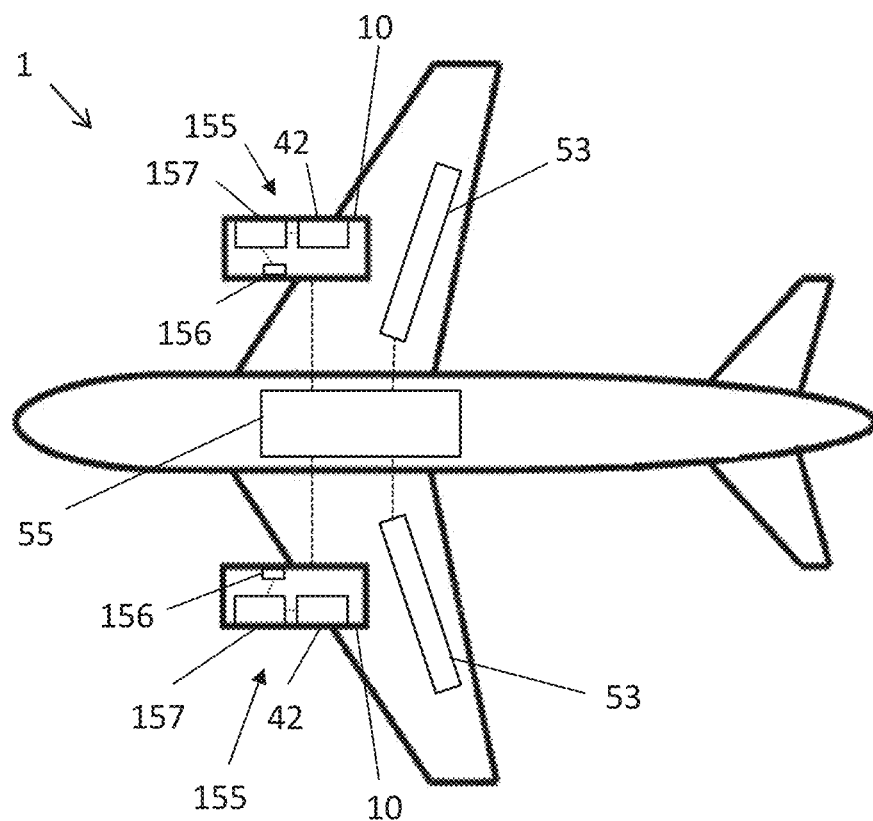
FIG. 27 is a schematic view of an aircraft including another example of a fuel characteristic determination system.

FIG. 27 illustrates another example of a fuel characteristic determination system 155, located on board the aircraft 1. The fuel characteristic determination system 155 in this example is arranged to determine one or more fuel characteristics of the fuel being supplied to a gas turbine engine of the aircraft based on measurements of performance parameters of that engine 10.

The determination system 150 comprises a performance parameter sensor 156 and a fuel characteristic determination module 157. In the example shown in FIG. 27, a fuel characteristic determination system 155 is provided for each engine, but in other examples a fuel single fuel characteristic determination system 155 could be shared between them, with performance parameter sensor(s) 156 for each engine 10 providing information to the single determination module 157.

The fuel characteristic determination module 157 is arranged to determine one or more performance parameters of the respective gas turbine engine 10 measured during a first period of operation of the engine (e.g. during operation at a first engine operating condition). The performance parameters may be obtained from a measurement performed by the sensor 156. In the described example, the fuel characteristic determination module 157 is arranged to obtain the performance parameters directly from the sensor 156. In other examples, the sensor 156 may be in communication with the EEC 42 of the engine 10, and may be used as part of an existing engine control process. The fuel characteristic determination module 157 may, in such an example, obtain performance parameters from the EEC 42. This may allow the fuel characteristic determination system 155 to make use of existing sensors already provided on the gas turbine engine 10. While FIG. 27 shows the fuel characteristic module 157 being separate from and in communication with the EEC 42, it may in some examples be part of the EEC.

The one or more fuel characteristics may be determined by the fuel characteristic determination module 157 after being received from the sensor 156. The fuel characteristics may, in some examples, be determined during a second later period of operation (e.g. during operation at a second engine operating condition, different from the first) after they have been collected during the first period of operation. In other examples, the determination may be made during the first period of operation. The inventors have determined that certain performance parameters of the engine will have a dependence on the characteristics of the fuel being used, and that this can be used to determine various fuel characteristics.

The first period of operation in which the performance parameters are measured may be a first flight phase, for example a take-off or climb phase. The second period of operation in which one or more fuel characteristics may then be determined (and optionally acted upon by controlling the engine accordingly) may be a second flight phase which occurs later in an operating mission or flight compared to the first. The second flight phase may be a cruise phase. By using performance parameters measured during take-off or climb the engine may be operating at an engine operating condition in which a larger variation in performance resulting from the fuel characteristics can be observed. For example, during the climb phase, a variable inlet guide vane (VIGV) of the engine may be in a maximum open state, which would correspond to a greater observable dependence of performance on fuel characteristics.

Various engine performance parameters may be measured by the sensor(s) 156. The performance parameters may be determined directly by a sensor measurement, or may be determined indirectly from a dependence on another parameter. In order to determine the one or more fuel characteristics, the fuel characteristic determination module 157 may be arranged to compare a measured performance parameter to a look-up table of expected performance parameter values corresponding to fuels with known fuel characteristics at the corresponding engine operating condition to determine the characteristics of the fuel being used. For example, the measured performance parameters may be compared to a base-line that would be expected for a fuel of known characteristics, such as kerosene or Jet A-1 standard fuel.

Various fuel characteristics as defined or claimed elsewhere herein may be determined based on the performance parameters in this way. In some examples, the SAF content of the fuel may be determined based on the performance parameters. In other examples, the one or more fuel characteristics determined may include an indication that the fuel is fossil kerosene. This may be determined as a result of the measured performance parameters corresponding to that which would be expected if fossil kerosene were being combusted by the gas turbine engine.

In one example, the performance parameters provided to the fuel characteristic determination module 157 may include the rotational speed of the fan 23 and the rate of fuel being delivered to the engine. The rotational speed of the fan 23 may be determined by the N1 low pressure turbine/compressor rotation speed, which will be the same as the fan speed 23 for a non-geared architecture, or linked to the fan speed by the gear ratio of the gearbox 30. The variation of fan speed with fuel characteristics may relate to the different fuel energy per unit volume and/or per unit mass of different types of fuel. The fuel system of the engine comprises a fuel flow meter arranged to measure the rate (e.g. by mass or by volume) at which fuel is being delivered to the engine, which if combined with knowledge of the resulting fan speed can allow how much benefit the fuel is providing (i.e. more fuel energy per unit time results in a faster fan speed) to be determined. Based on the fan speed and fuel flow rate, the fuel characteristic determination module may be arranged to calculate how much fuel energy is being put into the combustor per unit mass or per unit volume of fuel flow, and thus infer characteristics of the fuel e.g. whether the fuel being provided is SAF, fossil or a percentage blend of the two (i.e. determine the percentage SAF content).

In other examples, the performance parameters provided to the fuel characteristics determination module 157 may include a turbine entry temperature (TET). The TET may be as defined elsewhere herein, and may in this example measured at the first rotor of the first turbine 17 in a downstream direction from the combustor 16 (e.g. at the highest pressure turbine). The TET may be measured directly, or more in some examples be measured indirectly based on a measurement further downstream in the core airflow, for example at the second turbine 19. The inventors have determined that the calorific value of the fuel being burnt by the combustor has an effect on the TET. A measurement of the TET can therefore be used by the fuel characteristic determination module in order to determine one or more fuel characteristics of the fuel by comparison to the expected TET for known types of fuel. For example, the inventors have determined that an increase in fuel calorific value would result in an increase in TET. This can be used as a method of determining if the fuel being used is SAF, as SAF typically has a higher calorific value compared to kerosene. In some examples, a TET increase of about 3K may be observed when using SAF compared to kerosene.

In another example, the fuel characteristic determination may be based on a combustor fuel to air ratio. This may be determined by the mass of fuel flow to the combustor in comparison to the core air flow. The inventors have determined that this ratio would decrease with use of a fuel such as SAF, and may therefore provide another means of determining that SAF is being used by the engine.

In yet other examples, other engine performance parameters may be used, including HP spool speed, T30 and/or T40 (as defined elsewhere herein). In other examples, the fuel flow rate required to achieve a desired fan speed at the current ambient conditions and aircraft forward speed (airspeed) may be used to determine the characteristics of the fuel being supplied to the engine. For SAF the required fuel flow rate to achieve a given fan speed will be lower (with respect to mass) or higher (with respect to volume) than the required fossil fuel flow rate to achieve the same fan speed at the same operating conditions. Similar comparisons between measured performance parameters and those expected for known fuel characteristics can be used to determine a variety of fuel characteristics.

The fuel characteristic determination module 157 may be arranged to determine each fuel characteristic based on a plurality of different engine performance parameters. The plurality of performance parameters may include at least two different performance parameters, and preferably at least three different performance parameters. The fuel characteristic may be determined based on a comparison of those different performance parameters to each other. By using more than one performance parameter the accuracy or reliability of the fuel characteristic determination may be improved.

In response to the fuel characteristic(s) determined by the fuel characteristics determination module, the operation of the gas turbine engine (or the aircraft) may be adjusted or modified accordingly during the second time period of operation. For example, engine performance parameters obtained during the take-off or climb phase may be acted upon during cruise operation or during descent.

In the present example, in which the aircraft comprises fuel tanks which may be configured to store fuel having different fuel characteristics, the gas turbine engine is only operated according to the one or more fuel characteristics during the second time period if fuel is being used from the same fuel tank, or fuel known to have the same fuel characteristics, as during the first time period. This means that the engine operation is changed only if the same fuel is being used so that the change in response to the fuel is suitable.

In one example, a fuel burn parameter or characteristic of the engine may be controlled based on the determined fuel characteristic. For example, the engine may be controlled during the cruise phase of operation from a fuel burn perspective based on the fuel characteristics determined from take-off/climb phase performance parameters. In other examples, the N1 speed of rotation of the high pressure turbine/compressor may be modified in response to the one or more fuel characteristics. For example, the N1 rotation speed may be reduced during climb so that the resulting TET matched the temperature corresponding to that when operating on kerosene (in such an example, the first flight phase may be take-off, and the second a climb phase). In other examples, the N1 rotation speed during cruise may be modified in response to the fuel characteristics determined during take-off. In yet another example, the N1 rotation speed may be modified during a descent flight phase based on the determined fuel characteristics, again by modifying the N1 rotation speed so that it corresponds to that which would be expected should the engine be running on kerosene. The N1 rotation speed in these examples may be modified by changing the corresponding rating tables in the engine control unit (e.g. the EEC 42).

Figure 28:
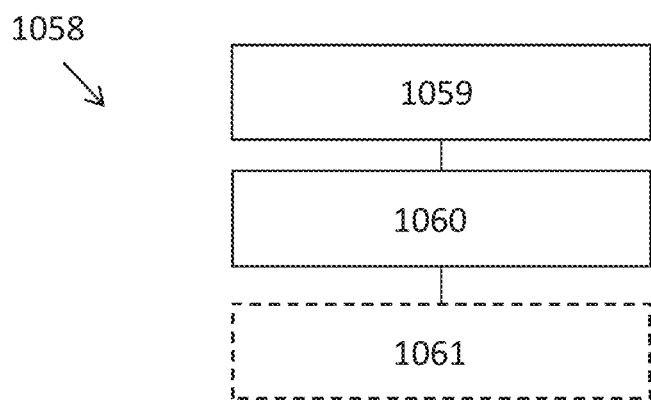
FIG. 28 is a schematic representation of another example of a method of determining fuel characteristics of an aviation fuel.

FIG. 28 illustrates a method 1058 of determining one or more fuel characteristics of an aviation fuel suitable for powering a gas turbine engine of an aircraft that can be performed by the fuel characteristic determination system 155 shown in FIG. 27 and described above. The method 1058 comprises determining 1059 one or more performance parameters of the gas turbine engine measured during a first time period of operation of the gas turbine engine. Once the performance parameters are determined, the method comprises determining 1060, one or more fuel characteristics of the fuel based on the one or more performance parameters. In some examples, the one or more fuel characteristics are determined during a second period of operation as described above, or may be determined during the first period of operation.

In some examples, the method 1058 is part of a method of operating an aircraft having the gas turbine engine (e.g. method 1065 described below), and so may include a step 1061 of operating the gas turbine engine or the aircraft according to the one or more fuel characteristics during the second time period of operation. Operation of the aircraft or the gas turbine engine may include modifying a control parameter in response to the determined fuel characteristics as described below.

Any of the features described above in connection with the fuel characteristic determination system 157 in reference to the example shown in FIG. 27 may be incorporated into the method of FIG. 28.

Aircraft Operation According to a Fuel Characteristic or Parameter on which a Fuel Characteristic Determination is Based The fuel characteristics determined using any of the fuel characteristic determination systems or methods of determining a fuel characteristic in the examples herein may be used in the operation of the aircraft, and more specifically operation of the gas turbine engine(s) of the aircraft. This may allow the operation of the aircraft 1 to be modified in response to the fuel characteristic determined.

Figure 29:
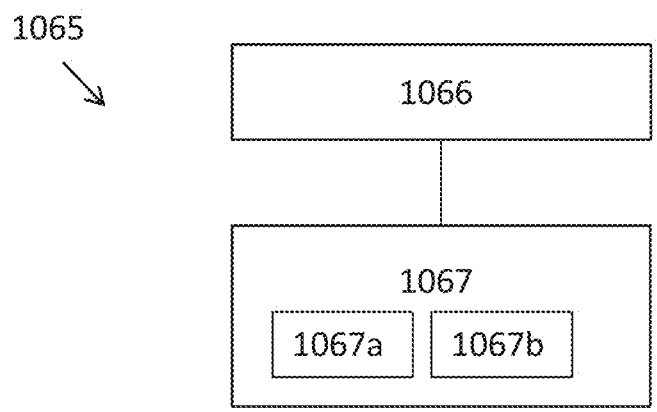
FIG. 29 is a schematic representation of a method of operating an aircraft.

The present application therefore further provides a method 1065 of operating an aircraft 1 powered by one or more gas turbine engines 10 as illustrated in FIG. 29. The method 1065 may be a method of operating the aircraft 1 of any of the examples described herein. The method 1065 comprises determining 1066 one or more fuel characteristics. This may comprise using any of the methods described herein. The method 1065 further comprises operating 1067 the aircraft 1 according to the one or more fuel characteristics. Operating the aircraft 1067 may more specifically comprise operating the gas turbine engine(s) 10 mounted to the aircraft 1, but may include operating other parts of the aircraft.

Once one or more fuel characteristics are known, the gas turbine engine 10 or the aircraft more generally may be controlled or operated in various different ways to take advantage of that knowledge. The step of operating 1067 the gas turbine engine or the aircraft may comprise modifying 1067a a control parameter of the aircraft, and specifically a control parameter of the gas turbine engine, in response to the one or more fuel characteristics. Modifying the control parameter may include any one or more of the following:
i) Modifying a control parameter of a heat management system of the gas turbine engine (e.g. a fuel-oil heat exchanger 118) based on the one or more fuel characteristics. By modifying the operation of the heat exchanger 118 the temperature of fuel supplied to the combustor 16 of the engine 10 can be changed. In one example, modifying the operation of the heat management system or changing the temperature of the fuel may comprise increasing the temperature of the fuel if the fuel characteristics indicate that the fuel can tolerate operating at a higher temperature without risk of coking or thermal breakdown.

ii) When more than one fuel is stored aboard an aircraft 1, modifying a control parameter that controls a selection of which fuel to use for which operations (e.g. for ground-based operations as opposed to flight, for low-temperature start-up, or for operations with different thrust demands) based on fuel characteristics such as % SAF, nVPM generation potential, viscosity, and calorific value. A fuel delivery system of the aircraft may therefore be controlled appropriately based on the fuel characteristics. The fuel delivery system may be controlled to supply the engine with fuel having a different fuel characteristic to that measured. This may include, for example, providing fuel with a relatively lower aromatic content; providing fuel with a lower SAF content; or providing fossil Kerosene fuel. The fuel supply may be controlled by switching between fuel tanks, or changing a fuel blend ratio.

iii) Modifying a control parameter to adjust one or more flight control surfaces of the aircraft 1, so as to change route and/or altitude based on knowledge of the fuel.

iv) Modifying a control parameter to modify the spill percentage of a fuel pump (i.e. the proportion of pumped fuel recirculated instead of being passed to the combustor) of a fuel system of the aircraft according to the one or more fuel characteristics, for example based on the % SAF of the fuel. The pump and/or one or more valves may therefore be controlled appropriately based on the fuel characteristics.

v) Modifying a control parameter to change the scheduling of variable-inlet guide vanes (VIGVs) based on fuel characteristics. The VIGVs may be moved, or a movement of the VIGVs be cancelled, as appropriate based on the fuel characteristics.

In the examples above, the gas turbine engine or the aircraft is operated according to the one or more fuel characteristics by making changes to how the aircraft or gas turbine engine are controlled during their use. This may be done, for example, by a control system of the engine (such as the EEC 42) making changes to various control parameters of the engine. Similar changes may be implemented by other control systems of the aircraft during use (e.g. during flight). The EEC may be more generally referred to as an example of a control system 42 arranged to control operation of the aircraft (e.g. it may be a control module of a control system).

The present application further provides an aircraft 1 having a fuel characteristic determination system according to any one or more of the examples disclosed or claimed herein. The aircraft further comprises a control system arranged to control operation of the aircraft according to one or more fuel characteristics determined by the fuel characteristics determination system. The control system may comprise the engine EEC 42, with which the fuel characteristic determination system may be in communication or partly integrated therein. In other examples, other control systems of the aircraft may be provided with fuel characteristics and the aircraft controlled accordingly. The control system may be arranged to control operation of the aircraft according to a parameter on which a fuel characteristic determination is based directly, rather than requiring a fuel characteristic to be determined as described below.

The step of operating 1067 the gas turbine engine or aircraft according to the one or more fuel characteristics may be performed automatically in response to the determination of fuel properties without any intervention of the pilot. In some examples, it may be performed after approval by a pilot, following the pilot being notified of a proposed change. In some examples, the step 1067a may include automatically making some changes, and requesting others, depending on the nature of the change. In particular, changes which are "transparent" to the pilot—such as internal changes within engine flows which do not affect engine power output and would not be noticed by a pilot—may be made automatically, whereas any changes which the pilot would notice may be notified to the pilot (i.e. a notification appearing that the change will happen unless the pilot directs otherwise) or suggested to the pilot (i.e. the change will not happen without positive input from the pilot). In implementations in which a notification or suggestion is provided to a pilot, this may be provided on a cockpit display of the aircraft, and/or sent to a separate device such as a portable tablet or other computing device, and/or announced via audible sound such as synthesized speech or recorded message or a particular tone indicative of the proposed/notified change.

In other examples, the step of operating 1067 the gas turbine engine according to the one or more fuel characteristics may include providing 1067b the gas turbine engine with fuel having different characteristics to that of the fuel for which the one or more fuel characteristics were measured in step 1066. This provision of a different fuel may include loading fuel having different fuel characteristics into the fuel tanks of the aircraft when refueling the aircraft.

In some examples, operation of the aircraft may be modified in response to one or more of the parameters disclosed herein upon which the fuel characteristics are determined. This may include, for example, the vibration parameter, swell parameter, trace substance parameter, UV-Vis transmittance parameter, contrail parameter, exhaust parameter, and engine performance parameter. The aircraft may therefore be controlled based on such parameters, without a fuel characteristic necessarily also being calculated.

Figure 30:
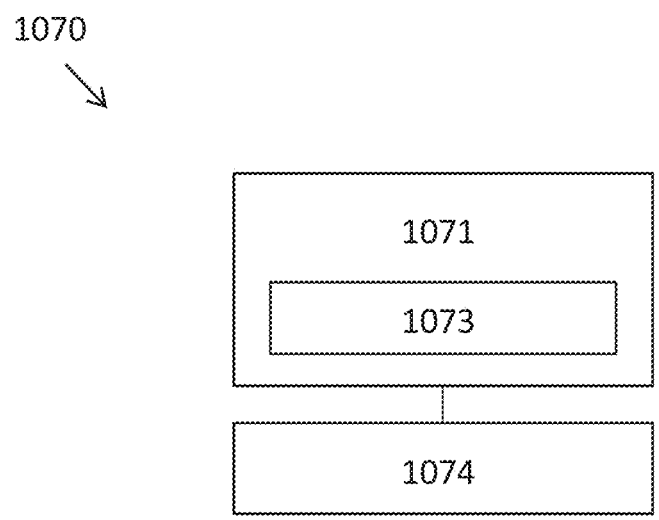
FIG. 30 is a schematic representation of another method of operating an aircraft.

In one such example, the operation of the aircraft may be modified in response to the one or more contrail parameters, without a fuel characteristic being determined. An example of such a method is shown in FIG. 30. FIG. 30 illustrates a method 1070 of operating an aircraft 1 having a gas turbine engine 10. The method 1070 comprises: determining 1071, during use of the gas turbine engine 10, one or more contrail parameters related to contrail formation by the gas turbine engine 10.

Determining 1071 the one or more contrail parameters comprises performing 1073 a sensor measurement on a region behind the gas turbine engine in which a contrail is or can be formed as described above in connection with the example shown in FIG. 23. The contrail parameters are determined in step 1071 during varying operation of the aircraft (e.g. during a period of varying engine operating parameter and/or ambient condition parameter). The contrail parameters determined may indicate the value of a varying parameter at which a contrail is first formed. Once the one or more contrail parameters are determined in this way, the method 1070 further comprises controlling 1074 an operating parameter of the aircraft according to the one or more contrail parameters and the value of the varying parameter to which they correspond. As discussed above, this may involve measuring the engine performance parameters and/or ambient conditions at which contrail formation begins during a climb phase of the aircraft operation. The control of the aircraft may additionally or alternatively include any of the examples of control of the aircraft in response to fuel characteristics described above.

Figure 31:
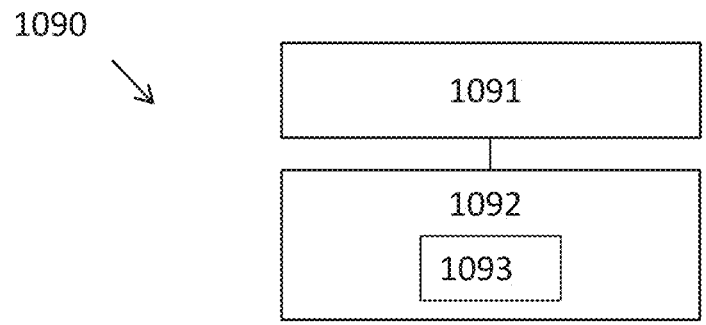
FIG. 31 is a schematic representation of yet another method of operating an aircraft.

Another example in which the aircraft is controlled based on a sensor parameter rather than a fuel characteristic is illustrated in FIG. 31. In this example, steps 1026, 1027 and 1028 of method 1025 shown in FIG. 14 are incorporated into a method of operating an aircraft. In this example therefore, FIG. 31 illustrates a method of operating an aircraft 1090 which comprises measuring 1091 a swell parameter of a seal material (which is the same material as other seals 125 provided on the aircraft 1) using the steps of method 1025. The method 1090 further comprises operating 1092 the aircraft according to the swell parameter. Operating 1092 the aircraft according to the swell parameter may include providing 1093 the one or more gas turbine engines with fuel having a different characteristic compared to the fuel for which the swell parameter was measured. The fuel having a different characteristic may be provided by refueling the aircraft with fuel having a different characteristic to that already in its fuel tank(s), or by suppling fuel from a different fuel tank onboard the aircraft which holds fuel having a different characteristic. Suppling fuel from a different fuel source on board the aircraft may comprise altering a blend of fuels from different fuel sources, or switching between fuel having different characteristics. Providing fuel having a different characteristic may comprise any one or more of: i) providing fuel with a relatively higher aromatic content; ii) providing fuel with a lower SAF content; iii) providing kerosene. This may allow seal swell to be increased if operation using the current fuel is determined to provide inadequate seal swell, which could lead to a reduction in seal performance.

In the previously described examples, the various fuel characteristic determination systems are arranged to determine the one or more fuel characteristics based only on the respective parameter described in each example (e.g. on only one of a vibration parameter, swell parameter, trace substance parameter, UV-Vis transmittance parameter, contrail parameter, exhaust parameter, or engine performance parameter) In other examples, any of the fuel characteristic determination modules or methods of determining one or more fuel characteristics described or claimed herein may be arranged to base the fuel characteristics on any one or more of the parameters described herein i.e. any one or more of the vibration parameter, swell parameter, trace substance parameter, UV-Vis transmittance parameter, contrail parameter, exhaust parameter, and engine performance parameter. This may allow a greater range or types of fuel characteristic to be determined, or may improve the accuracy or reliability of the fuel characteristic determination.

In any of the examples described herein, characteristics of fuel as it is being loaded onto the aircraft may be determined (e.g. as shown in the examples of FIGS. 5, 9, 13, 15 and 19). In such examples, the one or more fuel characteristics determined may be communicated to the EEC 42 directly if it is running during refueling, or may otherwise stored and communicated to the EEC when it is activated. If the EEC is not active when fuel characteristics are determined, they may be communicated to another control system of the aircraft.

Where fuel characteristics are determined for fuel being loaded onto the aircraft that fuel may be mixed with fuel already present in the fuel tanks (e.g. from previous flights). The determined fuel characteristics may therefore be combined with those determined from previous times at which the aircraft was refueled in order to determine the characteristics of the fuel stored in the aircraft fuel tanks. This may be done using a summing method in which the amount of fuel loaded into the tanks, the amount of fuel used during each flight, and the corresponding characteristics of the fuel loaded are logged and combined to determine the fuel characteristics of fuel actually stored within the aircraft tanks at a given time.

Maintenance Schedule Generation According to Fuel Characteristics

The one or more fuel characteristics determined using any of the methods described or claimed herein may be used in the generation of a maintenance schedule for the respective gas turbine engine, or more generally the aircraft on which the gas turbine engine is mounted.

Figure 32:
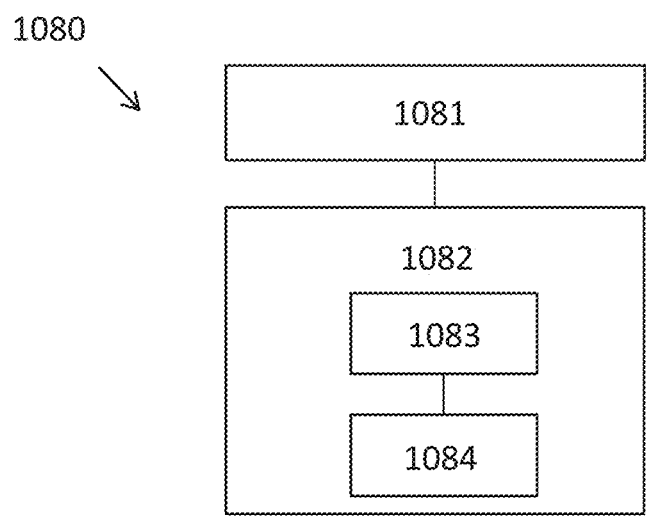
FIG. 32 is a schematic representation of a method of generating a maintenance schedule for an aircraft.

FIG. 32 illustrates an example of a method 1080 of generating a maintenance schedule for an aircraft. The aircraft comprises one or more gas turbine engines, and may be the aircraft 1 described in respect to any of the other examples herein. The method 1080 comprises determining 1081 one or more fuel characteristics of a fuel with which the gas turbine engine has been, or is to be, powered. The one or more fuel characteristics may be those of a fuel or fuels used during previous uses of the gas turbine engine, or fuel held within the fuel tanks of the aircraft. The one or more fuel characteristics may be determined using any of the methods described herein, but is not limited to only those methods in other examples. The fuel characteristics may be determined as described herein and provided automatically to a maintenance schedule determination module without human intervention. In some other examples, determining the one or more fuel characteristics may involve them being input manually to a maintenance schedule determination module, e.g. during re-fueling of the aircraft. This may include reading the fuel characteristics from a fuel specification, or from the output of a fuel characteristic determination system, and inputting them manually by a human user to the maintenance schedule determination module. The method 1080 further comprises generating 1082 maintenance schedule according to the one or more fuel characteristics. In other examples, one or more maintenance schedules (e.g. one for each engine) may be determined.

The inventors have determined that the characteristics of the fuel that has been used to power the gas turbine have an effect on the operation of the gas turbine engine and the aircraft in general and so may require a change in a maintenance schedule for that gas turbine engine or aircraft. The change in the maintenance schedule may include a change to the maintenance operations scheduled to take place, and/or a change to the time/frequency at which maintenance operations are performed. In some examples, generation of a maintenance schedule may include the modification of an existing schedule in response to the fuel characteristics, or the generation of a new one.

The step of generating 1082 the maintenance schedule may comprise comparing 1083 the one or more determined fuel characteristics to an expected fuel characteristic, and modifying 1084 a maintenance schedule accordingly. An existing pre-defined maintenance schedule for a gas turbine engine, or aircraft in general, may be associated with an expected fuel characteristic. For example, the maintenance schedule may be determined according to a specified type of fuel to be used by the aircraft so that maintenance can be performed based on how the engine is expected to operate using that fuel. The existing maintenance schedule may be modified in response to determining that a deviation from the expected fuel characteristics has occurred. This may allow the maintenance schedule to be tailored to the actual fuel that has been used, rather than by assuming that the specified fuel has been used.

In one example, the existing maintenance schedule may specify operation of the aircraft 1 using a fuel having a specific SAF content, for example, a SAF rich fuel having a certain proportion of SAF compared to fossil kerosene, or require 100% SAF fuel to be used. Deviation from use of fuel with the specified SAF content as indicated by the determined fuel characteristics may result in a modification to the maintenance schedule to account for operation outside of specification. In other examples, the modification of the maintenance schedule may be based on other characteristics of the fuel as defined elsewhere herein. For example, the aromatic content of the fuel, or an indication that fossil kerosene has been used, may be determined and the maintenance schedule modified or otherwise generated accordingly.

In some examples, a periodic measurement of the fuel characteristics may be performed on which the maintenance schedule determination is based. This may allow the maintenance schedule to be generated based on an effect on the performance of the engine or aircraft that may occur over a prolonged period of use with fuel having certain properties. This may allow slow changes in the performance of the engine to be taken into account, rather than using a "real-time" modification of the maintenance schedule based on only a single real-time fuel characteristic determination. For example, the one or more fuel characteristics determined in step 1081 may indicate that a threshold level of fuel coking or thermal breakdown has taken place. This may lead to surface deposit build up within components of the gas turbine engine over time (e.g. fuel nozzles), and may require more frequent maintenance or susceptible components to be replaced or cleaned. By using periodic determination of the fuel characteristics the level of coking may be monitored over time and the maintenance schedule adapted accordingly.

In some examples, determining the one or more fuel characteristics may comprise measuring a change in the properties of a sensor component which is exposed to the fuel used to power the engines 10 of the aircraft. The sensor component may in some examples be a piezoelectric crystal which is exposed to fuel loaded onto the aircraft or being used by the gas turbine engine as discussed in connection with the examples shown in FIGS. 5 to 8. In this example, the method 1080 may therefore make use of the fuel determination system 114 described in the examples above. Determining the one or more fuel characteristics in such an example may comprise measuring a vibration mode of the piezoelectric crystal, which provides an indication of a surface deposit formed on the crystal. The maintenance schedule may be modified based on the detection of such a surface deposit indicating that fuel having a characteristic causing surface deposits to form with the engine or fuel system has been used, and maintenance is to be carried out accordingly. The maintenance schedule may be modified according to a threshold level of coking or fuel thermal breakdown having been exceeded. In such an example, the fuel characteristic may be an indication that the fuel has caused a surface deposit, rather than requiring a further determination of a fuel characteristic that is associated with such surface deposit formation being found. This may allow the maintenance schedule to be modified based on a surface deposit formed, regardless of by what mechanism it was formed.

In other examples, the method 1081 may make use of the detection device 120 illustrated in FIGS. 10, 11 and 13 and described above. In this example, the sensor component which is exposed to fuel and on which fuel characteristic determination is based comprises a seal material 121. This may be a seal material which is the same as one or more seals used within the fuel system of the gas turbine engine 10 as described above in connection with FIGS. 13 and 14. As discussed above, one or more fuel characteristics may be determined based on a swell parameter of the seal material. The inventors have determined that the one or more fuel characteristics determined in this way may be used to generate a maintenance schedule according to the effect the fuel characteristics will have on seals that are exposed to fuel on board the aircraft (e.g. in the fuel system arranged to store and supply fuel to the gas turbine engine, and within the engine itself). In this example, the one or more fuel characteristics on which the maintenance schedule is generated indicate whether a threshold level of swell of the seal material has occurred. If the swell has not exceeded a predetermined threshold, this may indicate that sealing performance may have been inhibited and the maintenance schedule should be generated or modified accordingly.

Figure 33:
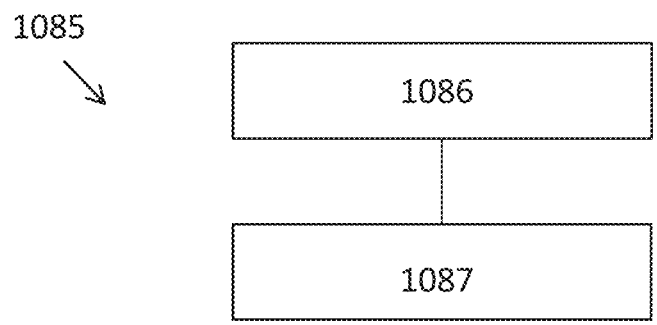
FIG. 33 is a schematic representation of a method of maintaining an aircraft.

The method 1080 of generating a maintenance schedule for an aircraft may be part of a method of maintaining an aircraft. An example of such a method 1085 is illustrated in FIG. 33. The method 1085 of maintaining an aircraft comprises generating 1086 a maintenance schedule using the method 1080 described above. Once the maintenance schedule has been generated, the method 1085 comprises performing 1087 maintenance on the aircraft according to the maintenance schedule. Performing maintenance may comprise performing maintenance on the gas turbine engine(s) 10, or on the aircraft more generally. The step of performing maintenance may comprise steps taken by a technician in response to the generated maintenance schedule. In other examples, maintenance steps may be performed automatically without the intervention of a technician. For example, software updates or changes to control programs (e.g. those of the EEC) may be performed automatically during maintenance process without human intervention.

Figure 34:
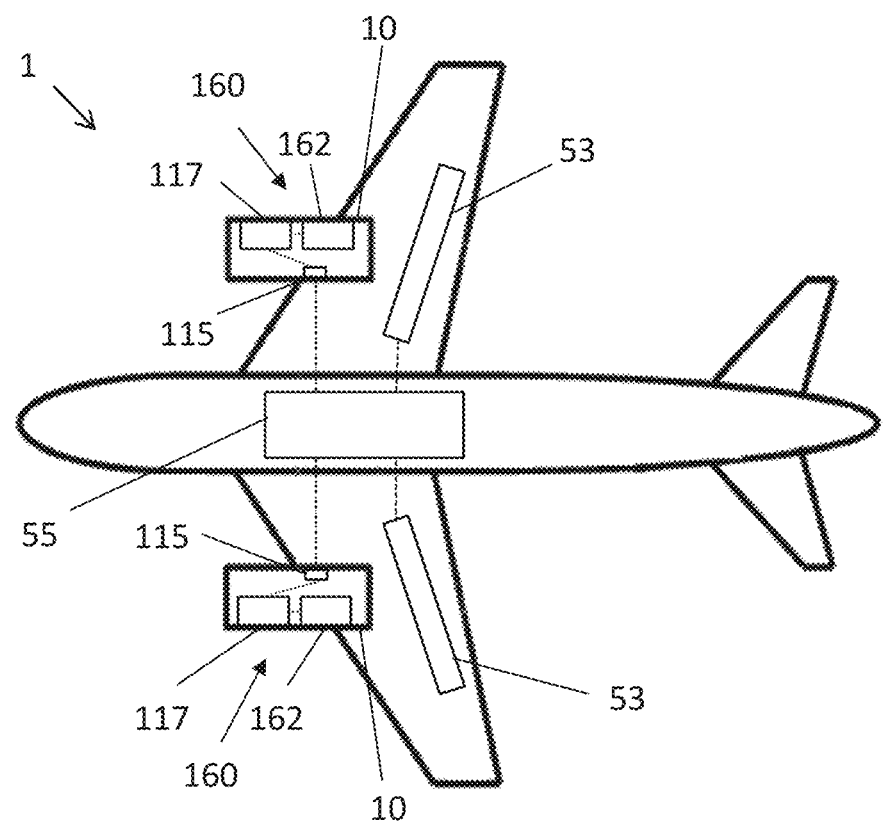
FIG. 34 is a schematic view on an aircraft having a maintenance schedule generation system.

FIG. 34 illustrates an example of an aircraft 1 having a maintenance schedule generation system 160 arranged to carry out the method 1085 of FIG. 32. The maintenance schedule generation system 160 in this example comprises a fuel characteristic determination module 117 corresponding to the example described above, in which fuel characteristics are determined based on a vibrational parameter of a piezoelectric crystal (e.g. using sensor 115 which comprises a piezoelectric crystal 116 as described above). The fuel characteristic determination module may however be any one or more of those disclosed or claimed elsewhere herein.

The maintenance schedule generation system 160 further comprises a maintenance schedule generation module 162 in communication with the fuel characteristic determination module 117 and configured to generate a maintenance schedule according to the one or more fuel characteristics received therefrom. The maintenance schedule generation module 162 may be configured to generate the maintenance schedule as described above.

The maintenance schedule generation system 160 may be located on board the aircraft 1 as shown in the example of FIG. 34. In this example, a separate maintenance schedule generation system 160 is provided for each engine 10. In other examples, a single system may be provided, for example having a single generation module 162 configured to receive fuel characteristics from a single fuel characteristic determination module on board the aircraft, or from separate fuel characteristic determination modules provided for each engine. A single maintenance schedule for the aircraft 1 as a whole may be produced, or separate maintenance schedules for each engine 10 produced accordingly.

In other examples, the maintenance generation system 160 may be located at least partly outside of the aircraft 1. For example, the maintenance schedule generation module 162 may be located separately from the aircraft 1, and may be configured to communicate via a wired or wireless data link connection with a fuel characteristic determination module so that the one or more fuel characteristics may be received and a maintenance schedule generated accordingly.

The maintenance schedule generation module 162 may be arranged to output a maintenance schedule to a technician performing maintenance on the aircraft 1, or to an aircraft health monitoring system arranged to manage the maintenance of the aircraft 1 (or engines 10 separately). In some examples, the maintenance generation module 162 may be in communication with the EEC 42 so that updates or reconfiguration of control parameters stored in the EEC may be carried out (e.g. automatically).

It will be understood that the invention is not limited to the examples above-described and various modifications and improvements can be made without departing from the concepts described herein. Except where mutually exclusive, any of the features may be employed separately or in combination with any other features and the disclosure extends to and includes all combinations and sub-combinations of one or more features described herein.

We claim:

1. A method of determining one or more fuel characteristics of an aviation fuel for powering a gas turbine engine of an aircraft, the method comprising:
   measuring one or more trace substance parameters of the fuel, the one or more trace substance parameters each associated with a respective trace substance in the fuel; and
   determining one or more fuel characteristics of the fuel based on the one or more trace substance parameters, wherein the one or more fuel characteristics include:
   a) a percentage of sustainable aviation fuel in the fuel; or
   b) an indication that the fuel is a fossil fuel.

2. The method of claim 1, wherein at least one of the one or more trace substance parameters indicate the presence or a concentration of the associated trace substance in the fuel.

3. The method of claim 2, wherein at least one of the one or more trace substance parameters indicate the absence of the associated trace substance in the fuel.

4. The method of claim 1, wherein the trace substance associated with at least one of the trace substance parameters occurs inherently in the fuel.

5. The method of claim 1, wherein the trace substance parameters include:
   i) a concentration or amount of sulphur within the fuel; and/or
   ii) a concentration or amount of aromatic hydrocarbon within the fuel.

6. The method of claim 1, wherein the trace substance associated with at least one of the trace substance parameters is added to the fuel to act as a tracer for detection.

7. The method of claim 1, wherein measuring the one or more trace substance parameters comprises performing spectroscopy on the fuel.

8. The method of claim 1, wherein measuring the one or more trace substance parameters comprises performing fluorescence detection.

9. The method of claim 1, wherein measuring the one or more trace substance parameters comprises performing a measurement on fuel onboard the aircraft, and optionally wherein:

a) measuring the one or more trace substance parameters comprises performing a measurement on fuel within, sampled from, or being delivered to a fuel tank of the aircraft; and/or b) measuring the one or more trace substance parameters comprises performing a measurement on fuel during use of the gas turbine engine.

10. The method of claim 1, wherein measuring the one or more trace substance parameters comprises performing a measurement on fuel outside of the aircraft during a fuel loading process in which a fuel tank or tanks of the aircraft are loaded with fuel.

11. A method of operating an aircraft having a gas turbine engine, the method comprising:
   determining the one or more fuel characteristics using the method of claim 1; and
   operating the aircraft according to the one or more fuel characteristics.

12. The method of claim 11, wherein operating the aircraft according to the one or more fuel characteristics comprises:
   a) modifying a control parameter of the aircraft in response to the one or more fuel characteristics; and/or
   b) providing a fuel having different fuel characteristics during refueling of the aircraft.

13. The method of claim 1, wherein determining the one or more fuel characteristics includes comparing a measured value of the one or more trace substance parameters of the fuel to an expected value of the one or more trace substance parameters of a fossil fuel with known fuel characteristics to determine the percentage of sustainable aviation fuel in the fuel or the indication that the fuel is a fossil fuel.

14. The method of claim 1, wherein determining the one or more fuel characteristics includes at least one of:
   a) comparing a measured concentration or amount of sulphur in the fuel to an expected concentration or amount of sulphur in a fossil fuel with known fuel characteristics to determine the percentage of sustainable aviation fuel in the fuel, or the indication that the fuel is a fossil fuel; and
   b) comparing a measured concentration or amount of aromatic hydrocarbon in the fuel to an expected concentration or amount of aromatic hydrocarbon in a fossil fuel with known fuel characteristics to determine the percentage of sustainable aviation fuel in the fuel, or the indication that the fuel is a fossil fuel.

15. A fuel characteristic determination system for determining one or more fuel characteristics of an aviation fuel for powering a gas turbine engine of an aircraft, the system comprising:
   a sensor configured to measure one or more trace substance parameters of the fuel, the one or more trace substance parameters each associated with a respective trace substance in the fuel; and
   a determination module configured to determine one or more fuel characteristics of the fuel based on the one or more trace substance parameters, wherein the one or more fuel characteristics include:
   a) a percentage of sustainable aviation fuel in the fuel; or
   b) an indication that the fuel is a fossil fuel.

16. The fuel characteristic determination system of claim 15, wherein at least one of the one or more trace substance parameters indicate the presence or a concentration of the associated trace substance in the fuel, and optionally:
   wherein at least one of the one or more trace substance parameters indicates the absence of the associated trace substance in the fuel.

17. The fuel characteristic determination system of claim 15, wherein:
   a) the sensor comprises a spectroscopy device; and/or
   b) the sensor comprises a fluorescence detection device.

18. The fuel characteristic determination system of claim 15, wherein the sensor is configured to perform a measurement on fuel onboard the aircraft, and optionally wherein:
   a) the sensor is arranged to perform a measurement on fuel within, sampled from, or being delivered to a fuel tank of the aircraft;
   b) the sensor is arranged to perform a measurement on fuel during use of the gas turbine engine; and/or
   c) the sensor is arranged to perform a measurement on fuel outside of the aircraft that is being loaded onto the aircraft during a fuel loading process.

19. An aircraft comprising the fuel characteristic determination system of claim 15, further comprising a control system arranged to control operation of the aircraft according to the one or more fuel characteristics determined by the fuel characteristic determination system.

20. The fuel characteristic determination system of claim 15, wherein the determination module is configured to determine the one or more fuel characteristics of the fuel by comparing a measured value of the one or more trace substance parameters of the fuel to an expected value of the one or more trace substance parameters of a fossil fuel with known fuel characteristics to determine the percentage of sustainable aviation fuel in the fuel or the indication that the fuel is a fossil fuel.

* * * * *